US010000497B2

(12) United States Patent
Horsley et al.

(10) Patent No.: US 10,000,497 B2
(45) Date of Patent: Jun. 19, 2018

(54) FUSED BICYCLIC HETEROAROMATIC DERIVATIVES AS KINASE INHIBITORS

(71) Applicants: UCB Biopharma SPRL, Brussels (BE); Katholieke Universiteit Leuven, K.U.Leuven R&D, Leuven (BE)

(72) Inventors: Helen Tracey Horsley, Slough (GB); Qiuya Huang, Leuven (BE); Judi Charlotte Neuss, Slough (GB); James Thomas Reuberson, Slough (GB); Bart Vanderhoydonck, Diest (BE)

(73) Assignees: UCB BIOPHARMA SPRL, Brussels (BY); KATHOLIEKE UNIVERSITEIT LEUVEN, K.U.LEUVEN R&D, Leuven (BE)

( * ) Notice: Subject to any disclaimer, the term of this patent is extended or adjusted under 35 U.S.C. 154(b) by 0 days. days.

(21) Appl. No.: 15/318,507

(22) PCT Filed: Jun. 11, 2015

(86) PCT No.: PCT/EP2015/063052
§ 371 (c)(1),
(2) Date: Dec. 13, 2016

(87) PCT Pub. No.: WO2015/193169
PCT Pub. Date: Dec. 23, 2015

(65) Prior Publication Data
US 2017/0121337 A1 May 4, 2017

(30) Foreign Application Priority Data
Jun. 17, 2014 (GB) .................................. 1410817.9

(51) Int. Cl.
| | | |
|---|---|---|
| C07D 487/04 | (2006.01) | |
| C07D 403/04 | (2006.01) | |
| A61K 31/53 | (2006.01) | |
| A61K 31/495 | (2006.01) | |
| A61P 33/06 | (2006.01) | |
| A61P 37/06 | (2006.01) | |

(52) U.S. Cl.
CPC .......... *C07D 487/04* (2013.01); *A61K 31/495* (2013.01); *A61K 31/53* (2013.01); *C07D 403/04* (2013.01)

(58) Field of Classification Search
CPC .... C07D 487/04; C07D 403/04; A61K 31/53; A61K 31/495
USPC ........................... 544/194, 212; 514/245, 246
See application file for complete search history.

(56) References Cited

FOREIGN PATENT DOCUMENTS

| | | |
|---|---|---|
| DE | 2424334 | 12/1974 |
| EP | 0591528 | 4/1994 |
| WO | 2005/002514 | 1/2005 |
| WO | 2005/110413 | 11/2005 |
| WO | 2008/058126 | 5/2008 |
| WO | 2009/123986 | 10/2009 |
| WO | 2010/103130 | 9/2010 |
| WO | 2011/163518 | 12/2011 |
| WO | 2013/034738 | 3/2013 |
| WO | 2013/068458 | 5/2013 |

OTHER PUBLICATIONS

Burke etal. Science. May 30, 2014; 344(6187): 1035-1038.*
McNamara et al. Nature, 2013, 504, 248-253.*
Cecil Textbook of Medicine, edited by Bennet, J.C., and Plum F., 20th edition,vol. 1, 1004-1010.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Medjdrova et al., "Highly Selective Phosphatidylinositol 4-Kinase III[beta] Inhibitors and structural Insight into Their Mode of Action," Journal of Medicinal Chemistry, vol. 58, No. 9, May 14, 2015, pp. 3767-3793.
Database Registry [Online] Chemical Abstracts Service, Columbus, Ohio, Jun. 13, 2012, XP002743076.
Database Registry [Online] Chemical Abstracts Service, Columbus, Ohio, Jun. 13, 2012, XP002743077.
Database Registry [Online] Chemical Abstracts Service, Columbus, Ohio, Jun. 13, 2012, XP002743078.
Database Registry [Online] Chemical Abstracts Service, Columbus, Ohio, Jun. 13, 2012, XP002743079.
Database Registry [Online] Chemical Abstracts Service, Columbus, Ohio, Jun. 13, 2012, XP002743080.
Database Registry [Online] Chemical Abstracts Service, Columbus, Ohio, Jun. 13, 2012, XP002743081.

(Continued)

*Primary Examiner* — Venkataraman Balasubramanian
(74) *Attorney, Agent, or Firm* — McDonnell Boehnen Hulbert & Berghoff LLP

(57) ABSTRACT

A series of fused bicyclic heteroaromatic derivatives of formula (I), as defined herein, being selective inhibitors of phosphatidylinositol-4-kinase IIIβ (PI4KIIIβ) activity, are beneficial in the treatment and/or prevention of various human ailments, including inflammatory, autoimmune and oncological disorders; viral diseases and malaria; and organ and cell transplant rejection.

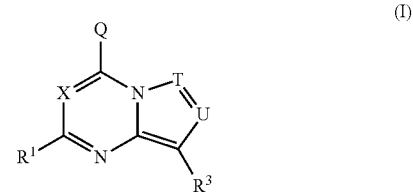

(I)

13 Claims, No Drawings

(56) References Cited

OTHER PUBLICATIONS

Database Registry [Online] Chemical Abstracts Service, Columbus, Ohio, Jun. 13, 2012, XP002743082.
Database Registry [Online] Chemical Abstracts Service, Columbus, Ohio, Jun. 13, 2012, XP002743083.
Written Opinion and International Search Report of PCT/EP2015/063052 filed Jun. 11, 2015 dated Sep. 7, 2015, 17 pages.

* cited by examiner

FUSED BICYCLIC HETEROAROMATIC DERIVATIVES AS KINASE INHIBITORS

This application is a US national phase of International Application No. PCT/EP2015/063052, filed Jun. 11, 2015, which claims priority to Great Britain Application No. 1410817.9, filed Jun. 17, 2014.

The present invention relates to a family of fused bicyclic heteroaromatic derivatives, and to their use in therapy. The compounds provided by the present invention are selective inhibitors of phosphatidylinositol-4-kinase IIIβ (PI4KIIIβ) activity, and are accordingly of benefit as pharmaceutical agents, especially in the treatment of adverse inflammatory, autoimmune and oncological disorders, in the treatment of viral diseases and malaria, and in the management of organ and cell transplant rejection.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/034738 discloses that inhibitors of PI4KIIIβ activity are useful as medicaments for the treatment of autoimmune and inflammatory disorders, and organ and cell transplant rejection.

WO 2010/103130 describes a family of oxazolo[5,4-d]pyrimidine, thiazolo[5,4-d]-pyrimidine, thieno[2,3-d]pyrimidine and purine derivatives that are active in a range of assays, including the Mixed Lymphocyte Reaction (MLR) test, and are stated to be effective for the treatment of immune and autoimmune disorders, and organ and cell transplant rejection. WO 2011/147753 discloses the same family of compounds as having significant antiviral activity. Furthermore, WO 2012/035423 discloses the same family of compounds as having significant anticancer activity.

WO 2013/024291, WO 2013/068458, WO 2014/053581, and copending international patent application PCT/EP2013/077846 (published on 26 Jun. 2014 as WO 2014/096423) describe various series of fused pyrimidine derivatives that are stated to be of benefit as pharmaceutical agents, especially in the treatment of adverse inflammatory, autoimmune and oncological disorders, in the treatment of viral diseases, and in the management of organ and cell transplant rejection.

Inhibitors of PI4KIIIβ have been identified as molecules with an ideal activity profile for the prevention, treatment and elimination of malaria (cf. C. W. McNamara et al., *Nature*, 2013, 504, 248-253).

None of the prior art available to date, however, discloses or suggests the precise structural class of fused bicyclic heteroaromatic derivatives as provided by the present invention as having activity as PI4KIIIβ inhibitors.

The compounds of the present invention are potent and selective inhibitors of PI4KIIIβ activity, inhibiting the kinase affinity of human PI4KIIIβ ($IC_{50}$) at concentrations of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for human PI4KIIIβ relative to other human kinases.

Certain compounds in accordance with the present invention are active as inhibitors when subjected to the Mixed Lymphocyte Reaction (MLR) test. The MLR test is predictive of immunosuppression or immunomodulation. Thus, when subjected to the MLR test, certain compounds of the present invention display an $IC_{50}$ value of 10 μM or less, generally of 5 μM or less, usually of 2 μM or less, typically of 1 μM or less, suitably of 500 nM or less, ideally of 100 nM or less, and preferably of 20 nM or less (again, the skilled person will appreciate that a lower $IC_{50}$ figure denotes a more active compound).

The compounds of the invention possess notable advantages in terms of their high potency, demonstrable efficacy at lower doses, and valuable pharmacokinetic and pharmacodynamic properties (including clearance and bioavailability).

The present invention provides a compound of formula (I) or an N-oxide thereof, or a pharmaceutically acceptable salt or solvate thereof:

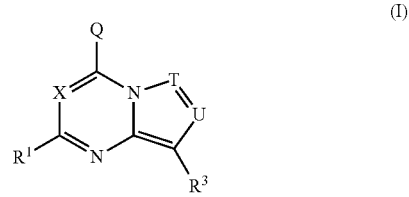

wherein

X represents N or CH;

T and U independently represent N or C—$R^2$;

Q represents a group of formula (Qa), (Qb), (Qc), (Qd) or (Qe):

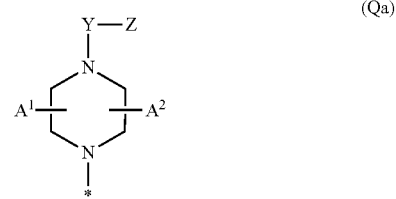

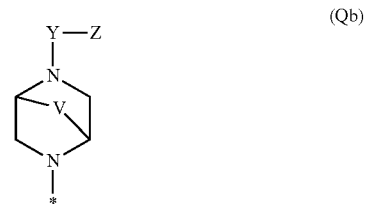

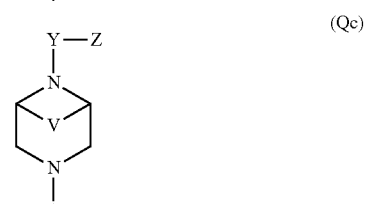

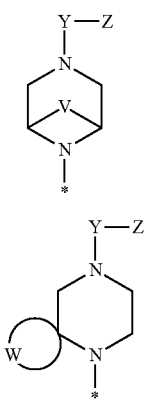

(Qd)

(Qe)

in which the asterisk (*) represents the point of attachment to the remainder of the molecule;

V represents —CH$_2$—, —C(CH$_3$)$_2$—, —CH$_2$CH$_2$— or —CH$_2$CH$_2$CH$_2$—;

W represents the residue of a C$_{3-7}$ cycloalkyl group;

Y represents a covalent bond, or a linker group selected from —C(O)—, —S(O)—, —S(O)$_2$—, —C(O)O—, —C(O)N(R$^4$)—, —C(O)C(O)— and —S(O)$_2$N(R$^4$)—, or a linker group of formula (Ya):

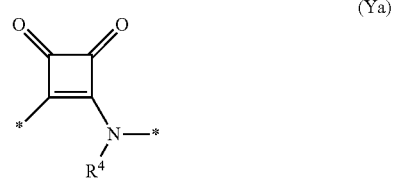

(Ya)

in which the asterisk (*) represents the point of attachment to the remainder of the molecule;

Z represents hydrogen; or Z represents C$_{1-6}$ alkyl, C$_{2-6}$ alkenyl, C$_{3-7}$ cycloalkyl, C$_{3-7}$ cycloalkyl(C$_{1-6}$)alkyl, C$_{3-7}$ heterocycloalkyl, C$_{3-7}$ heterocycloalkyl(C$_{1-6}$)alkyl, aryl, aryl(C$_{1-6}$)alkyl, heteroaryl or heteroaryl(C$_{1-6}$)alkyl, any of which groups may be optionally substituted by one or more substituents;

A$^1$ represents hydrogen, cyano or trifluoromethyl; or A$^1$ represents C$_{1-6}$ alkyl, optionally substituted by one or more substituents independently selected from fluoro, —OR$^a$, trifluoromethoxy, —NR$^b$R$^c$, —CO$_2$R$^d$ and —CONR$^b$R$^c$; or A$^1$ represents C$_{3-7}$ cycloalkyl;

A$^2$ represents hydrogen or C$_{1-6}$ alkyl;

R$^1$ and R$^2$ independently represent hydrogen, halogen, cyano, nitro, hydroxy, trifluoromethyl, trifluoromethoxy, —OR$^a$, —SR$^a$, —SOR$^a$, —SO$_2$R$^a$, —NR$^b$R$^c$, —CH$_2$NR$^b$R$^c$, —NR$^c$COR$^d$, —CH$_2$NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or C$_{1-6}$ alkyl, C$_{3-7}$ cycloalkyl, C$_{3-7}$ cycloalkyl(C$_{1-6}$)alkyl, aryl, aryl (C$_{1-6}$)alkyl, C$_{3-7}$ heterocycloalkyl, C$_{3-7}$ heterocycloalkyl (C$_{1-6}$)alkyl, C$_{3-7}$ heterocycloalkenyl, heteroaryl or heteroaryl(C$_{1-6}$)alkyl, any of which groups may be optionally substituted by one or more substituents;

R$^3$ represents hydrogen, halogen or C$_{1-6}$ alkyl;

R$^4$ represents hydrogen; or R$^4$ represents C$_{1-6}$ alkyl, optionally substituted by one or more substituents independently selected from —OR$^a$ and —NR$^b$R$^c$;

R$^a$ represents hydrogen; or R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl (C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$) alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents; and R$^e$ represents C$_{1-6}$ alkyl, aryl or heteroaryl, any of which groups may be optionally substituted by one or more substituents.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched C$_{1-6}$ alkyl groups, for example C$_{1-4}$ alkyl groups. Typical examples include methyl and ethyl groups, and straight-chained or branched propyl, butyl, pentyl and hexyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl, allyl and prop-1-en-2-yl.

Suitable $C_{3-7}$ cycloalkyl groups, which may comprise benzo-fused analogues thereof, include cyclopropyl, cyclobutyl, cyclopentyl, indanyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include oxetanyl, azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Examples of suitable heterocycloalkenyl groups include oxazolinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, imidazo[2,1-b]thiazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, benzothiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)⇌enol (CH=CHOH) tautomers or amide (NHC=O)⇌hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$.

Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, X represents N. In another embodiment, X represents CH.

In one embodiment, T represents N. In another embodiment, T represents C—$R^2$.

In one embodiment, U represents N. In another embodiment, U represents C—$R^2$.

In a first embodiment, T represents N and U represents C—$R^2$.

In a second embodiment, T and U both represent N.

In a third embodiment, T represents C—$R^2$ and U represents N.

In a fourth embodiment, T and U both represent C—$R^2$, in which the $R^2$ groups attached to T and U may be the same or different.

A particular sub-class of compounds in accordance with the present invention comprises the compounds of formula (IA):

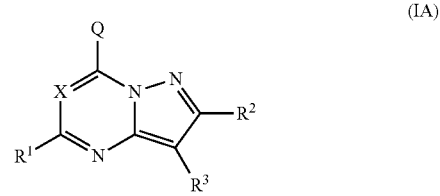

(IA)

wherein X, Q, $R^1$, $R^2$ and $R^3$ are as defined above.

In a particular embodiment, Q represents a group of formula (Qa) as defined above. In a second embodiment, Q represents a group of formula (Qb) as defined above. In a third embodiment, Q represents a group of formula (Qc) as defined above. In a fourth embodiment, Q represents a group of formula (Qd) as defined above. In a fifth embodiment, Q represents a group of formula (Qe) as defined above.

Where Q represents a group of formula (Qa) as defined above, this may be a group of formula (Qa-1), (Qa-2), (Qa-3), (Qa-4), (Qa-5) or (Qa-6):

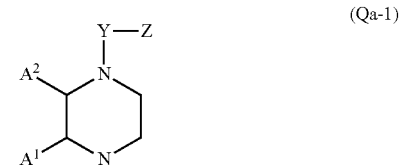

(Qa-1)

(Qa-2)

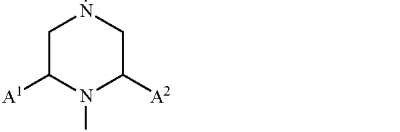

(Qa-3)

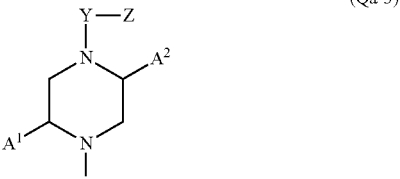

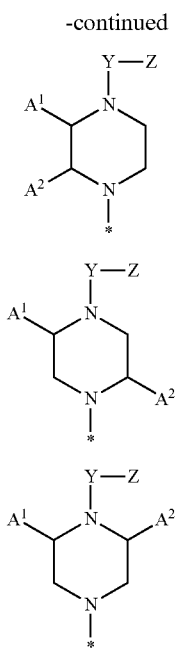

in which the asterisk (*) represents the point of attachment to the remainder of the molecule; and Y, Z, $A^1$ and $A^2$ are as defined above.

In a first embodiment, Q represents a group of formula (Qa-1) as defined above.

In a second embodiment, Q represents a group of formula (Qa-2) as defined above.

In a third embodiment, Q represents a group of formula (Qa-3) as defined above.

In a fourth embodiment, Q represents a group of formula (Qa-4) as defined above.

In a fifth embodiment, Q represents a group of formula (Qa-5) as defined above.

In a sixth embodiment, Q represents a group of formula (Qa-6) as defined above.

In one embodiment, V represents —$CH_2$— or —$C(CH_3)_2$—. In a first aspect of that embodiment, V represents —$CH_2$—. In a second aspect of that embodiment, V represents —$C(CH_3)_2$—. Where Q represents a group of formula (Qb) and V represents —$CH_2$— or —$C(CH_3)_2$—, the bicyclic moiety containing the integer V is a 2,5-diazabicyclo[2.2.1]-heptane ring system. Where Q represents a group of formula (Qc) or (Qd) and V represents —$CH_2$— or —$C(CH_3)_2$—, the bicyclic moiety containing the integer V is a 3,6-diazabicyclo[3.1.1]heptane ring system.

In another embodiment, V represents —$CH_2CH_2$—. Where Q represents a group of formula (Qb) and V represents —$CH_2CH_2$—, the bicyclic moiety containing the integer V is a 2,5-diazabicyclo[2.2.2]octane ring system. Where Q represents a group of formula (Qc) or (Qd) and V represents —$CH_2CH_2$—, the bicyclic moiety containing the integer V is a 3,8-diazabicyclo[3.2.1]octane ring system.

In a further embodiment, V represents —$CH_2CH_2CH_2$—. Where Q represents a group of formula (Qb) and V represents —$CH_2CH_2CH_2$—, the bicyclic moiety containing the integer V is a 6,8-diazabicyclo[3.2.2]nonane ring system. Where Q represents a group of formula (Qc) or (Qd) and V represents —$CH_2CH_2CH_2$—, the bicyclic moiety containing the integer V is a 7,9-diazabicyclo[3.3.1]nonane ring system.

Where Q represents a group of formula (Qe), the $C_{3-7}$ cycloalkyl group of which W is the residue is spiro-fused to the adjacent six-membered ring containing two nitrogen atoms. The cyclic group of which W is the residue is selected from cyclopropyl, cyclobutyl, cyclopentyl, cyclohexyl and cycloheptyl. Suitably, the cyclic group of which W is the residue is a $C_{4-6}$ cycloalkyl group. In a particular embodiment, the cyclic group of which W is the residue is cyclobutyl.

Generally, Y represents a covalent bond, or a linker group selected from —C(O)—, —S(O)—, —$S(O)_2$—, —C(O)O—, —C(O)N($R^4$)— and —$S(O)_2$N($R^4$)—, or a linker group of formula (Ya) as defined above.

Typically, Y represents a covalent bond, or a linker group selected from —C(O)—, —C(O)O— and —C(O)N($R^4$)—, or a linker group of formula (Ya) as defined above.

Suitably, Y represents a covalent bond, or a linker group selected from —C(O)— and —C(O)N($R^4$)—.

Appositely, Y represents a covalent bond, or a linker group selected from —C(O)—, —S(O)—, —$S(O)_2$—, —C(O)O—, —C(O)N($R^4$)— and —$S(O)_2$N($R^4$)—.

Suitable values of Y include —C(O)—, —S(O)—, —$S(O)_2$—, —C(O)O—, —C(O)N($R^4$)— and —$S(O)_2$N($R^4$)—.

Typical values of Y include —C(O)—, —C(O)N($R^4$)— and —C(O)C(O)—.

Selected values of Y include —C(O)— and —C(O)N($R^4$)—.

In a first embodiment, Y represents a covalent bond. In a second embodiment, Y represents —C(O)—. In a third embodiment, Y represents —S(O)—. In a fourth embodiment, Y represents —$S(O)_2$—. In a fifth embodiment, Y represents —C(O)O—. In a sixth embodiment, Y represents —C(O)N($R^4$)—. In a seventh embodiment, Y represents —C(O)C(O)—. In an eighth embodiment, Y represents —$S(O)_2$N($R^4$)—. In a ninth embodiment, Y represents a group of formula (Ya) as defined above.

Generally, Z represents hydrogen; or Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

Appositely, Z represents $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

Typically, Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

More typically, Z represents $C_{3-7}$ cycloalkyl, $C_{3-7}$ heterocycloalkyl, aryl or heteroaryl, any of which groups may be optionally substituted by one or more substituents.

Suitably, Z represents aryl or heteroaryl, either of which groups may be optionally substituted by one or more substituents.

In a first embodiment, Z represents hydrogen. In a second embodiment, Z represents optionally substituted $C_{1-6}$ alkyl. In a third embodiment, Z represents optionally substituted $C_{2-6}$ alkenyl. In a fourth embodiment, Z represents optionally substituted $C_{3-7}$ cycloalkyl. In a fifth embodiment, Z represents optionally substituted $C_{3-7}$ cycloalkyl($C_{1-6}$)alkyl. In a sixth embodiment, Z represents optionally substituted $C_{3-7}$ heterocycloalkyl. In a seventh embodiment, Z represents optionally substituted $C_{3-7}$ heterocycloalkyl($C_{1-6}$) alkyl. In an eighth embodiment, Z represents optionally substituted aryl. In a ninth embodiment, Z represents optionally substituted aryl($C_{1-6}$)alkyl. In a tenth embodiment, Z represents optionally substituted heteroaryl. In an eleventh embodiment, Z represents optionally substituted heteroaryl ($C_{1-6}$)alkyl.

In a particular embodiment, Z is other than hydrogen.

Typical values of Z include methyl, ethyl, isopropenyl, cyclopropyl, indanyl, cyclopropylmethyl, cyclopentylethyl, dihydrobenzofuranyl, pyrrolidinyl, indolinyl, dihydrobenzofuranylmethyl, morpholinylmethyl, morpholinylethyl, phenyl, benzyl, phenylethyl, furyl, benzofuryl, thienyl, indolyl, pyrazolyl, indazolyl, isoxazolyl, thiazolyl, benzothiazolyl, imidazolyl, benzimidazolyl, imidazo[1,2-a]pyridinyl, benzothiadiazolyl, pyridinyl, quinolinyl, isoquinolinyl, pyridazinyl, pyrimidinyl, pyrazinyl, quinoxalinyl, indolylmethyl, thiazolylmethyl, imidazo[2,1-b]thiazolylmethyl, pyridinylmethyl, furylethyl, benzimidazolylethyl and pyridinylethyl, any of which groups may be optionally substituted by one or more substituents.

Suitable values of Z include phenyl and pyridinyl, any of which groups may be optionally substituted by one or more substituents.

In one embodiment, Z is unsubstituted. In another embodiment, Z is substituted by one or more substituents, typically by one, two or three substituents, suitably by one or two substituents. In one aspect of that embodiment, Z is monosubstituted. In another aspect of that embodiment, Z is disubstituted. In a further aspect of that embodiment, Z is trisubstituted.

Typical examples of optional substituents on Z include one or more substituents independently selected from halogen, cyano, nitro, $C_{1-6}$ alkyl, trifluoromethyl, cyano-($C_{1-6}$) alkyl, ($C_{3-7}$)heterocycloalkyl, halo($C_{3-7}$)heterocycloalkyl, ($C_{1-6}$)alkyl($C_{3-7}$)heterocycloalkyl, ($C_{2-6}$)alkoxycarbonyl ($C_{3-7}$)heterocycloalkyl, dihalo($C_{3-7}$)heterocycloalkyl, ($C_{3-7}$) heterocycloalkyl($C_{1-6}$)alkyl, ($C_{1-6}$)alkyl($C_{3-7}$)heterocycloalkyl($C_{1-6}$)alkyl, heteroaryl, hydroxy, oxo, $C_{1-6}$ alkoxy, difluoromethoxy, trifluoromethoxy, trifluoroethoxy ($C_{3-7}$) heterocycloalkoxy, ($C_{2-6}$)alkoxycarbonyl($C_{3-7}$)heterocycloalkoxy, ($C_{3-7}$)heterocycloalkyl($C_{1-6}$)alkoxy, aryloxy, haloaryloxy, ($C_{1-6}$)alkoxyaryloxy, $C_{1-3}$ alkylenedioxy, dihalo($C_{1-3}$)alkylenedioxy, arylcarbonyloxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)-alkylamino($C_{1-6}$)alkyl, arylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aryloxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on Z include one or more substituents independently selected from halogen, $C_{1-6}$ alkyl, trifluoromethyl, ($C_{3-7}$)heterocycloalkyl, dihalo($C_{3-7}$)heterocycloalkyl, $C_{1-6}$ alkoxy, difluoromethoxy and trifluoromethoxy.

Suitable examples of optional substituents on Z include one or more substituents independently selected from $C_{1-6}$ alkyl, dihalo($C_{3-7}$)heterocycloalkyl, $C_{1-6}$ alkoxy, difluoromethoxy and trifluoromethoxy.

Typical examples of specific substituents on Z include fluoro, chloro, bromo, cyano, nitro, methyl, ethyl, isopropyl, tert-butyl, trifluoromethyl, cyanomethyl, azetidinyl, pyrrolidinyl, piperazinyl, morpholinyl, fluoroazetidinyl, fluoropyrrolidinyl, methylpiperazinyl, tert-butoxycarbonylpiperazinyl, difluoroazetidinyl, difluoropyrrolidinyl, difluoropiperidinyl, pyrrolidinylmethyl, piperidinylmethyl, morpholinylmethyl, methyl-piperazinylmethyl, pyrazolyl, imidazolyl, hydroxy, oxo, methoxy, ethoxy, isopropoxy, difluoromethoxy, trifluoromethoxy, trifluoroethoxy, oxetanyloxy, azetidinyloxy, tetrahydrofuranyloxy, pyrrolidinyloxy, tert-butoxycarbonylazetidinyloxy, tert-butoxycarbonylpyrrolidinyloxy, tetrahydrofuranylmethoxy, morpholinylethoxy, phenoxy, chlorophenoxy, methoxyphenoxy, methylenedioxy, ethylenedioxy, difluoromethylenedioxy, benzoyloxy, methylthio, methylsulfinyl, methylsulfonyl, amino, methylamino, tert-butylamino, dimethylamino, dimethylaminomethyl, phenylamino, acetylamino, methoxycarbonylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, ethoxycarbonyl, tert-butoxycarbonyl, benzyloxycarbonyl aminocarbonyl, methylaminocarbonyl, dimethylaminocarbonyl, aminosulfonyl, methylaminosulfonyl and dimethylaminosulfonyl.

Typical examples of specific substituents on Z include chloro, methyl, trifluoromethyl, azetidinyl, difluoroazetidinyl, methoxy, ethoxy, difluoromethoxy and trifluoromethoxy.

Suitable examples of specific substituents on Z include methyl, difluoroazetidinyl, methoxy, ethoxy, difluoromethoxy and trifluoromethoxy.

Selected values of Z include include phenoxymethyl, chlorophenoxymethyl, methoxyphenoxymethyl, tert-butoxycarbonylmethyl, benzyloxycarbonylmethyl, phenoxyethyl, isopropenyl, cyclopropyl, indanyl, cyclopropylmethyl, cyclopentylethyl, (methyl)(oxo)pyrrolidinyl, dihydrobenzofuranyl, methylindolinyl, dihydrobenzofuranylmethyl, morpholinylmethyl, morpholinylethyl, phenyl, nitrophenyl, methylphenyl, ethylphenyl, cyanomethylphenyl, morpholinylphenyl, pyrazolylphenyl, imidazolylphenyl, methoxyphenyl, difluoromethoxyphenyl, trifluoromethoxyphenyl, morpholinylethoxy-phenyl, ethylenedioxyphenyl, difluoromethylenedioxyphenyl, benzoyloxyphenyl, dimethylaminophenyl, acetylaminophenyl, aminocarbonylphenyl, (chloro)(methyl)-phenyl, dimethylphenyl, (methyl)(trifluoromethyl)phenyl, bis(trifluoromethyl)phenyl, (fluoropyrrolidinyl)(methyl)phenyl, (methyl) (pyrrolidinylmethyl)phenyl, (methyl)-(morpholinylmethyl) phenyl, (methyl)(methylpiperazinylmethyl)phenyl, (fluoro)- (methoxy)phenyl, (chloro)(methoxy)phenyl, (cyano) (methoxy)phenyl, (methoxy)-(methyl)phenyl, (methoxy) (trifluoromethyl)phenyl, dimethoxyphenyl, (difluoromethoxy)-(methyl)phenyl, (methyl)(trifluoromethoxy)phenyl, (methyl)(oxetanyloxy)phenyl, (azetidinyloxy)(methyl)phenyl, (tert-butoxycarbonylazetidinyloxy) (methyl)phenyl, (methyl)(tetrahydrofuranylmethoxy) phenyl, (methyl)(morpholinylethoxy)phenyl, (dimethylaminomethyl)(methyl)phenyl, trimethoxyphenyl, benzyl, cyanobenzyl, methylbenzyl, methoxybenzyl, methylenedioxybenzyl, dimethylaminobenzyl, dimethoxy-benzyl, phenylethyl, fluorophenylethyl, methylphenylethyl, (hydroxy)(phenyl)ethyl, methoxyphenylethyl, methylfuryl, methoxybenzofuryl, thienyl, indolyl, methylindolyl, pyrazolyl, methylpyrazolyl, dimethylpyrazolyl, indazolyl, methylindazolyl, dimethyl-isoxazolyl, thiazolyl, methylthiazolyl, tert-butylthiazolyl, ethoxycarbonylthiazolyl, benzothiazolyl, methoxybenzothiazolyl, methylimidazolyl, benzimidazolyl, methyl-benzimidazolyl, trifluoromethylbenzimidazolyl, piperidinylmethylbenzimidazolyl, morpholinylmethylbenzimidazolyl, imidazo[1,2-a]pyridinyl, benzothiadiazolyl, pyridinyl, chloropyridinyl, methylpiperazinylpyridinyl, methoxypyridinyl, dimethylpyridinyl, (methyl)(trifluoromethyl)pyridinyl, (azetidinyl)(methyl)pyridinyl, (methyl)(pyrrolidinyl)-pyridinyl, (methyl)(piperazinyl)pyridinyl, (fluoroazetidinyl)(methyl)pyridinyl, (fluoropyrrolidinyl)(methyl)pyridinyl, (methyl)(methylpiperazinyl)pyridinyl, (tert-butoxycarbonylpiperazinyl)(methyl)pyridinyl, (difluoroazetidinyl)(methyl)pyridinyl, (difluoropyrrolidinyl)(methyl)pyridinyl, (difluoropiperidinyl)(methyl)pyridinyl, (methyl)-(pyrrolidinylmethyl)pyridinyl, (methyl)(morpholinylmethyl)pyridinyl, (methyl)(methylpiperazinylmethyl)pyridinyl, (hydroxy)(methyl)pyridinyl, (dimethyl)(oxo)pyridinyl, (chloro)(methoxy)pyridinyl, (methoxy)(methyl)pyridinyl, (methoxy)(trifluoromethyl)pyridinyl, dimethoxypyridinyl, (ethoxy)(methyl)pyridinyl, (isopropoxy)(methyl)pyridinyl, (difluoromethoxy)(methyl)pyridinyl, (methyl)(trifluoroethoxy)pyridinyl, (methyl)-(tetrahydrofuranyloxy)pyridinyl, (methyl)(pyrrolidinyloxy)pyridinyl, (tert-butoxy-carbonylazetidinyloxy)(methyl)pyridinyl, (tert-butoxycarbonylpyrrolidinyloxy)(methyl)-pyridinyl, (methyl)(methylamino)pyridinyl, (dimethylamino)(methyl)pyridinyl, quinolinyl, isoquinolinyl, methoxypyridazinyl, pyrimidinyl, (difluoroazetidinyl)(methyl)-pyrimidinyl, methoxypyrimidinyl, (methoxy)(methyl)pyrimidinyl, (dimethylamino)-(methyl)pyrimidinyl, pyrazinyl, methoxypyrazinyl, (methoxy)(methyl)pyrazinyl, quinoxalinyl, indolylmethyl, thiazolylmethyl, methylthiazolylmethyl, imidazo[2,1-b]-thiazolylmethyl, pyridinylmethyl, furylethyl, benzimidazolylethyl and pyridinylethyl. Additional values include (chloro)(trifluoromethoxy)phenyl.

Illustrative values of Z include (methoxy)(methyl)phenyl, (difluoromethoxy)(methyl)phenyl, (chloro)(trifluoromethoxy)phenyl, (methyl)-(trifluoromethoxy)phenyl, (azetidinyl)(methyl)pyridinyl, (difluoroazetidinyl)(methyl)-pyridinyl, (methoxy)(methyl)pyridinyl, (methoxy)(trifluoromethyl)pyridinyl, dimethoxypyridinyl and (ethoxy)(methyl)pyridinyl.

Typical values of Z include (methoxy)(methyl)phenyl, (difluoromethoxy)-(methyl)phenyl, (methyl)(trifluoromethoxy)phenyl, (difluoroazetidinyl)(methyl)pyridinyl, (methoxy)(methyl)pyridinyl and (ethoxy)(methyl)pyridinyl.

In a first embodiment, Z represents (methoxy)(methyl) phenyl. In a first aspect of that embodiment, Z represents 4-methoxy-2-methylphenyl. In a second aspect of that embodiment, Z represents 4-methoxy-3-methylphenyl.

In a second embodiment, Z represents (difluoromethoxy)(methyl)phenyl, especially 4-(difluoromethoxy)-2-methylphenyl.

In a third embodiment, Z represents (methyl)(trifluoromethoxy)phenyl, especially 2-methyl-4-(trifluoromethoxy)phenyl.

In a fourth embodiment, Z represents (difluoroazetidinyl)(methyl)pyridinyl, especially 6-(3,3-difluoroazetidin-1-yl)-2-methylpyridin-3-yl.

In a fifth embodiment, Z represents (methoxy)(methyl)pyridinyl. In a first aspect of that embodiment, Z represents 6-methoxy-2-methylpyridin-3-yl. In a second aspect of that embodiment, Z represents 6-methoxy-5-methylpyridin-3-yl.

In a sixth embodiment, Z represents dimethoxypyridinyl, especially 2,6-dimethoxypyridin-3-yl.

In a seventh embodiment, Z represents (ethoxy)(methyl)pyridinyl, especially 6-ethoxy-2-methylpyridin-3-yl.

In an eighth embodiment, Z represents (chloro)(trifluoromethoxy)phenyl, especially 2-chloro-4-(trifluoromethoxy)phenyl.

In a ninth embodiment, Z represents (azetidinyl)(methyl) pyridinyl, especially 6-(azetidin-1-yl)-2-methylpyridin-3-yl.

In a tenth embodiment, Z represents (methoxy)(trifluoromethyl)pyridinyl, especially 5-methoxy-6-(trifluoromethyl)pyridin-2-yl.

Generally, $A^1$ represents hydrogen, cyano or trifluoromethyl; or $A^1$ represents $C_{1-6}$ alkyl, optionally substituted by one or more substituents independently selected from —$OR^a$, —$NR^bR^c$, —$CO_2R^d$ and —$CONR^bR^c$; or $A^1$ represents $C_{3-7}$ cycloalkyl.

Typically, $A^1$ represents hydrogen or cyano; or $A^1$ represents $C_{1-6}$ alkyl, optionally substituted by one or more substituents independently selected from —$OR^a$, —$CO_2R^d$ and —$CONR^bR^c$; or $A^1$ represents $C_{3-7}$ cycloalkyl.

Suitably, $A^1$ represents hydrogen; or $A^1$ represents $C_{1-6}$ alkyl, optionally substituted by —$OR^a$.

In a first embodiment, $A^1$ represents hydrogen. In a second embodiment, $A^1$ represents cyano. In a third embodiment, $A^1$ represents trifluoromethyl. In a fourth embodiment, $A^1$ represents $C_{1-6}$ alkyl, optionally substituted by one or more substituents independently selected from fluoro, —$OR^a$, trifluoromethoxy, —$NR^bR^c$, —$CO_2R^d$ and —$CONR^bR^c$. In a first aspect of that embodiment, $A^1$ represents $C_{1-6}$ alkyl, optionally substituted by one or more substituents independently selected from —$OR^a$, —$NR^bR^c$, —$CO_2R^d$ and —$CONR^bR^c$. In a second aspect of that embodiment, $A^1$ represents $C_{1-6}$ alkyl, optionally substituted by one or more substituents independently selected from —$OR^a$, —$CO_2R^d$ and —$CONR^bR^c$. In a third aspect of that embodiment, $A^1$ represents $C_{1-6}$ alkyl, optionally substituted by one or more substituents independently selected from —$OR^a$ and —$NR^bR^c$. In a fourth aspect of that embodiment, $A^1$ represents unsubstituted $C_{1-6}$ alkyl, typically methyl, ethyl, isopropyl or isobutyl, especially methyl or ethyl. In a fifth aspect of that embodiment, $A^1$ represents $C_{1-6}$ alkyl monosubstituted by —$OR^a$, —$CO_2R^d$ or —$CONR^bR^c$. In a sixth aspect of that embodiment, $A^1$ represents $C_{1-6}$ alkyl monosubstituted by —$OR^a$ or —$NR^bR^c$. In a seventh aspect of that embodiment, A represents $C_{1-6}$ alkyl monosubstituted by —$OR^a$, especially hydroxyethyl. In an eighth aspect of that embodiment, $A^1$ represents $C_{1-6}$ alkyl disubstituted by two substituents independently selected from —$OR^a$ and —$NR^bR^c$. In a fifth embodiment, $A^1$ represents $C_{3-7}$ cycloalkyl, especially cyclopropyl.

Selected values of $A^1$ include hydrogen, cyano, methyl, ethyl, isopropyl, isobutyl, —$CH_2OR^a$, —$CH_2CH_2OR^a$, —$CH_2CO_2R^d$, —$CH_2CONR^bR^c$ and cyclopropyl.

Illustrative values of $A^1$ include hydrogen, methyl, ethyl and —$CH_2CH_2OR^a$.

Particular values of $A^1$ include hydrogen, methyl, ethyl and hydroxyethyl.

Apposite values of $A^1$ include hydrogen, methyl and ethyl.

Suitable values of $A^1$ include methyl and ethyl.

A first particular value of $A^1$ is hydrogen.

A second particular value of $A^1$ is methyl.

A third particular value of $A^1$ is ethyl.

A fourth particular value of $A^1$ is hydroxyethyl, especially 2-hydroxyethyl.

In a particular embodiment, $A^2$ represents hydrogen. In another embodiment, $A^2$ represents $C_{1-6}$ alkyl, especially methyl.

Selected values of $A^2$ include hydrogen and methyl.

Suitably, $R^1$ represents hydrogen, halogen, cyano, nitro, hydroxy, trifluoromethyl, trifluoromethoxy, —$OR^a$, —$SR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —NR$^c$SO$_2$R$^e$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or R$^1$ represents C$_{1-6}$ alkyl, aryl or heteroaryl, any of which groups may be optionally substituted by one or more substituents.

Typically, R$^1$ represents hydrogen, —OR$^a$, —SR$^a$, —SO$_2$R$^a$, —NR$^b$R$^c$ or —NR$^c$COR$^d$; or R$^1$ represents C$_{1-6}$ alkyl, which group may be optionally substituted by one or more substituents.

Typical values of R$^1$ include hydrogen, —OR$^a$, —SR$^a$, —SO$_2$R$^a$ and —NR$^b$R$^c$.

Suitable values of R$^1$ include hydrogen and —NR$^b$R$^c$.

In a first embodiment, R$^1$ represents hydrogen. In a second embodiment, R$^1$ represents cyano. In a third embodiment, R$^1$ represents —OR$^a$. In a fourth embodiment, R$^1$ represents —SR$^a$. In a fifth embodiment, R$^1$ represents —SO$_2$R$^a$. In a sixth embodiment, R$^1$ represents —NR$^b$R$^c$. In a seventh embodiment, R$^1$ represents —NR$^c$COR$^d$. In an eighth embodiment, R$^1$ represents optionally substituted C$_{1-6}$ alkyl. In one aspect of that embodiment, R$^1$ represents optionally substituted methyl.

Examples of typical substituents on R$^1$ include one or more substituents independently selected from halogen, cyano, nitro, C$_{1-6}$ alkyl, trifluoromethyl, aryl(C$_{1-6}$)alkyl, hydroxy, C$_{1-6}$ alkoxy, difluoromethoxy, trifluoromethoxy, aryloxy, C$_{1-4}$ alkylenedioxy, C$_{1-6}$ alkoxy(C$_{1-6}$)alkyl, C$_{1-6}$ alkylthio, C$_{1-6}$ alkylsulphonyl, oxo, amino, C$_{1-6}$ alkylamino, di(C$_{1-6}$)alkylamino, C$_{2-6}$ alkylcarbonylamino, C$_{2-6}$ alkoxycarbonylamino, aryl(C$_{1-6}$)alkoxycarbonylamino, C$_{1-6}$ alkylaminocarbonylamino, arylaminocarbonylamino, C$_{1-6}$ alkylsulphonylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulphonyl, C$_{1-6}$ alkylaminosulphonyl and di(C$_{1-6}$)alkylaminosulphonyl.

Specific examples of typical substituents on R$^1$ include one or more substituents independently selected from fluoro, chloro, bromo, cyano, nitro, methyl, ethyl, tert-butyl, trifluoromethyl, benzyl, hydroxy, methoxy, difluoromethoxy, trifluoromethoxy, phenoxy, methylenedioxy, ethylenedioxy, methoxymethyl, methylthio, methylsulphonyl, oxo, amino, methylamino, dimethylamino, acetylamino, methoxycarbonylamino, ethoxycarbonylamino, benzyloxycarbonylamino, ethylaminocarbonylamino, butylaminocarbonylamino, phenylaminocarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

Generally, R$^2$ represents hydrogen, cyano, hydroxy, trifluoromethyl, —NR$^c$CO$_2$R$^d$, —COR$^d$, —CO$_2$R$^d$, —CONR$^b$R$^c$ or —CON(OR$^a$)R$^b$; or R$^2$ represents C$_{1-6}$ alkyl, C$_{3-7}$ cycloalkyl, aryl, C$_{3-7}$ heterocycloalkyl, C$_{3-7}$ heterocycloalkenyl or heteroaryl, any of which groups may be optionally substituted by one or more substituents.

Typically, R$^2$ represents hydrogen, —CO$_2$R$^d$, —CONR$^b$R$^c$ or —CON(OR$^a$)R$^b$; or R$^2$ represents C$_{1-6}$ alkyl, aryl or C$_{3-7}$ heterocycloalkenyl, any of which groups may be optionally substituted by one or more substituents.

Suitably, R$^2$ represents hydrogen; or R$^2$ represents C$_{1-6}$ alkyl or aryl, either of which groups may be optionally substituted by one or more substituents.

In a first embodiment, R$^2$ represents hydrogen. In a second embodiment, R$^2$ represents cyano. In a third embodiment, R$^2$ represents hydroxy. In a fourth embodiment, R$^2$ represents trifluoromethyl. In a fifth embodiment, R$^2$ represents —NR$^c$CO$_2$R$^d$. In a sixth embodiment, R$^2$ represents —COR$^d$. In a seventh embodiment, R$^2$ represents —CO$_2$R$^d$. In an eighth embodiment, R$^2$ represents —CONR$^b$R$^c$. In a ninth embodiment, R$^2$ represents —CON(OR$^a$)R$^b$. In a tenth embodiment, R$^2$ represents optionally substituted C$_{1-6}$ alkyl. In a first aspect of that embodiment, R$^2$ represents unsubstituted C$_{1-6}$ alkyl. In a second aspect of that embodiment, R$^2$ represents monosubstituted C$_{1-6}$ alkyl. In a third aspect of that embodiment, R$^2$ represents disubstituted C$_{1-6}$ alkyl. In an eleventh embodiment, R$^2$ represents optionally substituted C$_{3-7}$ cycloalkyl. In a first aspect of that embodiment, R$^2$ represents unsubstituted C$_{3-7}$ cycloalkyl. In a second aspect of that embodiment, R$^2$ represents monosubstituted C$_{3-7}$ cycloalkyl. In a third aspect of that embodiment, R$^2$ represents disubstituted C$_{3-7}$ cycloalkyl. In a twelfth embodiment, R$^2$ represents optionally substituted aryl. In a first aspect of that embodiment, R$^2$ represents unsubstituted aryl. In a second aspect of that embodiment, R$^2$ represents monosubstituted aryl. In a third aspect of that embodiment, R$^2$ represents disubstituted aryl. In a thirteenth embodiment, R$^2$ represents optionally substituted C$_{3-7}$ heterocycloalkyl. In a first aspect of that embodiment, R$^2$ represents unsubstituted C$_{3-7}$ heterocycloalkyl. In a second aspect of that embodiment, R$^2$ represents monosubstituted C$_{3-7}$ heterocycloalkyl. In a third aspect of that embodiment, R$^2$ represents disubstituted C$_{3-7}$ heterocycloalkyl. In a fourteenth embodiment, R$^2$ represents optionally substituted C$_{3-7}$ heterocycloalkenyl. In a first aspect of that embodiment, R$^2$ represents unsubstituted C$_{3-7}$ heterocycloalkenyl. In a second aspect of that embodiment, R$^2$ represents monosubstituted C$_{3-7}$ heterocycloalkenyl. In a third aspect of that embodiment, R$^2$ represents disubstituted C$_{3-7}$ heterocycloalkenyl. In a fifteenth embodiment, R$^2$ represents optionally substituted heteroaryl. In a first aspect of that embodiment, R$^2$ represents unsubstituted heteroaryl. In a second aspect of that embodiment, R$^2$ represents monosubstituted heteroaryl. In a third aspect of that embodiment, R$^2$ represents disubstituted heteroaryl.

Where R$^2$ represents optionally substituted C$_{1-6}$ alkyl, suitable values include methyl, ethyl, n-propyl, isopropyl, n-butyl, isobutyl and tert-butyl, any of which groups may be optionally substituted by one or more substituents. Selected values include methyl, hydroxymethyl, chloropropyl and isobutyl. Particular values include methyl and isobutyl, especially methyl.

Where R$^2$ represents optionally substituted C$_{3-7}$ cycloalkyl, a suitable value is cyclohexyl, optionally substituted by one or more substituents.

Where R$^2$ represents optionally substituted aryl, a suitable value is phenyl, optionally substituted by one or more substituents. Selected values include phenyl, fluorophenyl, chlorophenyl and methoxyphenyl. A particular value is fluorophenyl.

Where R$^2$ represents optionally substituted C$_{3-7}$ heterocycloalkyl, typical values include azetidinyl, pyrrolidinyl, piperidinyl, piperazinyl, morpholinyl and thiomorpholinyl, any of which groups may be optionally substituted by one or more substituents.

Where R$^2$ represents optionally substituted C$_{3-7}$ heterocycloalkenyl, a typical value is oxazolinyl, optionally substituted by one or more substituents. Suitable values include oxazolinyl, methyloxazolinyl, isopropyloxazolinyl and dimethyloxazolinyl.

Where R$^2$ represents optionally substituted heteroaryl, typical values include pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl, any of which groups may be optionally substituted by one or more substituents. Suitable values include oxadiazolyl and pyridinyl, either of which groups may be optionally substituted by one or more substituents. Selected values include methyloxadiazolyl, isopropyloxadiazolyl, tert-butyloxadiazolyl and pyridinyl.

In a selected embodiment, $R^2$ represents hydrogen, cyano, hydroxy, trifluoro-methyl, —$NR^cCO_2R^d$, —$COR^d$, —$CO_2R^d$, —$CONR^bR^c$ or —$CON(OR^a)R^b$; or $R^2$ represents $C_{1-6}$ alkyl, cyclohexyl, phenyl, oxazolinyl, oxadiazolyl or pyridinyl, any of which groups may be optionally substituted by one or more substituents.

In a typical embodiment, $R^2$ represents hydrogen; or $R^2$ represents $C_{1-6}$ alkyl or phenyl, either of which groups may be optionally substituted by one or more substituents.

Typical examples of optional substituents on $R^2$ include one or more substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$) alkylaminosulfonyl.

Suitable examples of optional substituents on $R^2$ include one or more substituents independently selected from halogen.

Typical examples of specific substituents on $R^2$ include one or more substituents independently selected from fluoro, chloro, bromo, cyano, nitro, methyl, ethyl, isopropyl, tert-butyl, trifluoromethyl, hydroxy, methoxy, isopropoxy, difluoromethoxy, trifluoro-methoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl and dimethylaminosulfonyl.

Suitable examples of specific substituents on $R^2$ include one or more substituents independently selected from fluoro.

Typical values of $R^2$ include hydrogen, cyano, hydroxy, trifluoromethyl, —$NR^cCO_2R^d$, —$COR^d$, —$CO_2R^d$, —$CONR^bR^c$, —$CON(OR^a)R^b$, methyl, hydroxymethyl, chloropropyl, isobutyl, cyclohexyl, phenyl, fluorophenyl, chlorophenyl, methoxyphenyl, oxazolinyl, methyloxazolinyl, isopropyloxazolinyl, dimethyloxazolinyl, methyloxadiazolyl, isopropyloxadiazolyl, tert-butyloxadiazolyl and pyridinyl.

Suitable values of $R^2$ include hydrogen, methyl and fluorophenyl.

Typically, $R^3$ represents hydrogen or $C_{1-6}$ alkyl.

In a first embodiment, $R^3$ represents hydrogen. In a second embodiment, $R^3$ represents halogen, especially fluoro or chloro. In a first aspect of that embodiment, $R^3$ represents fluoro. In a second aspect of that embodiment, $R^3$ represents chloro. In a third embodiment, $R^3$ represents $C_{1-6}$ alkyl, especially methyl.

Typical values of $R^3$ include hydrogen, chloro and methyl.

Suitable values of $R^3$ include hydrogen and methyl.

Suitably, $R^4$ represents hydrogen or $C_{1-6}$ alkyl.

Suitable values of $R^4$ include hydrogen and methyl.

In one embodiment, $R^4$ represents hydrogen. In another embodiment, $R^4$ represents $C_{1-6}$ alkyl, optionally substituted by one or more substituents independently selected from —$OR^a$ and —$NR^bR^c$. In one aspect of that embodiment, $R^4$ represents unsubstituted $C_{1-6}$ alkyl, especially methyl. In another aspect of that embodiment, $R^4$ represents $C_{1-6}$ alkyl monosubstituted by —$OR^a$ or —$NR^bR^c$. In a further aspect of that embodiment, $R^4$ represents $C_{1-6}$ alkyl disubstituted by two substituents independently selected from —$OR^a$ and —$NR^bR^c$.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, acetylaminomethyl, tert-butoxycarbonylamino, methylsulphonylamino, aminocarbonyl, methylaminocarbonyl and dimethylaminocarbonyl.

Typically, $R^a$ represents hydrogen; or $R^a$ represents $C_{1-6}$ alkyl, aryl($C_{1-6}$)alkyl or heteroaryl($C_{1-6}$)alkyl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Apposite values of $R^a$ include hydrogen; and methyl, ethyl, benzyl or isoindolylpropyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents hydrogen. In another embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$) alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

Appositely, $R^a$ represents hydrogen or $C_{1-6}$ alkyl.

Individual values of $R^a$ include hydrogen and methyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl or ethyl, particularly methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, ethyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Appositely, $R^d$ represents hydrogen or $C_{1-6}$ alkyl.

Individual values of $R^d$ include hydrogen, methyl and ethyl.

A particular value of $R^d$ is ethyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA), and pharmaceutically acceptable salts and solvates thereof:

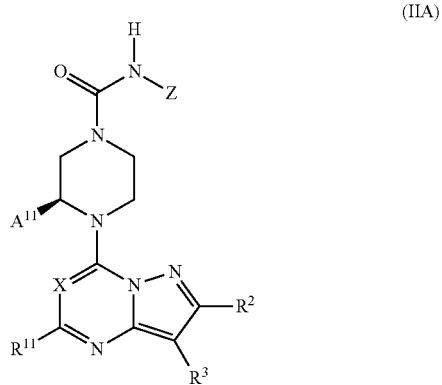

(IIA)

wherein $A^{11}$ represents hydrogen, cyano, $C_{1-6}$ alkyl, —$CH_2OR^a$, —$CH_2CH_2OR^a$, —$CH_2CO_2R^d$, —$CH_2CONR^bR^c$ or $C_{3-7}$ cycloalkyl;

$R^{11}$ represents hydrogen or amino; and

X, Z, $R^2$, $R^3$, $R^a$, $R^b$, $R^c$ and $R^d$ are as defined above.

In a first embodiment, $A^{11}$ represents hydrogen. In a second embodiment, $A^{11}$ represents cyano. In a third embodiment, $A^{11}$ represents $C_{1-6}$ alkyl, typically methyl, ethyl, isopropyl or isobutyl, especially methyl or ethyl. In a fourth embodiment, $A^{11}$ represents —$CH_2OR^a$. In a fifth embodiment, $A^{11}$ represents —$CH_2CH_2OR^a$. In a sixth embodiment, $A^{11}$ represents —$CH_2CO_2R^d$. In a seventh embodiment, $A^{11}$ represents —$CH_2CONR^bR^c$. In an eighth embodiment, $A^{11}$ represents $C_{3-7}$ cycloalkyl, especially cyclopropyl.

Selected values of $A^{11}$ include hydrogen, cyano, methyl, ethyl, isopropyl, isobutyl, —$CH_2OR^a$, —$CH_2CH_2OR^a$, —$CH_2CO_2R^d$, —$CH_2CONR^bR^c$ and cyclopropyl.

Illustrative values of $A^{11}$ include hydrogen, methyl, ethyl and —$CH_2CH_2OR^a$.

Particular values of $A^{11}$ include hydrogen, methyl, ethyl and 2-hydroxyethyl.

Apposite values of $A^{11}$ include hydrogen, methyl and ethyl.

Suitable values of $A^{11}$ include methyl and ethyl.

A first particular value of $A^{11}$ is hydrogen.

A second particular value of $A^{11}$ is methyl.

A third particular value of $A^{11}$ is ethyl.

A fourth particular value of $A^{11}$ is 2-hydroxyethyl.

In a first embodiment, $R^{11}$ is hydrogen. In a second embodiment, $R^{11}$ is —$NH_2$.

Another sub-class of compounds according to the invention is represented by the compounds of formula (IIB), and pharmaceutically acceptable salts and solvates thereof:

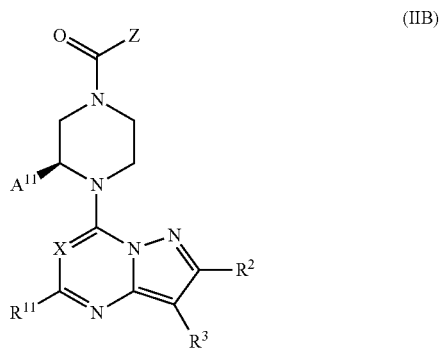

(IIB)

wherein X, Z, $A^{11}$, $R^2$, $R^3$ and $R^{11}$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments. These include inflammatory, autoimmune and oncological disorders; viral diseases and malaria; and organ and cell transplant rejection.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis and spontaneous infertility.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

Viral diseases include infections caused by various families of virus, including the Retroviridae, Flaviviridae, Picornaviridae. Various genera within the Retroviridae family include *Alpharetrovirus, Betaretrovirus, Gammaretrovirus, Deltaretrovirus, Epsilonretrovirus, Lentivirus* and *Spumavirus*. Members of the *Lentivirus* genus include human immunodeficiency virus 1 (HIV-1) and human immunodeficiency virus 2 (HIV-2). Various genera within the Flaviviridae family include *Flavivirus, Pestivirus, Hepacivirus* and *Hepatitis G Virus*. Members of the *Flavivirus* genus include Dengue fever virus, yellow fever virus, West Nile encephalitis virus and Japanese encephalitis virus. Members of the *Pestivirus* genus include bovine viral diarrhoea virus (BVDV), classical swine fever virus and border disease virus 2 (BDV-2). Members of the *Hepacivirus* genus include hepatitis C virus (HCV). Members of the *Hepatitis G Virus* genus include hepatitis G virus. Various genera within the Picornaviridae family include *Aphthovirus, Avihepatovirus, Cardiovirus, Enterovirus, Erbovirus, Hepatovirus, Kobuvirus, Parechovirus, Sapelovirus, Senecavirus, Teschovirus* and *Tremovirus*. Members of the *Enterovirus* genus include poliovirus, coxsackie A virus, coxsackie B virus and rhinovirus.

Organ transplant rejection includes the rejection of transplanted or grafted organs or cells (both allografts and xenografts), including graft-versus-host reaction disease. The term "organ" as used herein means all organs or parts of organs in mammals, particularly humans, including kidney, lung, bone marrow, hair, cornea, eye (vitreous), heart, heart valve, liver, pancreas, blood vessel, skin, muscle, bone, intestine and stomach. The term "rejection" as used herein means all reactions of the recipient body or the transplanted organ which ultimately lead to cell or tissue death in the transplanted organ, or adversely affect the functional ability and viability of the transplanted organ or the recipient. In particular, this means acute and chronic rejection reactions.

Cell transplant rejection includes the rejection of cell transplants and xenotransplantation. The major hurdle for xenotransplantation is that even before the T lymphocytes (responsible for the rejection of allografts) are activated, the innate immune system (especially T-independent B lymphocytes and macrophages) is activated. This provokes two types of severe and early acute rejection, referred to as hyperacute rejection and vascular rejection respectively. Conventional immunosuppressant drugs, including cyclosporine A, are ineffective in xenotransplantation. The compounds in accordance with the present invention are not liable to this drawback. The ability of the compounds of this invention to suppress T-independent xeno-antibody production as well as macrophage activation may be demonstrated by their ability to prevent xenograft rejection in athymic, T-deficient mice receiving xenogenic hamster-heart grafts.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula Q-H with a compound of formula (III):

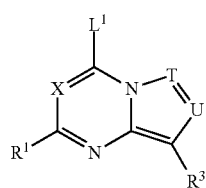

(III)

wherein X, T, U, Q, $R^1$ and $R^3$ are as defined above, and $L^1$ represents a suitable leaving group.

The leaving group $L^1$ is typically a halogen atom, e.g. chloro.

The reaction will generally be carried out in the presence of a base, typically an organic amine such as triethylamine or N,N-diisopropylethylamine. The reaction is conveniently effected at ambient or elevated temperature in a suitable solvent, e.g. a lower alkanol such as ethanol or n-butanol, a cyclic ether solvent such as tetrahydrofuran or 1,4-dioxane, or a dipolar aprotic solvent such as N,N-dimethylformamide.

Alternatively, the leaving group $L^1$ may be hydroxy (—OH), in which case the reaction may be accomplished at a suitable temperature (ambient or elevated) in a solvent such as acetonitrile or N,N-dimethylformamide, ideally in the presence of a coupling agent such as benzotriazol-1-yloxytris(dimethylamino)phosphonium hexafluorophosphate (BOP) or (benzotriazol-1-yloxy)tripyrrolidinophosphonium hexafluorophosphate (PyBOP), and a base, e.g. an organic base such as 1,8-diazabicyclo[5.4.0]undec-7-ene (DBU).

In another procedure, the compounds of formula (I) above wherein Y represents —C(O)—, —S(O)$_2$— or —C(O)O— may be prepared by a process which comprises reacting a compound of formula $L^2$-C(O)—Z, $L^2$-S(O)$_2$—Z or $L^2$-C(O)O—Z respectively with a compound of formula (IV-1), (IV-2), (IV-3), (IV-4) or (IV-5):

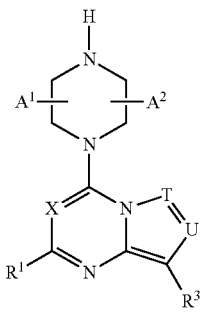

(IV-1)

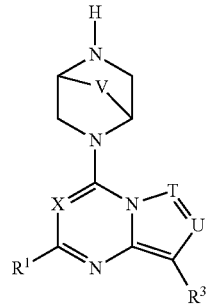

(IV-2)

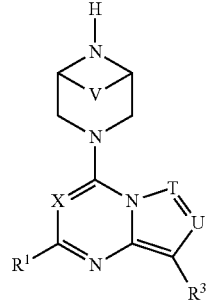

(IV-3)

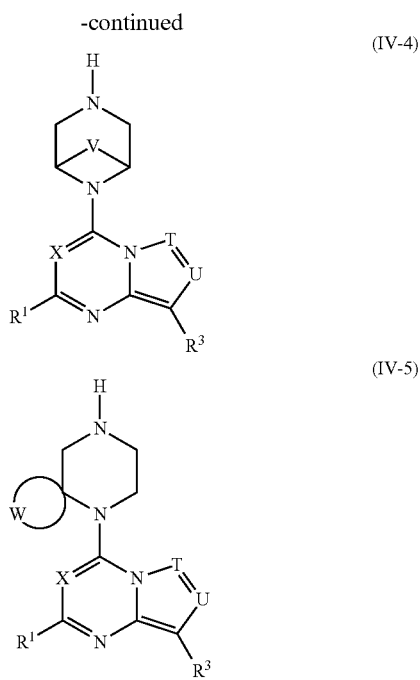

wherein X, T, U, V, W, Z, $A^1$, $A^2$, $R^1$ and $R^3$ are as defined above, and $L^2$ represents a suitable leaving group.

The leaving group $L^2$ is typically a halogen atom, e.g. chloro.

The reaction is conveniently effected at ambient temperature in a suitable solvent, e.g. an ethereal solvent such as 1,4-dioxane, or a chlorinated solvent such as dichloromethane, typically in the presence of a base. A suitable base for use in the reaction may be an organic base such as N,N-diisopropylethylamine, or an inorganic base such as potassium carbonate.

Alternatively, the leaving group $L^2$ may be 2-methyl-3-(trifluoromethylsulfonyl)-1H-imidazol-3-ium-1-yl, in which case the reaction may conveniently be effected at ambient temperature in an organic solvent such as acetonitrile.

In a variant procedure, the compounds of formula (I) above wherein Y represents —C(O)— may be prepared by a process which comprises reacting a compound of formula (IV-1), (IV-2), (IV-3), (IV-4) or (IV-5) as defined above with a compound of formula Z—CO₂H. Similarly, the compounds of formula (I) above wherein Y represents —C(O)C(O)— may be prepared by a process which comprises reacting a compound of formula (IV-1), (IV-2), (IV-3), (IV-4) or (IV-5) as defined above with a compound of formula Z—C(O)CO₂H.

The reaction is conveniently effected at ambient temperature in a suitable solvent, e.g. a dipolar aprotic solvent such as N,N-dimethylformamide, typically in the presence of a coupling reagent and a base. A suitable coupling reagent for use in the reaction may be O-(7-azabenzotriazol-1-yl)-N,N,N',N'-tetramethyluronium hexafluorophosphate (HATU). A suitable base for use in the reaction may be an organic base such as N,N-diisopropylethylamine.

In another procedure, the compounds of formula (I) above wherein Y represents —C(O)NH— may be prepared by a process which comprises reacting a compound of formula (IV-1), (IV-2), (IV-3), (IV-4) or (IV-5) as defined above with an isocyanate derivative of formula Z—N=C=O, wherein Z is as defined above.

The reaction is conveniently effected at a suitable temperature, e.g. ambient temperature or a temperature in the region of 0° C., in a suitable solvent or mixture of solvents. Such solvent or solvents may typically be selected as appropriate from an ethereal solvent such as 1,4-dioxane or tetrahydrofuran, a chlorinated solvent such as dichloromethane, a nitrile-containing solvent such as acetonitrile, and a dipolar aprotic solvent such as N,N-dimethylformamide. The reaction may optionally be performed in the presence of a base, e.g. an organic base such as diisopropylamine, N,N-diisopropylethylamine or triethylamine.

Alternatively, the compounds of formula (I) above wherein Y represents —C(O)NH— may be prepared by a process which comprises reacting a compound of formula (IV-1), (IV-2), (IV-3), (IV-4) or (IV-5) as defined above with a compound of formula Z—NH₂, wherein Z is as defined above, in the presence of triphosgene or 1,1'-carbonyldiimidazole.

The reaction is conveniently effected at ambient temperature in a suitable solvent, e.g. a chlorinated solvent such as dichloromethane, or a dipolar aprotic solvent such as N,N-dimethylformamide, typically in the presence of a base, e.g. an organic base such as N,N-diisopropylethylamine.

Alternatively, the compounds of formula (I) above wherein Y represents —C(O)NH— may be prepared by a two-step process which comprises: (i) reacting a compound of formula Z—NH₂, wherein Z is as defined above, with phenyl chloroformate or 4-nitrophenyl chloroformate; and (ii) reacting the material thereby obtained with a compound of formula (IV-1), (IV-2), (IV-3), (IV-4) or (IV-5) as defined above.

Step (i) of the above process is conveniently effected at a suitable temperature, e.g. ambient temperature or a temperature in the region of 0° C., in a suitable solvent, e.g. a cyclic ether solvent such as tetrahydrofuran or a chlorinated solvent such as dichloromethane, typically in the presence of a base, e.g. an organic base such as pyridine or triethylamine. Step (ii) is conveniently effected at ambient or elevated temperature in a suitable solvent, e.g. a sulfoxide solvent such as dimethyl sulfoxide, or a nitrile-containing solvent such as acetonitrile, or a $C_{1-4}$ alkanol such as ethanol, or a chlorinated solvent such as dichloromethane, or a dipolar aprotic solvent such as N,N-dimethylformamide, typically in the presence of a base, e.g. an organic base such as N,N-diisopropylethylamine.

In a further procedure, the compounds of formula (I) above wherein Y represents —S(O)₂NH— may be prepared by a two-step process which comprises: (i) reacting a compound of formula (IV-1), (IV-2), (IV-3), (IV-4) or (IV-5) as defined above with methyl trifluoromethanesulfonate; and (ii) reacting the material thereby obtained with a compound of formula Z—NH₂, wherein Z is as defined above.

Step (i) of the above process is conveniently effected at a temperature in the region of 0° C. in a suitable solvent, typically a chlorinated solvent such as dichloromethane. Step (ii) is conveniently effected at an elevated temperature in a suitable solvent, e.g. a nitrile-containing solvent such as acetonitrile.

In a further procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted $C_{3-7}$ heterocycloalkyl($C_{1-6}$)alkyl, optionally substituted aryl($C_{1-6}$)alkyl or optionally substituted heteroaryl($C_{1-6}$)alkyl, may be prepared by a process which comprises reacting a compound of formula (IV-1), (IV-2), (IV-3), (IV-4) or (IV-5) as defined above with a compound of formula $Z^1$-$L^3$ wherein $Z^1$ represents $C_{1-6}$ alkyl, $C_{3-7}$ cycloalkyl($C_{1-6}$)alkyl, aryl($C_{1-6}$) alkyl, $C_{3-7}$ heterocycloalkyl-($C_{1-6}$)alkyl or heteroaryl($C_{1-6}$) alkyl, any of which groups may be optionally substituted by one or more substituents, and $L^3$ represents a suitable leaving group.

The leaving group $L^3$ is typically a halogen atom.

The reaction is conveniently effected at ambient temperature in a suitable solvent, e.g. a dipolar aprotic solvent such as N,N-dimethylformamide, or a chlorinated solvent such as dichloromethane, typically in the presence of a base. A suitable base for use in the reaction may be an organic base such as triethylamine, or an inorganic base such as caesium carbonate.

In a variant procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted $C_{3-7}$ heterocycloalkyl($C_{1-6}$)alkyl, optionally substituted aryl($C_{1-6}$)alkyl or optionally substituted heteroaryl($C_{1-6}$)alkyl, may be prepared by a two-step process which comprises: (i) reacting a compound of formula (IV-1), (IV-2), (IV-3), (IV-4) or (IV-5) as defined above with a compound of formula $Z^2$—CHO, wherein $Z^2$—$CH_2$— corresponds to a group of formula $Z^1$— as defined above; and (ii) reacting the material thereby obtained with a reducing agent.

Steps (i) and (ii) of the above process are conveniently effected at ambient temperature in a suitable solvent, e.g. a $C_{1-4}$ alkanol such as methanol. Step (i) is typically performed in the presence of a base, e.g. an organic base such as triethylamine. The reducing agent for use in step (ii) may suitably be an alkali metal borohydride such as sodium borohydride.

The compounds of formula (I) above wherein Y represents a linker group of formula (Ya) as defined above may be prepared by a process which comprises reacting a compound of formula (IV-1), (IV-2), (IV-3), (IV-4) or (IV-5) as defined above with a compound of formula (V):

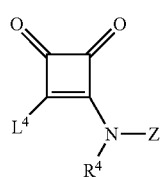

(V)

wherein Z and $R^4$ are as defined above, and $L^4$ represents a suitable leaving group.

The leaving group $L^4$ is typically a $C_{1-4}$ alkoxy group, e.g. ethoxy.

The reaction is conveniently effected at ambient temperature in a suitable solvent, e.g. a lower alkanol such as ethanol, typically in the presence of a base, e.g. an organic base such as triethylamine.

The intermediates of formula (IV-1), (IV-2), (IV-3), (IV-4) or (IV-5) above may be prepared by reacting a compound of formula (III) as defined above with a compound of formula (VIA), (VIB), (VIC), (VID) or (VIE):

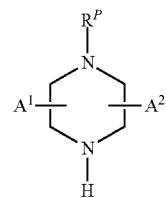

(VIA)

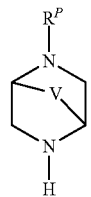

(VIB)

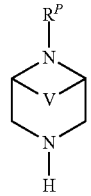

(VIC)

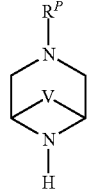

(VID)

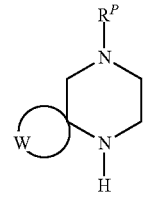

(VIE)

wherein V, W, $A^1$ and $A^2$ are as defined above, and $R^p$ represents hydrogen or an N-protecting group; followed, as necessary, by removal of the N-protecting group $R^p$.

In one embodiment, the N-protecting group $R^p$ is typically tert-butoxycarbonyl (BOC).

In another embodiment, the N-protecting group $R^p$ is typically benzyl.

The reaction between compound (III) and compound (VIA), (VIB), (VIC), (VID) or (VIE) is conveniently accomplished under conditions analogous to those described above for the reaction between the compound of formula Q-H and compound (III).

Where the N-protecting group $R^p$ is BOC, subsequent removal of the BOC group may typically be accomplished by treatment with an acid, e.g. a mineral acid such as hydrochloric acid, or an organic acid such as trifluoroacetic acid. Alternatively, the BOC group may be removed by treatment with trimethylsilyl trifluoromethanesulfonate and 2,6-lutidine, typically at ambient temperature in a suitable solvent, e.g. a chlorinated solvent such as dichloromethane. Alternatively, the BOC group may be removed by treatment with trimethylsilyl iodide, typically at ambient temperature in a suitable solvent, e.g. a chlorinated solvent such as chloroform.

Where the N-protecting group $R^p$ is benzyl, subsequent removal of the benzyl group may typically be accomplished by catalytic hydrogenation. Suitably, transfer hydrogenation conditions will be employed. A suitable hydrogenation catalyst of use in this procedure may be a transition metal catalyst such as palladium on carbon. The reaction will conveniently be performed at an elevated temperature in the presence of a hydrogen donor such as ammonium formate.

The intermediates of formula (III) above wherein $L^1$ is chloro may be prepared by treating a compound of formula (VII):

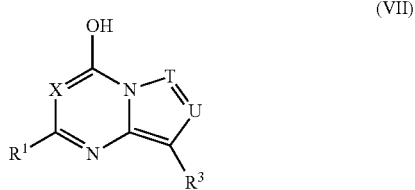

(VII)

wherein X, T, U, $R^1$ and $R^3$ are as defined above; with a chlorinating agent.

A suitable chlorinating agent for use in the above procedure is phosphorus oxychloride.

The reaction is conveniently effected by mixing the reagents at an elevated temperature, typically in the presence of a base, e.g. an organic amine such as ethylamine, N,N-diisopropylethylamine or N,N-dimethylaniline.

As will be appreciated, the intermediates of formula (IV-1), (IV-2), (IV-3), (IV-4) and (IV-5) correspond to compounds in accordance with the present invention wherein Y represents a covalent bond and Z is hydrogen. Similarly, the intermediates of formula (VIA), (VIB), (VIC), (VID) or (VIIE) wherein $R^p$ is hydrogen correspond to intermediates of formula Q-H wherein Y represents a covalent bond and Z is hydrogen. Likewise, the intermediates of formula (VIA), (VIB), (VIC), (VID) or (VIE) wherein $R^p$ is BOC correspond to intermediates of formula Q-H wherein Y represents —C(O)O— and Z is tert-butyl. Furthermore, the intermediates of formula (VIA), (VIB), (VIC), (VID) or (VIE) wherein $R^p$ is benzyl correspond to intermediates of formula Q-H wherein Y represents a covalent bond and Z is benzyl. The intermediates of formula (VII) correspond to intermediates of formula (III) wherein $L^1$ is hydroxy.

Where they are not commercially available, the starting materials of formula (V), (VIA), (VIB), (VIC), (VID), (VIE) and (VII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound comprising a N—BOC moiety may be converted into the corresponding compound comprising a N—H moiety by treatment with an acid, e.g. a mineral acid such as hydrochloric acid, or an organic acid such as trifluoroacetic acid.

A compound wherein $R^1$ represents halogen, e.g. chloro, may be converted into the corresponding compound wherein $R^1$ represents amino (—NH$_2$) in a two-step procedure which comprises: (i) treatment with benzylamine; and (ii) removal of the benzyl moiety from the material thereby obtained by catalytic hydrogenation.

A compound wherein $R^1$ represents —SR$^a$ may be converted into the corresponding compound wherein $R^1$ represents —SO$_2$R$^a$ by treatment with an oxidising agent, typically 3-chloroperoxybenzoic acid (MCPBA).

A compound wherein $R^1$ represents —SO$_2$R$^a$, e.g. methylsulfonyl, may be converted into the corresponding compound wherein $R^1$ represents —OR$^a$ by treatment with a sodium salt of formula NaOR$^a$. Similarly, a compound wherein $R^1$ represents —SO$_2$R$^a$, e.g. methylsulfonyl, may be converted into the corresponding compound wherein $R^1$ represents cyano by treatment with a cyanide salt, e.g. an alkali metal cyanide salt such as sodium cyanide. Likewise, a compound wherein $R^1$ represents —SO$_2$R$^a$, e.g. methylsulfonyl, may be converted into the corresponding compound wherein $R^1$ represents —NR$^b$R$^c$ by treatment with an amine of formula H—NR$^b$R$^c$. By analogy, a compound wherein $R^1$ represents —SO$_2$R$^a$, e.g. methylsulfonyl, may be converted into the corresponding compound wherein $R^1$ represents —NH$_2$ by treatment with ammonium hydroxide.

A compound wherein $R^1$ represents —NR$^c$COR$^d$ may be converted into the corresponding compound wherein $R^1$ represents —NHR$^c$ by treatment with a base, typically an alkali metal carbonate such as potassium carbonate.

A compound wherein $R^2$ represents —CO$_2$R$^d$, in which $R^d$ is other than hydrogen, may be converted into the corresponding compound wherein $R^2$ represents carboxy (—CO$_2$H) by treatment with a base, typically an alkali metal hydroxide such as sodium hydroxide.

A compound wherein $R^2$ represents carboxy (—CO$_2$H) may be converted into the corresponding compound wherein $R^2$ represents —CONR$^b$R$^c$ or —CON(OR$^a$)R$^b$ by treatment with the appropriate reagent of formula H—NR$^b$R$^c$ or H—N(OR$^a$)R$^b$ respectively. The reaction may typically be performed in the presence of a coupling agent such as 1-(3-dimethylaminopropyl)-3-ethylcarbodiimide hydrochloride (EDC) and an additive such as 1-hydroxybenzotriazole hydrate (HOBT), optionally in the presence of a base, e.g. an organic base such as N,N-diisopropylethylamine. Alternatively, the reaction may be performed in the presence of a coupling agent such as O-(benzotriazol-1-yl)-N,N,N',N'-tetramethyluronium tetrafluoroborate (TBTU) and a base, e.g. an organic base such as N,N-diisopropylethylamine.

A compound wherein $R^2$ represents carboxy (—CO$_2$H) may be converted into the corresponding compound wherein $R^2$ represents —CONH$_2$ by treatment with ammonium chloride, typically in the presence of a coupling agent such as EDC and an additive such as HOBT, suitably in the presence of a base, e.g. an organic base such as diisopropylamine or N,N-diisopropylethylamine. A compound wherein $R^2$ represents —CONH$_2$ may be converted into the corresponding compound wherein $R^2$ represents cyano (—CN) by treatment with phosphorus oxychloride. Alternatively, a compound wherein $R^2$ represents —CONH$_2$ may be converted into the corresponding compound wherein $R^2$ represents cyano in a two-step procedure which comprises: (i) treatment with cyanuric chloride; and (ii) treatment of the material thereby obtained with water.

A compound wherein $R^2$ represents carboxy (—CO$_2$H) may be converted into the corresponding compound wherein $R^2$ represents hydrogen by heating in the presence of a base, e.g. an organic amine such as triethylamine.

A compound wherein $R^2$ represents carboxy (—CO$_2$H) may be converted into the corresponding compound wherein $R^2$ represents hydroxymethyl (—CH$_2$OH) in a two-step procedure which comprises: (i) treatment with ethyl chloroformate and triethylamine; and (ii) treatment of the material thereby obtained with a reducing agent, typically an alkali metal borohydride such as sodium borohydride.

A compound wherein $R^2$ represents carboxy (—$CO_2H$) may be converted into the corresponding compound wherein $R^2$ represents hydroxy in a two-step procedure which comprises: (i) treatment with diphenyl phosphoryl azide; and (ii) treatment of the material thereby obtained with water.

A compound wherein $R^2$ represents carboxy (—$CO_2H$) may be converted into the corresponding compound wherein $R^2$ represents —$NHCO_2R^d$, wherein $R^d$ is other than hydrogen, in a two-step procedure which comprises: (i) treatment with diphenyl phosphoryl azide; and (ii) treatment of the material thereby obtained with the appropriate reagent of formula $R^d$—OH.

A compound wherein $R^2$ represents carboxy (—$CO_2H$) may be converted into the corresponding compound wherein $R^2$ represents a 3-substituted 1,2,4-oxadiazol-5-yl moiety in a two-step procedure which comprises: (i) treatment with an appropriately-substituted N'-hydroxyamidine derivative, typically in the presence of a coupling agent such as O-(7-azabenzotriazol-1-yl)-N,N,N',N'-tetramethyluronium hexafluorophosphate (HATU), suitably in the presence of a base, e.g. an organic base such as N,N-diisopropylethylamine; and (ii) treatment of the material thereby obtained with a strong base, suitably a strong inorganic base, e.g. an alkali metal tert-butoxide such as potassium tert-butoxide.

A compound wherein $R^2$ represents 4,5-dihydrooxazol-2-yl may be prepared from the corresponding compound wherein $R^2$ represents —$CONR^bR^c$, in which $R^b$ represents —$CH_2CH_2OH$ and $R^c$ represents hydrogen, by heating with a condensing agent such as N,N'-diisopropylcarbodiimide, typically in the presence of copper(II) trifluoromethanesulfonate.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI4KIIIβ.

PI4KIIIβ Enzyme Inhibition Assay

Procedure A

Compounds were assayed utilizing reagents from Invitrogen and Promega.

Compounds were screened in 1% DMSO (final) as 3-fold serial dilutions from a starting concentration of 20 μM. The 2.5× PI4Kβ reagent, the 2.5× PI Lipid Kinase Substrate/ATP mixture and the 5× compounds were prepared in 20 mM Tris pH 7.5, 0.5 mM EGTA, 2 mM DTT, 5 mM $MgCl_2$, 0.4% Triton. The final 25 μL Kinase Reaction consisted of: 4 nM PI4Kβ, 100 μM PI Lipid Kinase Substrate (both Invitrogen), and compound. The final ATP concentration in the assay was 10 μM. The detection reagents consisted of ADP-Glo™ Reagent and ADP-Glo™ Detect Reagent (Promega).

Briefly, compound was added to PI4Kβ followed by addition of ATP/PI Lipid Kinase Substrate mixture. The reaction mixture was incubated for 60 minutes at room temperature. The ADP-Glo™ Reagent was added and the plate was incubated for 40 minutes at room temperature, followed by addition of ADP-Glo™ Detect Reagent. The plate was incubated for a further 120 minutes and read on a Luminescence plate reader. The data was fitted with XLfit from IDBS using model number 205.

Procedure B

Compounds were assayed using a PI4Kbeta Adapta assay. Compounds were screened in 1% DMSO (final) as 3-fold serial dilutions from a starting concentration of 10 μM. The 2× PI4 KB (PI4K beta)/PI Lipid Kinase Substrate mixture was prepared in 50 mM HEPES pH 7.5, 0.1% CHAPS, 1 mM EGTA, 4 mM $MgCl_2$. The final 10 μL Kinase Reaction consisted of 7.5-60 ng PI4Kβ, and 100 μM PI Lipid Kinase Substrate in 32.5 mM HEPES pH 7.5, 0.05% CHAPS, 0.5 mM EGTA, 2 mM $MgCl_2$. The final ATP concentration in the assay was 10 μM. The detection mix consisted of EDTA (30 mM), Eu-anti-ADP antibody (6 nM) and ADP tracer. The detection mix contained the EC60 concentration of tracer for 5-150 μM ATP.

Briefly, ATP was added to compound, followed by addition of a PI4Kβ/PI Lipid Kinase Substrate mixture. The plate was shaken for 30 seconds to mix, then briefly centrifuged. The reaction mixture was incubated for 60 minutes at room temperature. The detection mix was added, then the plate was shaken and centrifuged. The plate was incubated for 60 minutes at room temperature and read on a fluorescence plate reader. The data was fitted with XLfit from IDBS using model number 205.

When tested in the above assay (Procedure A or Procedure B), the compounds of the accompanying Examples were all found to possess $IC_{50}$ values for inhibition of the activity of human PI4KIIIβ of 50 μM or better.

Certain compounds in accordance with this invention are potent inhibitors when measured in the MLR test described below.

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, No CCL-156) cells were treated with mitomycin C (Kyowa, Nycomed, Brussels, Belgium) and used as "Stimulator" cells. Responder cells (0.12×106), Stimulator cells (0.045×106) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 µCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The $IC_{50}$ was determined from a graph with at least four points, each derived from the mean of 2 experiments. The $IC_{50}$ value represents the lowest concentration of test compound (expressed in µM) that resulted in a 50% inhibition of the MLR.

Certain compounds of the accompanying Examples were found to generate $IC_{50}$ values in the MLR test of 10 µM or better.

EXAMPLES

| Abbreviations | |
|---|---|
| THF: tetrahydrofuran | MeOH: methanol |
| DMF: N,N-dimethylformamide | DMSO: dimethyl sulfoxide |
| DCM: dichloromethane | DIPEA: N,N-diisopropylethylamine |
| EtOAc: ethyl acetate | MCPBA: 3-chloroperoxybenzoic acid |
| TBME: tert-butyl methyl ether | TFA: trifluoroacetic acid |
| h: hour | r.t.: room temperature |
| MS: Mass Spectrometry | M: mass |
| LCMS: Liquid Chromatography Mass Spectrometry | |
| HPLC: High Performance Liquid Chromatography | |

ES+: Electrospray Positive Ionisation RT: retention time
Analytical and Purification Methods
Method 1
MSQ1
Column: Phenomenex Kinetex-XB C18 (2.1×100 mm, 1.7 µm column)
Flow rate: 0.6 mL/minute
Solvent A: 0.1% formic acid/water
Solvent B: 0.1% formic acid/acetonitrile
Injection volume: 3 µL
Column temperature: 40° C.
UV detection wavelength: 215 nm
Eluent: 0 to 5.3 minutes, constant gradient from 95% solvent A+5% solvent B to 100% solvent B; 5.3 to 5.8 minutes, 100% solvent B; 5.80 to 5.82 minutes, constant gradient from 100% solvent B to 95% solvent A+5% solvent B.
MS detection using Waters LCT or LCT Premier, or ZQ or ZMD
UV detection using Waters 2996 photodiode array or Waters 2787 UV or Waters 2788 UV
Method 2
Open Access 2 minutes
Column: Waters Atlantis dC18 (2.1×30 mm, 3 µm column)
Flow rate: 1 mL/minute
Solvent A: 0.1% formic acid/water
Solvent B: 0.1% formic acid/acetonitrile
Injection volume: 3 µL
UV detection wavelength: 215 nm
Eluent: 0 to 1.5 minutes, constant gradient from 95% solvent A+5% solvent B to 100% solvent B; 1.5 to 1.6 minutes, 100% solvent B; 1.60 to 1.61 minutes, constant gradient from 100% solvent B to 95% solvent A+5% solvent B; 1.61 to 2.00 minutes, 95% solvent A+5% solvent B.
Method 3
High pH (approximately pH 9.5)
Column: Waters XBridge, C18, 2.1×20 mm, 2.5 µm
Solvent A: 10 mM ammonium formate in water+0.1% ammonia solution
Solvent B: acetonitrile+5% solvent A+0.1% ammonia solution
Gradient Program:

| Time | A % | B % |
|---|---|---|
| 0.00 | 95.0 | 5.0 |
| 1.50 | 5.0 | 95.0 |
| 2.50 | 5.0 | 95.0 |
| 3.00 | 95.0 | 5.0 |

Method 4
High pH (approximately pH 9.5)
Column: Waters XBridge, C18, 2.1×20 mm, 2.5 µm
Solvent A: 10 mM ammonium formate in water+0.1% ammonia solution
Solvent B: acetonitrile+5% solvent A+0.1% ammonia solution
Gradient Program:

| Time | A % | B % |
|---|---|---|
| 0.00 | 95.0 | 5.0 |
| 4.00 | 5.0 | 95.0 |
| 5.00 | 5.0 | 95.0 |
| 5.10 | 95.0 | 5.0 |

Preparative HPLC
Acidic method
Flow rate: 40 mL/minute
Mobile Phase A: water with 0.1% formic acid
Mobile Phase B: acetonitrile with 0.1% formic acid
Column: Waters Sunfire, C18, 30 mm×100 mm
Particle Size: 10 µm
Runtime: 25.5 minutes
Inlet method: LC7_40 mL_7030_tubes.w60
Method Gradient: T=0 minutes, 75% A; 25% B
T=2 minutes, 75% A; 25% B
T=2.5 minutes, 70% A; 30% B
T=18.5 minutes, 0% A; 100% B
T=21.5 minutes, 0% A; 100% B
T=22.5 minutes, 99% A; 1% B
T=23.0 minutes, 99% A; 1% B
ACD Flow: 2 mL/minute (acetonitrile with 0.1% formic acid) throughout run
Primary wavelength (collection): 215 nm

Intermediate 1

2-Thioxo-1H-pyrazolo[1,5-a][1,3,5]triazin-4-one

1H-Pyrazol-5-amine (5 g, 0.06 mol) was dissolved in anhydrous EtOAc (35 mL) and the mixture was warmed to 80° C. Ethoxycarbonyl isothiocyanate (7.5 mL, 0.064 mol) was added dropwise and the mixture was stirred at 80° C. under nitrogen for 1 h. The mixture was cooled in an ice-water bath and the precipitate was filtered off. The solids were washed with further EtOAc. The resulting pale yellow solid was dissolved in 2M aqueous sodium hydroxide solution (60 mL) and the mixture was stirred at r.t. for 3 h. The mixture was cooled to 0° C. in an ice bath and 2N sulphuric acid (135 mL) was added. The resultant precipitate was filtered, washed with water (30 mL) and diethyl ether (20 mL), then dried in a vacuum oven, to afford the title compound (7.99 g, 79%) as a cream-coloured solid. $\delta_H$ (DMSO-$d_6$) 13.46 (s, 1H), 12.72 (s, 1H), 7.86 (d, J 1.8 Hz, 1H), 5.88 (d, J 1.8 Hz, 1H).

Intermediate 2

7-Hydroxy-3-methyl-4H-pyrazolo[1,5-a]pyrimidin-5-one

4-Methyl-1H-pyrazol-5-amine (1 g, 10.3 mmol) and diethyl malonate (1.72 mL, 11.3 mmol) were dissolved in ethanol (22 mL), then sodium ethoxide (21% w/v in ethanol, 8.5 mL, 22.8 mmol) was added. The mixture was heated at 90° C. (reflux) for 1 h, after which time a large quantity of a precipitate had formed. After cooling to r.t., the mixture was diluted with diethyl ether (20 mL) and filtered, then the solids were dried under vacuum. The solids were dissolved in water (30 mL), then 6M aqueous hydrochloric acid was added to obtain pH 3. The mixture was stirred in an ice-water bath for 30 minutes. The resultant precipitate was filtered, washed with water (10 mL) and diethyl ether (50 mL), then dried in a vacuum oven, to afford the title compound (0.61 g, 36%) as a pale orange solid. $\delta_H$ (DMSO-$d_6$; mixture of tautomers) 11.43 (s, 1H), 7.64 (s, 1H), 3.75 (s, 2H), 1.95 (s, 3H).

Intermediate 3

8-Methyl-2-thioxo-1H-pyrazolo[1,5-a][1,3,5]triazin-4-one

Method 1

Prepared using 4-methyl-1H-pyrazol-5-amine (commercially available) (1.0 g, 10.3 mmol) and applying the procedure for Intermediate 1. The title compound (1.02 g, 54%) was isolated as a white powder. $^{13}$C NMR δ (DMSO-$d_6$, 75 MHz) 172.68, 148.45, 146.76, 145.87, 100.34, 8.38. MS (m/z) 183 [M+H]$^+$.

Method 2

4-Methyl-1H-pyrazol-5-amine (3 g, 30.89 mmol) was dissolved in EtOAc (20 mL) and heated to 80° C. Ethoxycarbonyl isothiocyanate (3.9 mL, 33.07 mmol) was added dropwise and the mixture was stirred at 80° C. for 1 h. The mixture was cooled in an ice bath, then the solids were filtered off, washed with diethyl ether (20 mL) and dried under vacuum. The resulting cream-coloured solid was dissolved in 2M aqueous sodium hydroxide solution (67 mL) and the mixture was stirred for 3 h. The mixture was cooled to 0° C., then 2N aqueous sulphuric acid (90 mL) was added. The resultant precipitate was filtered off, washed with water (100 mL) and diethyl ether (30 mL), then dried in a vacuum oven, to afford the title compound (4.7 g, 84%) as a white solid. $\delta_H$ (DMSO-$d_6$) 13.38 (s, 1H), 12.49 (s, 1H), 7.74 (s, 1H), 2.03 (s, 3H).

Intermediate 4

7-Methyl-2-thioxo-1H-pyrazolo[1,5-a][1,3,5]triazin-4-one

Prepared using 3-methyl-1H-pyrazol-5-amine (commercially available) (1.0 g, 10.3 mmol) and applying the procedure for Intermediate 1. The title compound (1.25 g, 67%) was isolated as a white powder. $^{13}$C NMR δ (DMSO-$d_6$, 75 MHz) 172.93, 155.28, 141.33, 140.72, 89.88, 13.99. MS (m/z) 183 [M+H]$^+$.

Intermediate 5

7-(4-Fluorophenyl)-2-thioxo-1H-pyrazolo[1,5-a][1,3,5]triazin-4-one

To a solution of 3-(4-fluorophenyl)-3-oxopropanenitrile (1 g, 6.13 mmol) in ethanol (11 mL) was added hydrazine hydrate (1.82 mL, 36.8 mmol). The reaction mixture was stirred at 100° C. in a sealed vessel for 6 h. The solvents were evaporated in vacuo and the residue was extracted with EtOAc and brine. The organic solvents were dried over magnesium sulphate and evaporated in vacuo. The residue (1.18 g) was dissolved in EtOAc (anhydrous), then the procedure for Intermediate 1 was applied. The title compound (914 mg, 57%) was isolated as a white powder. $^{13}$C NMR δ (DMSO-$d_6$, 75 MHz) 173.19, 163.01 (d, $J_{CF}$ 245.0 Hz), 154.61, 141.81, 141.59, 128.63 (2C, d, $J_{CF}$ 8.4 Hz), 127.97, 115.94 (2C, d, $J_{CF}$ 21.6 Hz), 86.88. MS (m/z) 263 [M+H]$^+$.

Intermediate 6

3-Methylpyrazolo[1,5-a]pyrimidin-7-ol

4-Methyl-1H-pyrazol-5-amine (500 mg, 5.15 mmol) and 1,3-dimethyl-1,2,3,4-tetrahydropyrimidine-2,4-dione (685 mg, 4.89 mmol) were combined in ethanol (4.5 mL), then sodium ethoxide (21% in ethanol, 2.6 mL, 6.96 mmol) was added. The mixture was heated at 90° C. under nitrogen for 1 h, then cooled in an ice bath. The precipitate was filtered, washed with further ethanol (3 mL) and dried in a vacuum oven, to afford the title compound (450 mg, 62%) as a cream-coloured solid. $\delta_H$ (DMSO-$d_6$) 12.02 (s, 1H), 8.37 (d, J 7.9 Hz, 1H), 7.60 (s, 1H), 5.85 (d, J 7.9 Hz, 1H), 2.01 (s, 3H).

Intermediate 7

Ethyl 7-hydroxy-2-methylpyrazolo[1,5-a]pyrimidine-6-carboxylate

A solution of 3-methyl-1H-pyrazol-5-amine (0.49 g, 5.05 mmol) and diethyl 2-(ethoxymethylene)propanedioate (1 g, 4.6 mmol) in acetic acid (20 mL) was heated at 120° C. for 2 h. The reaction mixture was cooled to 0° C. and filtered. The residue was washed with ethanol and diethyl ether, then dried under vacuum, to afford the title compound (1.7 g, 77%) as an off-white solid. LCMS [M+H]+ 222.05, RT 0.61 minutes, 99.2%.

Intermediate 8

2-Methylpyrazolo[1,5-a]pyrimidin-7-ol

To a solution of Intermediate 7 (8 g, 36.2 mmol) in ethanol (100 mL) was added sodium hydroxide (10 g, 250 mmol) and the mixture was heated at reflux for 12 h. The reaction mixture was concentrated under reduced pressure, then the residue was diluted with water, acidified with 1N hydrochloric acid to pH 2, and filtered. The residue was dried under vacuum. The resulting white solid was taken up in Dowtherm (60 mL) and heated at 220° C. for 3 h. The reaction mixture was filtered and washed with hexane to afford the title compound (3.57 g, 71%) as a white solid. $\delta_H$ (DMSO-$d_6$, 400 MHz) 7.78 (d, J 7.3 Hz, 1H), 6.00 (s, 1H), 5.61 (d, J 7.3 Hz, 1H), 2.28 (s, 3H). LCMS [M+H]+ 150.0, RT 0.15 minutes, 99.6%.

Intermediate 9

2-(Methylsulfanyl)-3H-pyrazolo[1,5-a][1,3,5]triazin-4-one

Method 1

To a solution of Intermediate 1 (1.38 g, 8.2 mmol) in ethanol (33 mL) and 1.73N sodium hydroxide solution (9.4 mL) at r.t. was added methyl iodide (512 μL, 8.2 mmol). The mixture was stirred overnight, then cooled to 0° C. To the suspension was added dropwise 2N sulfuric acid (4.8 mL) and the mixture was stirred for 1 h. The solids were filtered off, rinsed with water and diethyl ether, then dried, yielding the title compound (1.01 g, 68%) a white powder. $^{13}$C NMR δ (DMSO-$d_6$, 75 MHz) 157.05, 148.54, 145.83, 143.62, 97.24, 13.16. MS (m/z) 183 [M+H]+.

Method 2

Intermediate 1 (7.99 g, 0.05 mol) was suspended in a mixture of ethanol (200 mL) and 2M aqueous sodium hydroxide solution (48 mL). The mixture was very thick, so was diluted with water (approximately 10 mL). The mixture was cooled to 0° C., then iodomethane (3 mL, 0.05 mol) was added slowly. The mixture briefly became a solution, before a white precipitate started to form. The mixture was warmed to r.t. and stirred for 3 h, then left to stand over the weekend. The mixture was cooled to 0° C., then 2N aqueous sulphuric acid (58 mL) was added and the mixture was stirred for 1 h. The resultant precipitate was filtered, washed with water (200 mL) and cyclohexane (50 mL), then dried in a vacuum oven, to afford the title compound (6.85 g, 79%) as a white solid. $\delta_H$ (DMSO-$d_6$) 12.94 (s, 1H), 7.96 (d, J 1.9 Hz, 1H), 6.34 (d, J 1.9 Hz, 1H), 2.53 (s, 3H).

Intermediate 10

8-Methyl-2-(methylsulfanyl)-3H-pyrazolo[1,5-a][1,3,5]triazin-4-one

Method 1

Prepared using Intermediate 3 (1.02 g, 5.6 mmol) and applying the procedure for Intermediate 9, Method 1. The title compound (579 mg, 53%) was isolated as a white powder. $^{13}$C NMR δ (DMSO-$d_6$, 75 MHz) 155.45, 146.69, 145.36, 143.71, 105.63, 13.03, 7.20. MS (m/z) 197 [M+H]+.

Method 2

Intermediate 3 (4.7 g, 25.8 mmol) was suspended in ethanol (100 mL) and 2M aqueous sodium hydroxide solution (26 mL) was added. The mixture was cooled to 0° C. in an ice bath and iodomethane (1.65 mL, 26.5 mmol) was added. The mixture was warmed to r.t. and stirred for 18 h. The mixture was cooled to 0° C. in an ice bath and 2N aqueous sulphuric acid (16 mL) was added. The mixture was left to stir for 1 h. The resultant precipitate was filtered off and the solids were washed with water (100 mL). Further precipitate formed, so the filtrate was concentrated to approximately half the volume and the solids were filtered off. The combined solids were washed with water (50 mL) and cyclohexane (50 mL), then dried in a vacuum oven, to afford the title compound (3.54 g, 70%) as a white solid. $\delta_H$ (DMSO-$d_6$) 12.71 (s, 1H), 7.86 (s, 1H), 2.56 (s, 3H), 2.09 (s, 3H).

Intermediate 11

7-Methyl-2-(methylsulfanyl)-3H-pyrazolo[1,5-a][1,3,5]triazin-4-one

Prepared using Intermediate 4 (1.25 g, 6.9 mmol) and applying the procedure for Intermediate 9, Method 1. The title compound (1.03 g, 76%) was isolated as a white powder. $^{13}$C NMR δ (DMSO-$d_6$, 75 MHz) 156.90, 154.89, 148.93, 143.22, 97.20, 14.35, 13.13. MS (m/z) 197 [M+H]+.

Intermediate 12

7-(4-Fluorophenyl)-2-(methylsulfanyl)-3H-pyrazolo[1,5-a][1,3,5]triazin-4-one

Prepared using Intermediate 5 (914 mg, 3.5 mmol) and applying the procedure for Intermediate 9, Method 1. The title compound (594 mg, 61%) was isolated as a yellow powder. MS (m/z) 277 [M+H]+.

Intermediate 13

8-Chloro-2-(methylsulfanyl)-3H-pyrazolo[1,5-a][1,3,5]triazin-4-one

Intermediate 9 (1 g, 5.49 mmol) was suspended in DCM (30 mL) and N-chloro-succinimide (0.81 g, 6.04 mmol) was added. The mixture was stirred at r.t. for 90 minutes. LCMS showed that no reaction had occurred, so anhydrous DMF (5 mL) was added and the resulting solution was stirred at r.t. for 90 minutes. The solvent was removed under vacuum, then water (20 mL) was added. The resultant precipitate was filtered, washed with water (2×30 mL) and cyclohexane (20 mL), then dried under vacuum, to afford the title compound (0.96 g, 80%) as a white solid. $\delta_H$ (DMSO-$d_6$) 8.13 (s, 1H), 2.57 (s, 3H).

Intermediate 14

5-Amino-2-methyl-4H-pyrazolo[1,5-a]pyrimidin-7-one

A solution of the hydrochloride salt of ethyl 3-ethoxy-3-iminopropionate (2.3 g, 10 mmol) in a mixture of EtOAc and water was neutralized with saturated aqueous sodium hydrogencarbonate solution at 0° C. The organic phase was collected and washed with water and brine, then dried with anhydrous sodium sulfate. The drying agent was filtered off and the volatiles were evaporated. The resulting colourless oil (pure ethyl 3-ethoxy-3-iminopropionate) (10 mmol) was dissolved in absolute ethanol (50 mL) and 3-methyl-5-amino-1H-pyrazole (1.02 g, 10 mmol) was added. The reaction mixture was heated at reflux for 48 h, then cooled to 0° C. The resulting white precipitate was collected and dried in vacuo to yield the title compound (1.37 g, 83%). $^{13}$C NMR δ (DMSO-$d_6$, 75 MHz) 157, 153.5, 150, 140.4, 87.6, 74.2, 13.9. MS (m/z) 165 [M+H]$^+$.

Intermediate 15

N-(2-Methyl-7-oxo-4H-pyrazolo[1,5-a]pyrimidin-5-yl)acetamide

A suspension of Intermediate 14 (164 mg, 1.0 mmol) in acetic anhydride (3 mL) was heated at reflux for 4 h. The reaction mixture was cooled to r.t., then precipitated in diethyl ether, to provide the title compound (140 mg, 67%) as a brown solid. $^{13}$C NMR δ (DMSO-$d_6$, 75 MHz) 171.1, 156.4, 151.1, 145.9, 139.9, 90.5, 81.2, 24, 13.9. MS (m/z) 207 [M+H]$^+$.

Intermediate 16

4-Chloro-8-methyl-2-(methylsulfanyl)pyrazolo[1,5-a][1,3,5]triazine

Intermediate 10 (2 g, 10.2 mmol) was suspended in phosphorus oxychloride (28.5 mL, 305.8 mmol) and N,N-dimethylaniline (0.65 mL, 5.1 mmol) was added. Upon heating, the solids dissolved and the mixture gradually turned a deep green colour. The mixture was heated at 105° C. (reflux) for 4.5 h, then concentrated under vacuum, to afford the title compound (2.67 g, 98%) as a yellow solid. LCMS (ES+) [M+H]$^+$ 215, RT 1.28 minutes (method 2).

Intermediate 17

7-Chloro-2-methylpyrazolo[1,5-a]pyrimidine

To a stirred solution of Intermediate 8 (3.5 g, 23.5 mmol) in 1,4-dioxane (35 mL) were added triethylamine (5.6 mL, 39.9 mmol) and phosphorus oxychloride (5.6 mL, 59.7 mmol). The reaction mixture was heated at 100° C. for 1 h, then quenched with ice and extracted with EtOAc. The organic layer was dried over sodium sulphate and concentrated under reduced pressure. The crude material was purified by silica gel column chromatography, using 2% MeOH in DCM as eluent, to afford the title compound (3.0 g, 79%) as an off-white solid. $δ_H$ (DMSO-$d_6$, 400 MHz) 8.43 (d, J 4.6 Hz, 1H), 7.31 (d, J 4.5 Hz, 1H), 6.70 (s, 1H), 2.47 (s, 3H).

Intermediate 18

N-(7-Chloro-2-methylpyrazolo[1,5-a]pyrimidin-5-yl)acetamide

To a suspension of Intermediate 15 (206 mg, 1 mmol) in 1,4-dioxane (6 mL) were added phosphorus oxychloride (176 μL, 1.9 mmol) and DIPEA (344 μL, 2 mmol). The reaction mixture was heated at 85° C. for 5.5 h. The volatiles were evaporated, then the residue was partitioned between DCM and water. The organic phase was washed with water and brine, then dried with sodium sulfate. The drying agent was filtered off and the filtrate was concentrated to dryness. The residue was purified by silica gel chromatography, eluting with 1:2 EtOAc:n-heptane, to provide the title compound (98 mg, 43%). $δ_H$ (CDCl$_3$, 300 MHz) 8.11 (s, 1H, NH), 8.03 (s, 1H), 6.27 (s, 1H), 2.52 (s, 3H), 2.24 (s, 3H). MS (m/z) 225 [M+H]$^+$.

Intermediate 19 tert-Butyl (3S)-3-methyl-4-[2-(methylsulfanyl)pyrazolo[1,5-a][1,3,5]triazin-4-yl]-piperazine-1-carboxylate Method 1

To Intermediate 9 (1.01 g, 5.6 mmol) were added phosphorus oxychloride (15.5 mL) and N,N-dimethylaniline (340 μL). The reaction mixture was stirred at 105° C. until the starting material was completely consumed. The solvents were evaporated in vacuo and the crude residue was dissolved in THF (60 mL), then triethylamine (7.7 mL, 55.6 mmol) and (S)-tert-butyl 3-methylpiperazine-1-carboxylate (1.22 g) were added. The reaction mixture was stirred at r.t. until all starting material was consumed, whereupon the solvents were evaporated in vacuo. The crude residue was extracted with EtOAc and saturated aqueous sodium bicarbonate solution, followed by brine. The solvents were dried over magnesium sulfate and evaporated in vacuo. The residue was purified by flash chromatography, the mobile phase being a mixture of EtOAc and cyclohexane (in a ratio gradually increasing from 10% to 20% EtOAc in cyclohexane), yielding the title compound (1.162 g, 57%) as a yellow powder. $^{13}$C NMR δ (CD$_3$OD, 75 MHz) 167.94, 156.33, 152.99, 148.88, 145.64, 93.78, 81.24, 51.21, 44.88, 43.92, 41.85, 28.64 (3C), 15.67, 14.24. MS (m/z) 365 [M+H]$^+$.

Method 2

Intermediate 9 (0.99 g, 5.4 mmol) was suspended in phosphorus oxychloride (15.2 mL, 163.4 mmol) and N,N-dimethylaniline (0.34 mL, 2.72 mmol) was added. The mixture was heated at 105° C. (reflux) for 3 h. The resulting yellow-green solution was cooled to r.t. and concentrated in vacuo. The residue was azeotroped with toluene (2×50 mL) and dried thoroughly. The resulting yellow-green gum was dissolved in THF (40 mL) and the mixture was cooled to 0° C. DIPEA (7.81 mL, 44.85 mmol) was added, followed by tert-butyl (3S)-3-methylpiperazine-1-carboxylate (1.08 g, 5.38 mmol), then the mixture was stirred at r.t. for 2 h. The mixture was evaporated to dryness, reconstituted in EtOAc (100 mL) and washed with saturated aqueous sodium bicarbonate solution (100 mL) followed by brine (100 mL), then dried (sodium sulfate), filtered and concentrated in vacuo. The residue was purified by flash column chromatography (Isolera 4, SNAP 100 g), using 0-50% TBME in heptane as eluent, to yield the title compound (1.17 g, 72%) as a yellow gum. $δ_H$ (DMSO-$d_6$, 500 MHz) 8.07 (d, J 2.2 Hz, 1H), 6.28 (d, J 2.2 Hz, 1H), 5.55 (s, 2H), 3.99 (d, J 14.7 Hz, 1H), 3.82 (d, J 13.4 Hz, 1H), 3.47 (s, 1H), 3.26 (d, J 10.9 Hz, 1H), 3.08 (s, 1H), 2.48 (s, 3H), 1.43 (s, 9H), 1.27 (d, J 6.7 Hz, 3H). LCMS (ES+) [M+H]$^+$ 365, RT 1.48 minutes (method 2).

Intermediate 20 tert-Butyl (3S)-3-methyl-4-[8-methyl-2-(methylsulfanyl)pyrazolo[1,5-a][1,3,5]triazin-4-yl]piperazine-1-carboxylate Method 1

Prepared using Intermediate 10 (750 mg, 3.8 mmol) and applying the procedure for Intermediate 19, Method 1. The title compound (737 mg, 51.2%) was isolated as a yellow powder. MS (m/z) 379 [M+H]+.

Method 2

Intermediate 16 (7.64 mmol) was dissolved in THF (40 mL) and the mixture was cooled in an ice-water bath. DIPEA (13.3 mL, 76.4 mmol) was added, followed by tert-butyl (3S)-3-methylpiperazine-1-carboxylate (1.68 g, 8.4 mmol), then the mixture was stirred at r.t. for 63 h. The mixture was concentrated under vacuum and EtOAc (100 mL) was added. The mixture was washed with saturated aqueous sodium bicarbonate solution (50 mL) and (50 mL), then dried over sodium sulfate and concentrated under vacuum. The resulting dark orange oil was purified by flash column chromatography, eluting with a gradient of 0-20% EtOAc in heptane. The residue was further purified by flash column chromatography, eluting with a gradient of 0-30% TBME in heptane, to afford the title compound (1.1 g, 36%) as a pale yellow gum. $\delta_H$ (CDCl$_3$) 7.73 (s, 1H), 5.69 (s, 1H), 5.35 (s, 1H), 4.22 (s, 1H), 3.95 (s, 1H), 3.49 (t, J 11.1 Hz, 1H), 3.25 (s, 1H), 3.03 (s, 1H), 2.57 (s, 3H), 2.24 (s, 3H), 1.49 (s, 9H), 1.36 (d, J 6.7 Hz, 3H).

Intermediate 21 tert-Butyl (3S)-3-methyl-4-[7-methyl-2-(methylsulfanyl)pyrazolo[1,5-a][1,3,5]triazin-4-yl]piperazine-1-carboxylate Prepared using Intermediate 11 (450 mg, 2.3 mmol) and applying the procedure for Intermediate 19, Method 1. The title compound (425 mg, 49%) was isolated as a yellow powder. $^{13}$C NMR δ (DMSO-d$_6$, 75 MHz) 166.24, 154.72, 154.49, 152.44, 147.23, 92.96, 79.82, 49.22, 40.93, 40.50, 39.69, 28.36 (3C), 15.01, 14.34, 13.77. MS (m/z) 379 [M+H]+.

Intermediate 22 tert-Butyl (3S)-4-[7-(4-fluorophenyl)-2-(methylsulfanyl)pyrazolo[1,5-a][1,3,5]triazin-4-yl]-3-methyl-piperazine-1-carboxylate Prepared using Intermediate 12 (550 mg, 2.0 mmol) and applying the procedure for Intermediate 19, Method 1. The title compound (557 mg, 61%) was isolated as a yellow powder. $^{13}$C NMR δ (CDCl$_3$, 75 MHz) 166.82, 163.19 (d, $J_{CF}$ 247.5 Hz), 154.70, 154.36, 153.03, 147.41, 128.27, 128.00 (2C, d, $J_{CF}$ 8.2 Hz), 115.43 (2C, d, $J_{CF}$ 21.0 Hz), 90.04, 79.92, 49.69, 45.17, 43.45, 40.66, 28.08 (3C), 15.28, 13.82. MS (m/z) 459 [M+H]+.

Intermediate 23 tert-Butyl (3S)-4-[8-chloro-2-(methylsulfanyl)pyrazolo[1,5-a][1,3,5]triazin-4-yl]-3-methylpiperazine-1-carboxylate Intermediate 13 (0.4 g, 1.85 mmol) was suspended in phosphorus oxychloride (5.2 mL, 55.79 mmol) and N,N-dimethylaniline (0.12 mL, 0.92 mmol) was added. The mixture was heated at 105° C. under nitrogen for 6 h, then concentrated under vacuum. The resulting brown/black oily residue was dissolved in THF (30 mL) and triethylamine (2.6 mL, 18.7 mmol) was added, followed by tert-butyl (3S)-3-methylpiperazine-1-carboxylate (410 mg, 2.05 mmol). The mixture was stirred at r.t. overnight, then concentrated under vacuum and partitioned between EtOAc (70 mL) and saturated aqueous sodium bicarbonate solution (50 mL). The aqueous phase was extracted with further EtOAc (30 mL) and the combined organic layers were washed with brine (50 mL), then dried over sodium sulfate and concentrated under vacuum. The resulting brown oil was purified by flash column chromatography, eluting with a gradient of 0-20% EtOAc in heptane. The resulting yellow oil was further purified by flash column chromatography, eluting with a gradient of 0-30% TBME in heptane, to afford the title compound (565 mg, 77%) as a yellow glass. $\delta_H$ (CDCl$_3$) 7.81 (s, 1H), 5.62 (s, 1H), 5.29 (s, 1H), 4.15 (s, 1H), 3.95 (d, J 13.5 Hz, 1H), 3.48 (td, J 13.7, 13.1, 3.5 Hz, 1H), 3.23 (d, J 10.3 Hz, 1H), 3.16-2.98 (m, 1H), 2.57 (s, 3H), 1.49 (s, 9H), 1.36 (d, J 6.7 Hz, 3H). LCMS (ES+) [M+H]+ 399, RT 1.62 minutes (method 2).

Intermediate 24 tert-Butyl (3S)-3-methyl-4-(3-methylpyrazolo[1,5-a]pyrimidin-7-yl)piperazine-1-carboxylate Intermediate 6 (450 mg, 3.02 mmol) was suspended in phosphorus oxychloride (8.5 mL, 91.19 mmol) and N,N-dimethylaniline (0.19 mL, 1.51 mmol) was added. The mixture was heated at 110° C. under nitrogen for 3 h, then concentrated under vacuum. The residue was dissolved in DCM (30 mL), then washed with water (20 mL). The aqueous layer was extracted with further DCM (2×10 mL). The combined organic layers were dried over sodium sulfate and concentrated under vacuum. The resulting yellow solid was dissolved in ethanol (10 mL) and DIPEA (1.28 mL, 7.37 mmol) was added, followed by tert-butyl (3S)-3-methylpiperazine-1-carboxylate (708.1 mg, 3.54 mmol). The mixture was heated at 90° C. (reflux) for 24 h but no reaction was observed. The mixture was transferred to a microwave vial and heated at 150° C. for 30 minutes under microwave irradiation, then concentrated under vacuum and dissolved in 1-methyl-2-pyrrolidinone (5 mL). tert-Butyl (3S)-3-methylpiperazine-1-carboxylate (708.1 mg, 3.54 mmol) and DIPEA (0.62 mL, 3.54 mmol) were added, then the mixture was heated at 170° C. under microwave irradiation for 40 minutes. Water (20 mL) was added and the mixture was extracted with EtOAc (2×25 mL). The combined organic layers were washed with brine (20 mL), dried over sodium sulfate and concentrated under vacuum. The residue was purified by flash column chromatography, eluting with a 0-60% gradient of EtOAc in heptane, to afford the title compound (154 mg, 14%) as an orange oil. LCMS (ES+) [M+H]+ 332, RT 1.35 minutes (method 2).

Intermediate 25 tert-Butyl (3S)-3-methyl-4-[2-(methylsulfonyl)pyrazolo[1,5-a][1,3,5]triazin-4-yl]-piperazine-1-carboxylate Intermediate 19 (1.17 g, 3.21 mmol) was dissolved in DCM (70 mL) and MCPBA (70%, 1.6 g, 6.5 mmol) was added under a nitrogen atmosphere at 0° C. The mixture was allowed to warm to r.t. and stirred for 2 h, then washed with saturated aqueous sodium bicarbonate solution (4×50 mL). The organic layer was dried (sodium sulfate), filtered and concentrated in vacuo. The residue was purified by flash column chromatography (Isolera 4, SNAP 50 g), using 0-100% EtOAc in heptane as eluent, to give the title compound (1.19 g, 90% purity, 84%) as a white solid. $\delta_H$ (CDCl$_3$, 500 MHz) 8.07 (d, J 2.2 Hz, 1H), 6.62 (d, J 2.2 Hz, 1H), 6.12 (s, 1H), 5.12 (s, 1H), 4.36-4.18 (m, 1H), 4.08-3.90 (m, 1H), 3.78-3.52 (m, 1H), 3.33-3.23 (m, 4H), 3.22-3.03 (m, 1H), 1.50 (s, 9H), 1.43 (d, J 6.7 Hz, 3H). LCMS (ES+) [M+H-$^t$Bu]$^+$ 341, RT 1.28 minutes (method 2).

Intermediate 26 tert-Butyl (3S)-3-methyl-4-[8-methyl-2-(methylsulfonyl)pyrazolo[1,5-a][1,3,5]triazin-4-yl]piperazine-1-carboxylate Intermediate 20 (1.1 g, 2.91 mmol) was dissolved in DCM (75 mL) and MCPBA (70% pure, 1.45 g, 5.88 mmol) was added. The mixture was stirred at r.t. for 2 h, then washed with saturated aqueous sodium bicarbonate solution (4×50 mL). The organic layer was dried over sodium sulfate and concentrated under vacuum. The residue was purified by flash column chromatography, eluting with a gradient of 0-50% EtOAc in heptane, to afford the title compound (1.09 g, 87%) as a white solid. $\delta_H$ (CDCl$_3$) 7.91 (s, 1H), 6.11 (br s, 1H), 5.30 (br s, 1H), 4.33-4.06 (m, 1H), 3.98 (s, 1H), 3.65-3.50 (m, 1H), 3.33 (s, 3H), 3.27 (d, J 8.1 Hz, 1H), 3.11 (s, 1H), 2.28 (s, 3H), 1.49 (s, 9H), 1.41 (d, J 6.7 Hz, 3H).

Intermediate 27 tert-Butyl (3S)-4-(2-aminopyrazolo[1,5-a][1,3,5]triazin-4-yl)-3-methylpiperazine-1-carboxylate Intermediate 25 (90%, 1.19 g, 2.7 mmol) was dissolved in 1,4-dioxane (6 mL) in a pressure tube and aqueous ammonia (6.72 mL, 169 mmol) was added. The vessel was sealed and the mixture was heated at 100° C. for 3 h. Upon cooling to r.t., the reaction mixture was evaporated to dryness, then dried under vacuum at 40° C. overnight, to give the title compound (1.24 g, ~80% purity, quantitative) as a white solid, as a mixture of atropisomers which were utilised without further purification. Major atropisomer: $\delta_H$ (DMSO-d$_6$, 500 MHz) 7.81 (d, J 2.1 Hz, 1H), 6.48 (s, 2H), 5.75 (d, J 2.1 Hz, 1H), 5.62-5.33 (m, 1H), 5.25-4.85 (m, 1H), 4.05-3.86 (m, 1H), 3.84-3.70 (m, 2H), 3.14-2.95 (m, 2H), 1.42 (s, 9H), 1.23 (d, J 6.6 Hz, 3H). LCMS (ES+) [M+H]$^+$ 334, RT 1.05 minutes (method 2).

Intermediate 28 tert-Butyl (3S)-4-(2-amino-8-methylpyrazolo[1,5-a][1,3,5]triazin-4-yl)-3-methylpiperazine-1-carboxylate Intermediate 26 (990 mg, 2.41 mmol) was dissolved in 1,4-dioxane (6 mL) in a pressure tube and ammonium hydroxide (6 mL, 150.7 mmol) was added. The vessel was sealed and the mixture was heated at 100° C. for 2 h. The mixture was concentrated under vacuum to afford the title compound (981 mg, 85% purity, 100%) as a sticky yellow solid. $\delta_H$ (DMSO-d$_6$) 7.68-7.63 (s, 1H), 6.45-6.28 (br s, 2H), 5.53 (br s, 1H), 5.04 (br s, 1H), 3.94 (s, 1H), 3.85-3.75 (m, 1H), 3.01 (d, J 11.9 Hz, 1H), 2.84 (s, 1H), 2.70 (t, J 11.8 Hz, 1H), 1.97 (s, 3H), 1.42-1.40 (s, 9H), 1.22-1.08 (d, J 6.4 Hz, 3H). NMR indicates the presence of two species, suggesting the possibility of restricted rotation or atropisomers.

Intermediate 29 tert-Butyl (3S)-4-(2-amino-8-chloropyrazolo[1,5-a][1,3,5]triazin-4-yl)-3-methylpiperazine-1-carboxylate Intermediate 23 (465 mg, 1.17 mmol) was dissolved in DCM (30 mL) and cooled to 0° C. in an ice bath. MCPBA (403 mg, 2.34 mmol) was added, then the mixture was warmed to r.t. and stirred for 4 h. LCMS showed that the reaction was not complete, so further MCPBA (200 mg, 1.16 mmol) was added and the mixture was stirred at r.t. for 2 h. Saturated aqueous sodium sulfite solution (2 mL) was added and the mixture was washed with saturated aqueous sodium bicarbonate solution (2×20 mL). The organic layer was dried over sodium sulfate and concentrated under vacuum. The resulting yellow solid was dissolved in 1,4-dioxane (4 mL) in a pressure tube and aqueous ammonium hydroxide solution (3 mL, 75.3 mmol) was added. The vessel was sealed and the mixture was heated at 100° C. for 2 h, then concentrated under vacuum. The resulting cream-coloured solid was dissolved in chloroform (75 mL), isopropanol (25 mL) and MeOH (approximately 5 mL), then washed with saturated aqueous sodium bicarbonate solution (30 mL). The organic layer was concentrated under vacuum to afford the title compound (380 mg, 89%) as a cream-coloured solid. LCMS (ES+) [M+H]$^+$ 368, RT 1.28 minutes (method 2).

Intermediate 30 tert-Butyl (3S)-4-(5-acetamido-2-methylpyrazolo[1,5-a]pyrimidin-7-yl)-3-methylpiperazine-1-carboxylate To a solution of Intermediate 18 (98 mg, 0.44 mmol) in 1,4-dioxane (10 mL) were added tert-butyl (3S)-3-methylpiperazine-1-carboxylate (176 mg, 0.87 mmol) and DIPEA (150 µL, 0.87 mmol). The reaction mixture was heated at reflux for 42 h. The volatiles were evaporated and the residue was purified by silica gel chromatography, eluting with EtOAc:n-heptane (1:2, then 1:1), to provide title compound (141 mg, 83%). $^{13}$C NMR δ (CDCl$_3$, 75 MHz) 169.9, 155.1, 154.0, 151.6, 150.9, 149.8, 93.2, 85.0, 80.1, 50.1, 48.2, 47.5, 42.7, 28.5 (3C), 24.8, 14.8, 13.7. MS (m/z) 389 [M+H]$^+$.

Intermediate 31 tert-Butyl (3S)-4-(5-amino-2-methylpyrazolo[1,5-a]pyrimidin-7-yl)-3-methylpiperazine-1-carboxylate To a solution of Intermediate 30 (141 mg, 0.36 mmol) in MeOH (6 mL) was added potassium carbonate (150 mg, 1.09 mmol) and the reaction mixture was stirred at r.t. for 17 h. The volatiles were evaporated and the residue was partitioned between DCM and water. The organic phase was washed with water and brine, then dried with anhydrous sodium sulfate. The drying agent was filtered off, and the filtrate was concentrated, to provide the title compound (120 mg, 96%). $^{13}$C NMR δ (CDCl$_3$, 75 MHz) 157.4, 155.1, 153.4, 151.3, 150.7, 91.6, 82.6, 80.1, 49.6, 48.5, 47.8, 42.6, 28.4 (3C), 14.8, 12.8. MS (m/z) 347 [M+H]$^+$.

Intermediate 32

8-Chloro-4-[(2S)-2-methylpiperazin-1-yl]pyrazolo[1,5-a][1,3,5]triazin-2-amine dihydrochloride Intermediate 29 (95% pure, 380 mg, 0.98 mmol) was dissolved in 1,4-dioxane (3 mL) and 4M hydrogen chloride in 1,4-dioxane (2 mL) was added. The mixture was stirred at r.t. for 4 h, over which time a precipitate had formed. The mixture was concentrated under vacuum to afford the title compound (349 mg, 105%) as a cream-coloured solid, which was utilised without further purification. LCMS (ES+) [M+H]$^+$ 268, RT 0.42 minutes (method 2).

Intermediate 33

3-Methyl-7-[(2S)-2-methylpiperazin-1-yl]pyrazolo[1,5-a]pyrimidine hydrochloride Hydrogen chloride in 1,4-dioxane (4M, 2 mL) was added to Intermediate 24 (154 mg, 0.47 mmol) and the solution was stirred at r.t. for 2 h, after which time a precipitate had formed. The mixture was concentrated under vacuum to afford the title compound (126 mg, 101%) as a golden brown solid, which was utilised without further purification. LCMS (ES+) [M+H]$^+$ 232, RT 0.65 minutes (method 2).

Intermediate 34

2-Methyl-7-[(2S)-2-methylpiperazin-1-yl]pyrazolo[1,5-a]pyrimidin-5-amine

Intermediate 31 (120 mg, 0.35 mmol) was dissolved in a mixture of TFA (4 mL) and DCM (4 mL) and the reaction mixture was stirred at r.t. for 0.5 h. The volatiles were evaporated, and the residue was co-evaporated with aqueous ammonia solution (7N) in MeOH, to provide the title compound (81 mg, 95%). MS (m/z) 247 [M+H]$^+$.

Intermediate 35

2-Methyl-7-[(2S)-2-methylpiperazin-1-yl]pyrazolo[1,5-a]pyrimidine

To a solution of Intermediate 17 (2 g, 12.0 mmol) in DMF (20 mL) were added DIPEA (8.34 mL, 47.9 mmol) and (S)-tert-butyl 3-methylpiperazine-1-carboxylate (4.79 g, 24.0 mmol). The reaction mixture was heated at 100° C. for 2 h, then diluted with water and extracted with EtOAc. The organic layer was dried over sodium sulphate and concentrated under reduced pressure. The crude material was purified by silica gel column chromatography, using 3% methanolic ammonia in DCM as eluent. The resulting solid was dissolved in 4M hydrogen chloride in 1,4 dioxane (30 mL) and stirred at r.t. for 3 h. The reaction mixture was evaporated under reduced pressure. The residue was diluted with saturated aqueous sodium bicarbonate solution and extracted with 10% MeOH in DCM. The organic layer was dried over sodium sulphate and concentrated under reduced pressure. The crude residue was purified by silica gel column chromatography, using 4% methanolic ammonia in DCM, to afford the title compound (2.12 g, 77%) as an off-white solid. $\delta_H$ (400 MHz, DMSO-d$_6$) 8.14 (dd, J 5.1, 1.5 Hz, 1H), 6.29 (d, J 1.5 Hz, 1H), 6.21 (dd, J 5.3, 1.5 Hz, 1H), 5.10 (d, J 6.6 Hz, 1H), 3.60 (d, J 12.2 Hz, 1H), 3.39-3.26 (m, 1H), 2.98 (td, J 11.3, 10.4, 3.2 Hz, 2H), 2.83-2.71 (m, 2H), 2.44 (s, 1H), 2.38 (s, 3H), 1.12 (d, J 7.0 Hz, 3H).

Intermediate 36

4-[(2S)-2-Methylpiperazin-1-yl]pyrazolo[1,5-a][1,3,5]triazin-2-amine dihydrochloride Intermediate 27 (80%, 1.24 g, 2.98 mmol) was dissolved in 1,4-dioxane (10 mL) and 4M hydrogen chloride in 1,4-dioxane (10 mL) was added. The mixture was stirred at r.t. for 4 h, over which time a white precipitate had formed. The mixture was concentrated in vacuo, then dried in a vacuum oven for several hours, to give the title compound (1.34 g, 70% purity, quantitative) as a white solid, which was utilised without further purification. LCMS (ES+) [M+H]$^+$ 234, RT 0.76 minutes.

Intermediate 37

8-Methyl-4-[(2S)-2-methylpiperazin-1-yl]pyrazolo[1,5-a][1,3,5]triazin-2-amine dihydrochloride Intermediate 28 (85% pure, 981 mg, 2.4 mmol) was dissolved in 1,4-dioxane (5 mL) and 4M hydrogen chloride in 1,4-dioxane (5 mL) was added. The mixture was stirred at r.t. for 2 h, over which time a cream-coloured precipitate had formed. The mixture was concentrated under vacuum, then dried in a vacuum oven, to afford the title compound (901 mg, 100% yield at 85% purity) as a cream-coloured waxy solid. LCMS (ES+) [M+H]$^+$ 248, RT 0.19 minutes (method 2).

Intermediate 38

Phenyl N-(4-methoxy-2-methylphenyl)carbamate

4-Methoxy-2-methylaniline (0.5 mL, 3.88 mmol) and pyridine (0.34 mL, 4.27 mmol) were dissolved in anhydrous THF (20 mL) and the mixture was cooled to 0° C. in an ice bath. Phenyl chloroformate (0.49 mL, 3.88 mmol) was added dropwise. The mixture was warmed to r.t. and stirred for 1 h, then left to stand at r.t. overnight. Water (30 mL) was added and the mixture was extracted with DCM (2×20 mL). The combined organic layers were washed with brine (20 mL) and dried over sodium sulphate, then concentrated under vacuum, to afford the title compound (988 mg, 99%) as a dark red solid. $\delta_H$ (CDCl$_3$) 7.62 (s, 1H), 7.41 (t, J 7.7 Hz, 2H), 7.24 (m, 3H), 6.85-6.75 (m, 2H), 3.82 (s, 3H), 2.35 (s, 3H).

Intermediate 39

Phenyl N-(6-methoxy-2-methylpyridin-3-yl)carbamate

To a solution of 6-methoxy-2-methylpyridin-3-amine (2.02 g, 13.9 mmol) in DCM (50 mL) were added triethylamine (2.3 mL, 17 mmol) and phenyl chloroformate (1.9 mL, 15 mmol). The mixture was stirred under nitrogen at r.t. overnight, then washed with saturated aqueous sodium bicarbonate solution. The organic layer was separated, and concentrated in vacuo. To the resulting brown oil was added diethyl ether. Following the addition of isohexane, a solid precipitated out of solution, to yield the title compound (2.79 g, 56%) as an off-white/pale pink solid. LCMS (ES+) 259.8 [M+H]+, RT 1.77 minutes (method 3).

Intermediate 40

4-Nitrophenyl N-[2-methyl-4-(trifluoromethoxy)phenyl]carbamate

To a solution of 2-methyl-4-(trifluoromethoxy)aniline (0.50 g, 2.62 mmol) in DCM (3 mL) at r.t. were introduced pyridine (0.62 g, 7.85 mmol) and 4-nitrophenyl chloroformate (0.58 g, 2.88 mmol). After 30 minutes, the reaction mixture was diluted with DCM (50 mL), then washed with 1M aqueous citric acid solution (2×25 mL), 1M aqueous sodium carbonate solution (2×25 mL) and brine (25 mL). The organic phase was dried over sodium sulphate and filtered, then the filtrate was concentrated in vacuo, to furnish the title compound (0.59 g, 57%) as a colourless solid. $\delta_H$ (CDCl$_3$, 500 MHz) 8.30 (d, J 9.1 Hz, 2H), 7.85 (s, 1H), 7.41 (d, J 8.9 Hz, 2H), 7.12 (m, 2H), 6.78 (s, 1H), 2.37 (s, 3H).

Intermediates 41 to 47

To a cooled (ice bath) solution of the appropriate amine (1 mmol) in THF (50 mL) was added pyridine (1.1 equivalents), followed by phenyl chloroformate (1 equivalent) dropwise. The reaction mixture was allowed to warm to room temperature. When LCMS confirmed complete conversion of the amine to the desired carbamate, the reaction mixture was quenched with water. The title compound was then either collected by filtration, or extracted into DCM or EtOAc, phase separated and concentrated in vacuo, and used without further purification.

| | | LCMS Data | |
|---|---|---|---|
| Int. Name | RT | [M + H]+ | Method |
| 41 Phenyl N-[2-methyl-4-(trifluoromethoxy)phenyl]-carbamate | 2.26 | 312 | 3 |
| 42 Phenyl N-(6-ethoxy-2-methylpyridin-3-yl)carbamate | 1.45 | 273 | 3 |
| 43 Phenyl N-[6-(3,3-difluoroazetidin-1-yl)-2-methyl-pyridin-3-yl]carbamate | 1.34 | 320 | 3 |
| 44 Phenyl N-[4-(difluoromethoxy)-2-methylphenyl]-carbamate | 1.45 | 294 | 3 |
| 45 Phenyl N-(2,6-dimethoxy-3-pyridyl)carbamate | 3.14 | 275.2 | 4 |
| 46 Phenyl N-[5-methoxy-6-(trifluoromethyl)pyridin-2-yl]carbamate | 2.14 | 313 | 4 |
| 47 Phenyl N-[6-(azetidin-1-yl)-2-methylpyridin-3-yl]-carbamate | 1.58 | 284 | 4 |

Intermediate 48

Phenyl N-(4-methoxy-3-methylphenyl)carbamate

To a solution of 4-methoxy-3-methylaniline (8 g, 58.39 mmol) in THF (100 mL), maintained at 0° C., was added pyridine (5.8 mL, 72.98 mmol), followed by phenyl chloroformate (7.2 mL, 58.39 mmol). The reaction mixture was stirred at r.t. for 2 h, then quenched with water (50 mL) and extracted with EtOAc (2×100 mL). The organic layer was separated and washed with water (50 mL), then dried over sodium sulfate and concentrated in vacuo, to afford the title compound (13 g, 86%). $\delta_H$ (CDCl$_3$, 400 MHz) 7.45-7.34 (m, 2H), 7.34-7.13 (m, 5H), 6.84 (s, 1H), 3.81 (s, 3H), 2.21 (s, 3H).

Intermediate 49

Phenyl N-[2-chloro-4-(trifluoromethoxy)phenyl]carbamate

To a solution of 2-chloro-4-(trifluoromethoxy)aniline (6.8 g, 32.22 mmol) in THF (100 mL), maintained at 0° C., was added pyridine (3.2 mL, 40.28 mmol), followed by phenyl chloroformate (4 mL, 32.22 mmol). The reaction mixture was stirred at r.t. for 3 h, then quenched with water (50 mL) and extracted with EtOAc (2×50 mL). The organic layer was separated and washed with water (50 mL), then dried over anhydrous sodium sulfate and concentrated in vacuo. The crude residue was purified by column chromatography (normal phase; silica gel 100-200 mesh; 2% EtOAc in hexanes) to afford the title compound (10 g, 94%). $\delta_H$ (DMSO-d$_6$, 400 MHz) 9.87 (s, 1H), 7.76 (d, J 8.9 Hz, 1H), 7.65 (s, 1H), 7.44-7.38 (m, 3H), 7.29-7.18 (m, 3H).

Intermediate 50 tert-Butyl (3S)-4-[8-chloro-2-(methylsulfanyl)pyrazolo[1,5-a][1,3,5]triazin-4-yl]-3-ethylpiperazine-1-carboxylate To a solution of Intermediate 13 (1 g, 4.61 mmol) in POCl$_3$ (13 mL, 139.17 mmol) was added N,N-dimethylaniline (0.274 g, 2.26 mmol). The reaction mixture was heated at 110° C. for 6 h, then concentrated in vacuo. The solid obtained was triturated in pentane. To a stirred solution of the unpurified residue (1.3 g, 5.57 mmol) in THF (40 mL) were added triethylamine (6.43 mL, 46.15 mmol) and tert-butyl (3S)-3-ethylpiperazine-1-carboxylate (1.08 g, 5.08 mmol). The reaction mixture was stirred at r.t. for 12 h, then concentrated in vacuo. The residue was dissolved in EtOAc (50 mL). The organic layer was washed with water (50 mL), then dried over anhydrous sodium sulfate and concentrated in vacuo. The crude residue was purified by column chromatography (normal phase; silica gel: 100-200 mesh; 2% EtOAc in hexanes) to afford the title compound (0.62 g, 33%). $\delta_H$ (CDCl$_3$, 400 MHz) 7.82 (s, 1H), 4.22-4.10 (m, 2H), 3.40-3.30 (m, 2H), 3.22-3.10 (m, 3H), 2.58 (s, 3H), 1.84-1.74 (m, 2H), 1.48 (s, 9H), 0.98-0.80 (m, 3H). LCMS (ES+) [M+H]+ 413.45, RT 4.20 minutes (method 4).

Intermediate 51 tert-Butyl (3S)-4-[8-chloro-2-(methylsulfonyl)pyrazolo[1,5-a][1,3,5]triazin-4-yl]-3-ethylpiperazine-1-carboxylate To a stirred solution of Intermediate 50 (0.62 g, 1.58 mmol) in DCM (15 mL) was added MCPBA (0.51 g, 3.16 mmol). The reaction mixture was stirred at r.t. for 14 h, then concentrated in vacuo. The residue was dissolved in EtOAc (50 mL). The organic layer was washed with saturated aqueous sodium hydrogen carbonate solution and water (50 mL), then dried over anhydrous sodium sulfate. The organic layer was concentrated in vacuo. The crude residue was triturated with pentane to afford the title compound (0.66 g), which was utilised without further purification. $\delta_H$ (CDCl$_3$, 400 MHz) 8.00 (s, 1H), 5.18-4.80 (m, 1H), 4.22-4.10 (m, 2H), 3.60-3.50 (m, 1H), 3.40 (s, 3H), 3.30-3.05 (m, 3H), 1.97-1.80 (m, 2H), 1.51 (s, 9H), 1.08-0.88 (m, 3H). LCMS (ES+) [M+H]$^+$ 445.10, RT 2.76 minutes (method 4).

Intermediate 52 tert-Butyl (3S)-4-(2-amino-8-chloropyrazolo[1,5-a][1,3,5]triazin-4-yl)-3-ethylpiperazine-1-carboxylate To a stirred solution of Intermediate 51 (0.65 g, 1.46 mmol) in 1,4-dioxane (10 mL) was added ammonium hydroxide (3.29 mL, 94.00 mmol). The reaction mixture was heated at 80° C. for 4 h, then concentrated in vacuo. The residue was dissolved in EtOAc (50 mL). The organic layer was washed with water (50 mL) and separated, then dried with anhydrous sodium sulfate and concentrated in vacuo. The solid obtained was triturated with pentene to afford the title compound (0.4 g, 72%). $\delta_H$ (DMSO-d$_6$, 400 MHz) 7.96 (s, 1H), 6.84 (s, 2H), 4.02-3.90 (m, 3H), 3.20-2.94 (m, 4H), 1.74-1.60 (m, 2H), 1.44 (s, 9H), 0.95-0.80 (m, 3H). LCMS (ES+) [M+H]$^+$ 382.4, RT 3.17 minutes (method 4).

Intermediate 53

8-Chloro-4-[(2S)-2-ethylpiperazin-1-yl]pyrazolo[1,5-a][1,3,5]triazin-2-amine dihydrochloride To a stirred solution of Intermediate 52 (0.37 g, 0.96 mmol) in 1,4-dioxane (1 mL) was added 4M hydrogen chloride in 1,4-dioxane (6 mL). The reaction mixture was stirred at r.t. for 1 h, then the volatiles were removed in vacuo. The residue was triturated in diethyl ether (25 mL) to afford the title compound (0.3 g, crude). $\delta_H$ (DMSO-d$_6$, 400 MHz) 9.70 (s, 1H), 9.36 (s, 1H), 8.02 (s, 1H), 5.60-5.20 (s, 3H), 3.50-3.10 (m, 7H), 2.04-1.92 (m, 2H), 0.95-0.80 (m, 3H). LCMS (ES+) [M+H]$^+$ 282.3, RT 1.67 minutes (method 4).

Intermediate 54 tert-Butyl (3S)-3-ethyl-4-[8-methyl-2-(methylsulfanyl)pyrazolo[1,5-a][1,3,5]-triazin-4-yl]piperazine-1-carboxylate Intermediate 16 (80% purity, 2.67 g, 9.95 mmol) was dissolved in THF (50 mL) and DIPEA (17.5 mL, 100.47 mmol) was added. tert-Butyl (3S)-3-ethylpiperazine-1-carboxylate (2.22 g, 10.36 mmol) was added and the reaction mixture was stirred at r.t. for approximately 60 h. The reaction mixture was concentrated in vacuo and the residue was partitioned between EtOAc (100 mL) and water (50 mL). The organic phase was washed with brine (50 mL), dried with anhydrous sodium sulfate and concentrated in vacuo. The residue was purified by flash column chromatography on silica (gradient elution with 0-20% EtOAc/heptane) to afford the title compound (3.2 g, 77.9%) as a yellow gum. $\delta_H$ (CDCl$_3$, 400 MHz) 7.71 (s, 1H), 5.58 (br s, 2H), 4.30-4.00 (m, 2H), 3.36 (t, J 11.9 Hz, 1H), 3.15 (br s, 1H), 2.98 (br s, 1H), 2.55 (s, 3H), 2.20 (s, 3H), 1.82-1.70 (m, 2H), 1.49 (s, 9H), 0.92 (t, J 6.7 Hz, 3H).

Intermediate 55 tert-Butyl (3S)-3-ethyl-4-[8-methyl-2-(methylsulfonyl)pyrazolo[1,5-a][1,3,5]-triazin-4-yl]piperazine-1-carboxylate Intermediate 54 (3.2 g, 8.15 mmol) was dissolved in DCM (120 mL) and MCPBA (70%, 4.02 g, 16.3 mmol) was added. The mixture was stirred at r.t. for 2 h, then washed with 2M aqueous sodium hydroxide solution (2×50 mL), followed by water (50 mL) and brine (50 mL). The organic layer was dried with anhydrous sodium sulfate and concentrated in vacuo to afford the title compound (3.32 g, 95.8%) as a yellow solid. $\delta_H$ (CDCl$_3$, 500 MHz) 7.91 (s, 1H), 6.64-5.94 (m, 1H), 5.17-4.68 (m, 1H), 4.39-3.93 (m, 2H), 3.65-3.33 (m, 1H), 3.32 (s, 3H), 3.18 (br s, 1H), 3.03 (br s, 1H), 2.28 (s, 3H), 1.81 (p, J 7.2 Hz, 2H), 1.49 (s, 9H), 0.95 (br s, 3H).

Intermediate 56 tert-Butyl (3S)-4-(2-amino-8-methylpyrazolo[1,5-a][1,3,5]triazin-4-yl)-3-ethylpiperazine-1-carboxylate To a stirred solution of Intermediate 55 (0.5 g, 1.17 mmol) in 1,4-dioxane (3 mL) was added ammonium hydroxide (3.5 mL). The reaction mixture was heated at 100° C. in a sealed tube for 5 h, then concentrated in vacuo, to afford the title compound (500 mg, crude) which was used without further purification. LCMS (ES+) [M+H]$^+$ 262.2, RT 2.09 minutes (method 4).

Intermediate 57

4-[(2S)-2-Ethylpiperazin-1-yl]-8-methylpyrazolo[1,5-a][1,3,5]triazin-2-amine dihydrochloride To a stirred solution of Intermediate 56 (0.5 g, 1.38 mmol) in 1,4-dioxane (5 mL) was added 4M hydrogen chloride in 1,4-dioxane (4 mL) at 0° C. The reaction mixture was stirred at r.t. for 16 h, then concentrated in vacuo. The solid obtained was triturated using pentane and diethyl ether to afford the title compound (0.6 g, crude). LCMS (ES+) [M+H]$^+$ 261.3, RT 0.35 minutes (method 4).

Intermediate 58 tert-Butyl (3S)-3-ethyl-4-[2-(methylsulfanyl)pyrazolo[1,5-a][1,3,5]triazin-4-yl]-piperazine-1-carboxylate Prepared from Intermediate 9 (5.1 g, 28 mmol) and tert-butyl (3S)-3-ethylpiperazine-1-carboxylate by applying the procedure described for Intermediate 19. Purification by silica gel chromatography (gradient of 0-20% EtOAc in isohexane) afforded the title compound (8.26 g, 78%) as a yellow oil. LCMS (ES+) [M+H]$^+$ 379, RT 1.64 minutes (method 3).

Intermediate 59 tert-Butyl (3S)-4-(2-aminopyrazolo[1,5-a][1,3,5]triazin-4-yl)-3-ethylpiperazine-1-carboxylate MCPBA (70%, 7.62 g, 30.9 mmol) was added slowly, portionwise, to a solution of Intermediate 58 (5.85 g, 15.5 mmol) in DCM (100 mL) at 0° C. The reaction mixture was allowed to warm to r.t. and was stirred for 4 h. The reaction mixture was washed with saturated aqueous sodium hydrogen carbonate solution (4×100 mL), then passed through a phase separator cartridge and evaporated. The resulting pale yellow foaming gum was dissolved in 1,4-dioxane (35 mL) and treated with aqueous ammonium hydroxide solution (28%, 35 mL). The reaction mixture was heated at 100° C. for 3.5 h in a pressure vessel, then allowed to cool to r.t. and concentrated in vacuo. The resulting brown hygroscopic gum was partitioned between EtOAc (50 mL) and water (50 mL), then separated. The organic phase was dried with anhydrous sodium sulfate and evaporated. The crude residue was purified by silica gel chromatography (gradient of 25-75% EtOAc in isohexane) to afford the title compound (2.47 g, 47%) as a yellow viscous gum. LCMS (ES+) [M+H]$^+$ 348, RT 1.44 minutes (method 3).

Intermediate 60

4-[(2S)-2-Ethylpiperazin-1-yl]pyrazolo[1,5-a][1,3,5]triazin-2-amine hydrochloride Prepared from Intermediate 59 (1.89 g, 5.44 mmol), by applying the procedure described for Intermediate 33, to afford the title compound (1.74 g, quantitative) as a yellow powder, which was utilised without further purification. LCMS (ES+) [M+H]$^+$ 248, RT 0.99 minutes (method 3).

Example 1

(3S)—N-(4-Methoxy-2-methylphenyl)-3-methyl-4-[2-(methylsulfanyl)pyrazolo[1,5-a]-[1,3,5]triazin-4-yl]piperazine-1-carboxamide To a solution of Intermediate 19 (60 mg, 0.16 mmol) in DCM (1 mL) was added TFA (1 mL). The reaction mixture was stirred at r.t., then the solvents were evaporated in vacuo. The crude residue was dissolved in DCM (3 mL), then DIPEA (272 µL, 1.6 mmol) and 4-methoxy-2-methylbenzene isocyanate (23 µL, 0.17 mmol) were added at r.t. The reaction mixture was stirred overnight, then the solvents were evaporated in vacuo. The residue was purified by flash chromatography, the mobile phase being a mixture of EtOAc and cyclohexane (in a ratio gradually decreasing from 30% to 10% cyclohexane in EtOAc), yielding the title compound (51 mg, 74.6%) as a yellow powder. $^{13}$C NMR δ (CDCl$_3$, 75 MHz) 166.51, 156.94, 156.12, 151.88, 147.46, 144.39, 133.74, 129.21, 126.55, 115.49, 111.27, 93.14, 55.06, 49.99, 47.27, 43.56, 40.53, 17.86, 15.66, 13.79. MS (m/z) 428 [M+H]$^+$.

Example 2

(3S)—N-(4-Methoxy-2-methylphenyl)-4-(2-methoxypyrazolo[1,5-a][1,3,5]triazin-4-yl)-3-methylpiperazine-1-carboxamide To a solution of Example 1 (50 mg, 0.12 mmol) in DCM (3 mL) was added MCPBA (70 mg, 0.28 mmol) at 0° C. The reaction mixture was stirred for 4 h at r.t. To the reaction mixture was added 1N aqueous sodium sulfite solution (1 mL), whereupon the reaction mixture was extracted with DCM and 2N aqueous sodium hydroxide solution, followed by brine. The solvents were dried over magnesium sulfate and removed in vacuo. The residue was dissolved in MeOH (2 mL) and sodium methoxide (30 wt % solution) (28 µL, 0.15 mmol) was added. The reaction mixture was stirred at r.t. for 2 h, then evaporated in vacuo. The residue was purified by flash chromatography, the mobile phase being a mixture of EtOAc and cyclohexane (in a ratio gradually decreasing from 40% to 20% cyclohexane in EtOAc), yielding the title compound (38 mg, 77%) as a yellow powder. $^{13}$C NMR δ (DMSO-d$_6$, 75 MHz) 160.99, 156.83, 156.21, 153.08, 149.98, 145.51, 135.67, 130.69, 128.18, 115.31, 111.17, 92.82, 55.23, 54.46, 50.14, 47.23, 43.43, 40.90 18.18, 15.51. MS (m/z) 412 [M+H]$^+$.

Example 3

(3S)-4-(2-Aminopyrazolo[1,5-a][1,3,5]triazin-4-yl)-N-(4-methoxy-2-methylphenyl)-3-methylpiperazine-1-carboxamide Method 1

To a solution of Intermediate 19 (50 mg, 0.14 mmol) in DCM (3 mL) was added MCPBA (70 mg, 0.28 mmol) at 0° C. The reaction mixture was stirred for 4 h at r.t. To the mixture was added 1N aqueous sodium sulfite solution (1 mL), whereupon the reaction mixture was extracted with DCM and 2N aqueous sodium hydroxide solution, followed by brine. The solvents were dried over magnesium sulfate and removed in vacuo. The residue was dissolved in 1,4-dioxane (2 mL) and ammonium hydroxide (2 mL). The reaction mixture was stirred in a sealed vessel at 100° C. for 2 h. The solvents were evaporated in vacuo. The residue was dissolved in CHCl$_3$ (3 mL) and trimethylsilyl iodide (59 µL, 0.41 mmol) was added at r.t. After completion of the reaction, MeOH (1 mL) was added and the solvents were evaporated in vacuo. The residue was dissolved in DCM (2 mL), then DIPEA (227 µL, 1.4 mmol) and 4-methoxy-2-methylphenyl isocyanate (19 µL, 0.144 mmol) were added. The reaction mixture was stirred at r.t. for 2 h, whereupon the mixture was evaporated in vacuo. The residue was purified by flash chromatography, the mobile phase being a mixture of NH$_3$ in MeOH (7N) and DCM (in a ratio gradually increasing from 2% to 4% NH$_3$/MeOH in DCM), yielding the title compound (21 mg, 38%) as a yellow powder. $^{13}$C NMR δ (DMSO-d$_6$, 75 MHz) 158.33, 156.85, 156.25, 154.09, 149.28, 144.73, 135.73, 130.69, 128.21, 115.27, 111.10, 89.30, 55.17, 49.44, 47.45, 43.55, 40.52, 18.16, 14.15. MS (m/z) 397 [M+H]$^+$.

Method 2

Intermediate 36 (70%, 200 mg, 0.46 mmol) was suspended in acetonitrile (20 mL) and DIPEA (0.4 mL, 2.29 mmol) was added, followed by Intermediate 38 (124 mg, 0.48 mmol). The solution was stirred at r.t. for 18 h. The mixture was concentrated in vacuo, then partitioned between DCM (50 mL) and water (50 mL). The organic layer was dried (sodium sulfate), filtered and concentrated in vacuo. The residue was purified by reverse phase Biotage (30 g), using acetonitrile (containing 0.1% formic acid) and water (containing 0.1% formic acid) as eluent, to give the title compound (36.3 mg, 20%) as a white solid. δ$_H$ (500 MHz, DMSO-d$_6$) 8.00 (s, 1H), 7.83 (d, J 2.1 Hz, 1H), 7.02 (d, J 8.6 Hz, 1H), 6.78 (d, J 2.8 Hz, 1H), 6.70 (dd, J 8.6, 2.9 Hz, 1H), 6.52 (s, 2H), 5.76 (d, J 2.1 Hz, 1H), 5.72-5.40 (m, 1H), 5.32-4.89 (m, 1H), 4.12 (d, J 13.0 Hz, 1H), 3.96 (d, J 13.5 Hz, 1H), 3.72 (s, 3H), 3.51-3.40 (m, 1H), 3.28 (d, J 3.7 Hz, 1H), 3.09 (td, J 12.8, 3.3 Hz, 1H), 2.14 (s, 3H), 1.30 (d, J 6.7 Hz, 3H). LCMS (ES+) [M+H]$^+$ 397, RT 1.69 minutes (method 1).

Example 4

(3S)-4-(2-Aminopyrazolo[1,5-a][1,3,5]triazin-4-yl)-3-methyl-N-[2-methyl-4-(trifluoro-methoxy)phenyl]piperazine-1-carboxamide Intermediate 36 (70%, 120 mg, 0.27 mmol) was suspended in acetonitrile (20 mL) and DIPEA (0.4 mL, 2.29 mmol) was added, followed by Intermediate 40 (103 mg, 0.29 mmol). The solution was stirred at r.t. for 18 h. The mixture was concentrated in vacuo, then partitioned between DCM (50 mL) and water (50 mL). The organic layer was dried (sodium sulfate), filtered and concentrated in vacuo. The residue was purified by flash column chromatography (Isolera 4, SNAP 25 g), using 0-100% EtOAc in heptane as eluent, to yield the title compound (27.6 mg, 22%) as a white solid. $\delta_H$ (500 MHz, DMSO-$d_6$) 8.19 (s, 1H), 7.83 (d, J 2.1 Hz, 1H), 7.29 (d, J 8.7 Hz, 1H), 7.21 (s, 1H), 7.14 (d, J 8.5 Hz, 1H), 6.49 (s, 2H), 5.76 (d, J 2.1 Hz, 1H), 5.62-5.40 (m, 1H), 5.30-4.87 (m, 1H), 4.12 (d, J 12.9 Hz, 1H), 3.96 (d, J 13.0 Hz, 1H), 3.52-3.44 (m, 1H), 3.36 (d, J 4.0 Hz, 1H), 3.16 (td, J 12.6, 3.4 Hz, 1H), 2.21 (s, 3H), 1.31 (d, J 6.7 Hz, 3H). LCMS (ES+) [M+H]$^+$ 451, RT 2.34 minutes (method 1).

Example 5

(3S)-4-(2-Aminopyrazolo[1,5-a][1,3,5]triazin-4-yl)-N-(6-ethoxy-2-methylpyridin-3-yl)-3-methylpiperazine-1-carboxamide Intermediate 36 (70%, 200 mg, 0.46 mmol) was suspended in acetonitrile (20 mL) and DIPEA (0.4 mL, 2.29 mmol) was added, followed by Intermediate 42 (1.30 g, 0.48 mmol). The solution was stirred at r.t. for 18 h. The mixture was concentrated in vacuo, then partitioned between DCM (50 mL) and water (50 mL). The organic layer was dried (sodium sulfate), filtered and concentrated in vacuo. The residue was purified by reverse phase Biotage (60 g), using acetonitrile (containing 0.1% formic acid) and water (containing 0.1% formic acid) as eluent, to give the title compound (45.7 mg, 24%) as a white solid. $\delta_H$ (500 MHz, DMSO-$d_6$) 8.13 (s, 1H), 7.83 (d, J 2.1 Hz, 1H), 7.41 (d, J 8.6 Hz, 1H), 6.57 (d, J 8.5 Hz, 1H), 6.52 (s, 2H), 5.76 (d, J 2.1 Hz, 1H), 5.72-5.36 (m, 1H), 5.30-4.81 (m, 1H), 4.25 (q, J 7.0 Hz, 2H), 4.12 (d, J 12.5 Hz, 1H), 3.96 (d, J 13.4 Hz, 1H), 3.53-3.41 (m, 1H), 3.31-3.26 (m, 1H), 3.12 (td, J 12.9, 3.7 Hz, 1H), 2.26 (s, 3H), 1.35-1.26 (m, 6H). LCMS (ES+) [M+H]$^+$ 412, RT 1.49 minutes (method 1).

Example 6

(3S)-4-(2-Amino-8-methylpyrazolo[1,5-a][1,3,5]triazin-4-yl)-N-[6-(3,3-difluoroazetidin-1-yl)-2-methylpyridin-3-yl]-3-methylpiperazine-1-carboxamide Prepared from Intermediate 20 (63 mg, 0.17 mmol) and Intermediate 43 (59 mg, 0.18 mmol) applying the procedure for Example 3, Method 1. The title compound (55.7 mg, 69%) was isolated as a yellow powder. $^{13}$C NMR $\delta$ (CDCl$_3$, 75 MHz) 157.01, 156.64 (t, $J_{CF}$ 2.9 Hz), 155.71, 150.72, 150.06, 149.37, 145.44, 135.02, 124.07, 115.92 (t, $J_{CF}$ 273.0 Hz), 104.37, 98.99, 62.17 (2C, t, $J_{CF}$ 26.0 Hz), 49.47, 47.39, 43.72, 40.16, 20.25, 15.58, 6.86. MS (m/z) 473 [M+H]$^+$.

Example 7

(3S)-4-(2-Amino-8-methylpyrazolo[1,5-a][1,3,5]triazin-4-yl)-N-(4-methoxy-2-methyl-phenyl)-3-methylpiperazine-1-carboxamide Intermediate 37 (85% pure, 200 mg, 0.53 mmol) was suspended in acetonitrile (15 mL) and DIPEA (0.32 mL, 1.86 mmol) was added, followed by Intermediate 38 (143.4 mg, 0.56 mmol). The mixture was stirred for 18 h. The mixture was concentrated under vacuum and water (15 mL) was added to the residue. The mixture was extracted with 3:1 chloroform:isopropanol (2×20 mL). The combined organic layers were dried over sodium sulfate and concentrated under vacuum. The residue was purified by preparative HPLC (acidic method) to afford the title compound (53 mg, 24%) as a pale pink solid. $\delta_H$ (DMSO-$d_6$) 7.98 (s, 1H), 7.70 (s, 1H), 7.03 (d, J 8.6 Hz, 1H), 6.78 (d, J 2.9 Hz, 1H), 6.71 (dd, J 8.6, 2.9 Hz, 1H), 6.46 (s, 2H), 5.58 (br s, 1H), 5.05 (br s, 1H), 4.11 (d, J 13.4 Hz, 1H), 3.96 (d, J 13.6 Hz, 1H), 3.72 (s, 3H), 3.47-3.39 (m, 1H), 3.31-3.26 (m, 1H), 3.13-3.05 (m, 1H), 2.14 (s, 3H), 1.99 (s, 3H), 1.29 (d, J 6.7 Hz, 3H). LCMS (ES+) [M+H]$^+$ 411, RT 1.84 minutes (method 1).

Example 8

(3S)-4-(2-Amino-8-methylpyrazolo[1,5-a][1,3,5]triazin-4-yl)-3-methyl-N-[2-methyl-4-(trifluoromethoxy)phenyl]piperazine-1-carboxamide Intermediate 37 (85% pure, 200 mg, 0.53 mmol) was suspended in acetonitrile (15 mL) and DIPEA (0.37 mL, 2.12 mmol) was added, followed by Intermediate 40 (198.6 mg, 0.56 mmol). The mixture was stirred at r.t. for 18 h. The mixture was concentrated under vacuum and water (15 mL) was added to the residue. The mixture was extracted with 3:1 chloroform:isopropanol (2×20 mL). The combined organic layers were dried over sodium sulfate and concentrated under vacuum. The residue was purified by preparative HPLC (acidic method). The resulting yellow gum (approximately 80 mg) was further purified by flash column chromatography, eluting with a gradient of 0-100% EtOAc in heptane, to afford the title compound (35 mg, 14%) as a cream-coloured solid. $\delta_H$ (DMSO-$d_6$) 8.19 (s, 1H), 7.71 (s, 1H), 7.30 (d, J 8.7 Hz, 1H), 7.22 (br s, 1H), 7.14 (dd, J 8.8, 1.7 Hz, 1H), 6.47 (s, 2H), 5.59 (br s, 1H), 5.10 (br s, 1H), 4.12 (d, J 13.3 Hz, 1H), 3.97 (d, J 13.3 Hz, 1H), 3.51-3.41 (m, 1H), 3.35 (d, J 3.7 Hz, 1H), 3.19-3.11 (m, 1H), 2.22 (s, 3H), 1.99 (s, 3H), 1.30 (d, J 6.7 Hz, 3H). LCMS (ES+) [M+H]$^+$ 465, RT 2.43 minutes (method 1).

Example 9

(3S)-4-(2-Amino-8-methylpyrazolo[1,5-a][1,3,5]triazin-4-yl)-N-(6-ethoxy-2-methylpyridin-3-yl)-3-methylpiperazine-1-carboxamide formate Intermediate 37 (85% pure, 200 mg, 0.53 mmol) was suspended in acetonitrile (15 mL) and DIPEA (0.32 mL, 1.86 mmol) was added, followed by Intermediate 42 (151.8 mg, 0.56 mmol). The mixture was stirred at r.t. for 18 h. The mixture was concentrated under vacuum and water (15 mL) was added to the residue. The mixture was extracted with 3:1 chloroform:isopropanol (2×20 mL). The combined organic layers were dried over sodium sulfate and concentrated under vacuum. The residue was purified by preparative HPLC (acidic method) to afford the title compound (78 mg, 31%) as a white solid. $\delta_H$ (DMSO-$d_6$) 8.16 (s, 1H), 8.12 (s, 1H), 7.71 (s, 1H), 7.41 (d, J 8.6 Hz, 1H), 6.58 (d, J 8.5 Hz, 1H), 6.46 (s, 2H), 5.58 (br s, 1H), 5.08 (br s, 1H), 4.26 (q, J 7.0 Hz, 2H), 4.12 (d, J 12.1 Hz, 1H), 3.96 (d, J 13.8 Hz, 1H), 3.15-3.08 (m, 1H), 2.27 (s, 3H), 1.99 (s, 3H), 1.32-1.29 (m, 6H). Note that two protons have not been assigned as the signals are not visible. LCMS (ES+) [M+H]$^+$ 426, RT 1.70 minutes (method 1).

Example 10

(3S)-4-(2-Amino-7-methylpyrazolo[1,5-a][1,3,5]triazin-4-yl)-N-(4-methoxy-2-methyl-phenyl)-3-methylpiperazine-1-carboxamide Prepared from Intermediate 21 (50 mg, 0.13 mmol) applying the procedure for Example 3, Method 1. The title compound (19 mg, 36%) was isolated as a yellow powder. $^{13}$C NMR δ (DMSO-d$_6$, 75 MHz) 161.27, 158.27, 156.81, 154.67, 153.77, 148.88, 135.67, 130.72, 128.22, 115.28, 111.15, 89.35, 55.23, 49.16, 47.38, 44.37, 43.49, 18.20, 15.33, 14.53. MS (m/z) 411 [M+H]$^+$.

Example 11

(3S)-4-[2-Amino-7-(4-fluorophenyl)pyrazolo[1,5-a][1,3,5]triazin-4-yl]-N-(4-methoxy-2-methylphenyl)-3-methylpiperazine-1-carboxamide Prepared from Intermediate 22 (55 mg, 0.12 mmol) applying the procedure for Example 3, Method 1. The title compound (24 mg, 37%) was isolated as a yellow powder. $^{13}$C NMR δ (DMSO-d$_6$, 75 MHz) 162.72 (d, J$_{CF}$ 244.2 Hz), 158.46, 156.80, 156.26, 155.28, 153.57, 149.13, 135.62, 130.75, 129.31 (d, J$_{CF}$ 3.1 Hz), 128.29 (2C, d, J$_{CF}$ 8.4 Hz), 128.19, 115.78 (2C, d, J$_{CF}$ 21.5 Hz), 115.30, 111.16, 86.69, 55.24, 49.68, 47.40, 43.60, 40.63, 18.21, 15.61. MS (m/z) 491 [M+H]$^+$.

Example 12

(3S)-4-[2-Amino-7-(4-fluorophenyl)pyrazolo[1,5-a][1,3,5]triazin-4-yl]-N-[6-(3,3-difluoroazetidin-1-yl)-2-methylpyridin-3-yl]-3-methylpiperazine-1-carboxamide Prepared from Intermediate 22 (55 mg, 0.12 mmol) and Intermediate 43 (42 mg, 0.13 mmol) applying the procedure for Example 3, Method 1. The title compound (22 mg, 33%) was isolated as a yellow powder. $^{13}$C NMR δ (DMSO-d$_6$, 75 MHz) 162.72 (d, J$_{CF}$ 244.1 Hz), 158.46, 156.86 (t, J$_{CF}$ 2.8 Hz), 156.21, 155.28, 153.58, 152.83, 149.12, 137.11, 129.30 (d, J$_{CF}$ 2.9 Hz), 128.23 (2C, d, J$_{CF}$ 8.2 Hz), 125.65, 117.13 (t, J$_{CF}$ 272.2 Hz), 115.38 (2C, d, J$_{CF}$ 21.6 Hz), 104.80, 86.67, 62.15 (2C, t, J$_{CF}$ 25.2 Hz), 49.63, 47.40, 43.60, 40.50, 20.84, 15.57. MS (m/z) 553 [M+H]$^+$.

Example 13

(3S)-4-(2-Amino-8-chloropyrazolo[1,5-a][1,3,5]triazin-4-yl)-N-(4-methoxy-2-methyl-phenyl)-3-methylpiperazine-1-carboxamide Intermediate 32 (95% pure, 115 mg, 0.32 mmol) was suspended in acetonitrile (10 mL) and DIPEA (0.2 mL, 1.12 mmol) was added, followed by Intermediate 38 (86.6 mg, 0.34 mmol). The solution was stirred at r.t. for 18 h. The mixture was concentrated under vacuum, then partitioned between DCM (30 mL) and water (15 mL). The organic layer was dried over sodium sulfate and concentrated under vacuum. The residue was purified by flash column chromatography, eluting with a gradient of 0-100% EtOAc in heptane, to afford the title compound (54.2 mg, 39%) as a pink solid. δ$_H$ (DMSO-d$_6$) 7.99 (s, 1H), 7.97 (s, 1H), 7.03 (d, J 8.6 Hz, 1H), 6.85 (s, 2H), 6.78 (d, J 2.9 Hz, 1H), 6.71 (dd, J 8.6, 2.9 Hz, 1H), 5.47 (br s, 1H), 5.05 (br s, 1H), 4.11 (d, J 13.7 Hz, 1H), 3.96 (d, J 13.5 Hz, 1H), 3.73 (s, 3H), 3.49-3.45 (m, 1H), 3.17-3.07 (m, 1H), 2.14 (s, 3H), 1.32 (d, J 6.7 Hz, 3H). Note that one proton has not been assigned as the signal is not visible. LCMS (ES+) [M+H]$^+$ 431, RT 2.58 minutes (method 1).

Example 14

(3S)-4-(2-Amino-8-chloro pyrazolo[1,5-a][1,3,5]triazin-4-yl)-3-methyl-N-[2-methyl-4-(trifluoromethoxy)phenyl]piperazine-1-carboxamide Intermediate 32 (95% pure, 115 mg, 0.32 mmol) was suspended in acetonitrile (10 mL) and DIPEA (0.2 mL, 1.12 mmol) was added, followed by Intermediate 40 (120 mg, 0.34 mmol). The solution was stirred at r.t. for 18 h. The mixture was concentrated under vacuum, then partitioned between DCM (30 mL) and water (15 mL). The organic layer was dried over sodium sulfate and concentrated under vacuum. The residue was purified by flash column chromatography, eluting with a gradient of 0-100% TBME in heptane. The resulting colourless glass (56.6 mg; 88% pure by LCMS) was further purified by preparative HPLC (acidic method) to afford the title compound (45.1 mg, 29%) as a white solid. δ$_H$ (DMSO-d$_6$) 8.19 (s, 1H), 7.97 (s, 1H), 7.29 (d, J 8.7 Hz, 1H), 7.21 (d, J 2.2 Hz, 1H), 7.13 (dd, J 9.0, 2.1 Hz, 1H), 6.85 (s, 2H), 5.49 (br s, 1H), 5.01 (br s, 1H), 4.11 (d, J 12.3 Hz, 1H), 3.95 (d, J 13.4 Hz, 1H), 3.57-3.44 (m, 1H), 3.38-3.35 (m, 1H), 3.19-3.14 (m, 1H), 2.20 (s, 3H), 1.32 (d, J 6.7 Hz, 3H). LCMS (ES+) [M+H]$^+$ 485, RT 3.30 minutes (method 1).

Example 15

(3S)-4-(2-Amino-8-chloropyrazolo[1,5-a][1,3,5]triazin-4-yl)-N-(6-ethoxy-2-methylpyridin-3-yl)-3-methylpiperazine-1-carboxamide Intermediate 32 (95% pure, 115 mg, 0.32 mmol) was suspended in acetonitrile (10 mL) and DIPEA (0.2 mL, 1.12 mmol) was added, followed by Intermediate 42 (91.7 mg, 0.34 mmol). The solution was stirred at r.t. for 18 h. The mixture was concentrated under vacuum, then partitioned between DCM (30 mL) and water (15 mL). The organic layer was dried over sodium sulfate and concentrated under vacuum. The residue was purified by preparative HPLC (acidic method) to afford the title compound (41 mg, 29%) as a white solid. δ$_H$ (DMSO-d$_6$) 8.12 (s, 1H), 7.97 (s, 1H), 7.41 (d, J 8.6 Hz, 1H), 6.86 (s, 2H), 6.58 (d, J 8.5 Hz, 1H), 5.49 (br s, 1H), 5.04 (br s, 1H), 4.26 (q, J 7.0 Hz, 2H), 4.11 (d, J 13.9 Hz, 1H), 3.96 (d, J 13.9 Hz, 1H), 3.51-3.46 (m, 1H), 3.19-3.09 (m, 1H), 2.27 (s, 3H), 1.34-1.28 (m, 6H). Note that one proton has not been assigned as the signal is not visible. LCMS (ES+) [M+H]$^+$ 446, RT 2.31 minutes (method 1).

Example 16

(3S)—N-(4-Methoxy-2-methylphenyl)-3-methyl-4-(3-methylpyrazolo[1,5-a]pyrimidin-7-yl)piperazine-1-carboxamide Intermediate 33 (63 mg, 0.24 mmol) and DIPEA (0.12 mL, 0.71 mmol) were dissolved in acetonitrile (5 mL) and Intermediate 38 (64 mg, 0.25 mmol) was added. The mixture was stirred at r.t. for 18 h. The mixture was concentrated under vacuum, then partitioned between DCM (30 mL) and water (20 mL). The organic layer was concentrated under vacuum and the residue was purified by flash column chromatography, eluting with a gradient of 0-5% MeOH in DCM, to afford the title compound (69 mg, 74%) as a pale pink solid. $\delta_H$ (DMSO-d$_6$) 8.57 (d, J 7.9 Hz, 1H), 7.98 (s, 1H), 7.72 (s, 1H), 7.03 (d, J 8.6 Hz, 1H), 6.81-6.60 (m, 3H), 4.60 (m, 1H), 4.25-4.10 (m, 2H), 4.00 (d, J 13.4 Hz, 1H), 3.72 (s, 3H), 3.25-3.17 (m, 2H), 3.08-2.97 (m, 1H), 2.14 (s, 3H), 2.10 (s, 3H), 1.18 (d, J 6.5 Hz, 3H). LCMS (ES+) [M+H]$^+$ 395, RT 2.79 minutes (method 1).

Example 17

(3S)—N-(6-Ethoxy-2-methylpyridin-3-yl)-3-methyl-4-(3-methylpyrazolo[1,5-a]pyrimidin-7-yl)piperazine-1-carboxamide Intermediate 33 (63 mg, 0.24 mmol) and DIPEA (0.12 mL, 0.71 mmol) were dissolved in acetonitrile (5 mL) and Intermediate 42 (68 mg, 0.25 mmol) was added. The mixture was stirred at r.t. for 18 h. The mixture was concentrated under vacuum, then partitioned between DCM (30 mL) and water (20 mL). The organic layer was concentrated under vacuum and the residue was purified by flash column chromatography, eluting with a gradient of 0-5% MeOH in DCM, to afford the title compound (79 mg, 82%) as a white solid. $\delta_H$ (DMSO-d$_6$) 8.58 (d, J 7.9 Hz, 1H), 8.12 (s, 1H), 7.72 (s, 1H), 7.41 (d, J 8.6 Hz, 1H), 6.65 (d, J 7.9 Hz, 1H), 6.57 (d, J 8.5 Hz, 1H), 4.64 (m, 1H), 4.30-4.21 (m, 3H), 4.13 (d, J 13.3 Hz, 1H), 4.00 (d, J 13.1 Hz, 1H), 3.29-3.15 (m, 2H), 3.12-2.98 (m, 1H), 2.27 (s, 3H), 2.10 (s, 3H), 1.30 (t, J 7.0 Hz, 3H), 1.18 (d, J 6.6 Hz, 3H). LCMS (ES+) [M+H]$^+$ 410, RT 2.52 minutes (method 1).

Example 18

(3S)—N-(6-Methoxy-2-methylpyridin-3-yl)-3-methyl-4-(2-methylpyrazolo[1,5-a]-pyrimidin-7-yl)piperazine-1-carboxamide Intermediate 35 (0.075 g, 0.32 mmol) was dissolved in acetonitrile (3.91 g) and Intermediate 39 (0.092 g, 0.36 mmol) was added, followed by DIPEA (0.13 g, 0.97 mmol). The reaction mixture was stirred at 70° C. for 1 h, then concentrated. The residue was purified by preparative HPLC. The resulting colourless solution was freeze-dried to give the title compound (0.080 g, 62%) as a white solid. $\delta_H$ (DMSO-d$_6$, 400 MHz) 8.22 (d, J 5.1 Hz, 1H), 8.17 (s, 1H), 7.45 (d, J 8.5 Hz, 1H), 6.62 (d, J 8.5 Hz, 1H), 6.36 (s, 1H), 6.33 (d, J 5.1 Hz, 1H), 5.22-5.17 (m, 1H), 4.24-4.16 (m, 1H), 4.01 (d, J 13.3 Hz, 1H), 3.89-3.84 (m, 4H), 3.53-3.38 (m, 2H), 3.21-3.13 (m, 1H), 2.42 (s, 3H), 2.30 (s, 3H), 1.15 (d, J 6.7 Hz, 3H). LCMS MH$^+$ 396, RT 1.53 minutes (method 4).

Example 19

(3S)—N-[4-(Difluoromethoxy)-2-methylphenyl]-3-methyl-4-(2-methylpyrazolo[1,5-a]-pyrimidin-7-yl)piperazine-1-carboxamide Intermediate 35 (0.075 g, 0.32 mmol) was dissolved in acetonitrile (3.91 g) and Intermediate 44 (0.10 g, 0.36 mmol) was added, followed by DIPEA (0.13 g, 0.97 mmol). The reaction mixture was stirred at 70° C. for 1 h. The resulting solution was concentrated and the residue was purified by preparative HPLC. The resulting colourless solution was freeze-dried to give the title compound (0.070 g, 50%) as a white solid. $\delta_H$ (DMSO-d$_6$, 400 MHz) 8.21 (d, J 5.1 Hz, 1H), 8.17 (s, 1H), 6.95-7.37 (m, 4H), 6.36 (s, 1H), 6.32 (d, J 5.1 Hz, 1H), 5.17-5.26 (m, 1H), 4.17-4.25 (m, 1H), 3.98-4.06 (m, 1H), 3.83-3.92 (m, 1H), 3.45-3.55 (m, 1H), 3.37-3.45 (m, 1H), 3.14-3.25 (m, 1H), 2.43 (s, 3H), 2.20 (s, 3H), 1.15 (d, J 6.7 Hz, 3H). LCMS MH$^+$ 431, RT 1.48 minutes (method 4).

Example 20

(3S)-4-(5-Amino-2-methylpyrazolo[1,5-a]pyrimidin-7-yl)-N-(4-methoxy-2-methyl-phenyl)-3-methylpiperazine-1-carboxamide To a solution of Intermediate 34 (0.35 mmol) in DMF (6 mL) was added 4-methoxy-2-methylphenyl isocyanate (62 μL, 0.45 mmol) and the reaction mixture was stirred for 13 h. The volatiles were evaporated and the residue was purified by silica gel chromatography, eluting with DCM:MeOH (20:1, then 10:1), to provide the title compound (125 mg, 88%). $^{13}$C NMR δ (CDCl$_3$, 75 MHz) 157.4 (2C), 157.1, 153.3, 150.4 (2C), 135.1, 129.9, 127.6, 115.8, 111.7, 91.3, 82.3, 55.4, 49.8, 48.4, 43.3, 42.6, 18.1, 14.7, 13.1. MS (m/z) 410 [M+H]$^+$.

Example 21

(3S)-4-(2-Amino-8-chloropyrazolo[1,5-a][1,3,5]triazin-4-yl)-N-(2,6-dimethoxypyridin-3-yl)-3-ethyl-piperazine-1-carboxamide To Intermediate 53 (0.3 g, 1.057 mmol) in ethanol (10 mL) maintained at 0° C. was added DIPEA (0.545 mL, 3.17 mmol). The mixture was stirred for 5 minutes, followed by the addition of Intermediate 45 (0.347 g, 1.26 mmol). The reaction mixture was heated at 80° C. for 2 h, then evaporated in vacuo. The residue was diluted in EtOAc (50 mL). The organic layer was washed with water (25 mL), then dried over anhydrous sodium sulfate and concentrated in vacuo. The crude material obtained was purified by column chromatography (normal phase; silica 100-200 mesh; 2% MeOH in DCM) to afford the title compound (145 mg, 30%). $\delta_H$ (DMSO-d$_6$, 400 MHz) 7.97 (s, 1H), 7.81 (s, 1H), 7.60 (d, J 8.4 Hz, 1H), 6.84 (s, 2H), 6.33 (d, J 8.3 Hz, 1H), 5.46 (s, 2H), 4.14-4.05 (m, 2H), 3.87 (s, 3H), 3.83 (s, 3H), 3.38 (d, J 12.4 Hz, 1H), 3.33-3.17 (m, 1H), 3.14-3.02 (m, 1H), 1.84-1.74 (m, 2H), 0.90 (t, J 7.0 Hz, 3H). LCMS (ES+) [M+H]$^+$ 462.3, RT 2.70 minutes (method 4).

Example 22

(3S)-4-(2-Amino-8-chloro pyrazolo[1,5-a][1,3,5]triazin-4-yl)-3-ethyl-N-(4-methoxy-3-methylphenyl)piperazine-1-carboxamide To a solution of Intermediate 53 (0.5 g, 1.76 mmol) in ethanol (20 mL) was added DIPEA (0.911 mL, 5.3 mmol). The mixture was stirred for 5 minutes, followed by the addition of Intermediate 48 (0.545 g, 2.12 mmol). The reaction mixture was heated at 80° C. for 4 h, then evaporated in vacuo. The crude residue was dissolved in EtOAc (50 mL). The organic layer was washed with water (25 mL), then dried over anhydrous sodium sulfate and concentrated in vacuo. The crude residue was purified by column chromatography (normal phase; silica 100-200 mesh; 2% MeOH in DCM) to afford the title compound (220 mg, 28%). $\delta_H$ (DMSO-d$_6$, 400 MHz) 8.32 (s, 1H), 7.96 (s, 1H), 7.21-7.19 (m, 2H), 6.84 (s, 2H), 6.81 (d, J 9.2 Hz, 1H), 5.60-5.40 (m, 2H), 4.11 (t, J 12.2 Hz, 2H), 3.73 (s, 3H), 3.44-3.30 (m, 1H), 3.21-3.04 (m, 2H), 2.11 (s, 3H), 1.77-1.66 (m, 2H), 0.84 (t, J 7.1 Hz, 3H). LCMS (ES+) [M+H]$^+$ 445.0, RT 2.22 minutes (method 4).

Example 23

(3S)-4-(2-Amino-8-chloropyrazolo[1,5-a][1,3,5]triazin-4-yl)-N-[2-chloro-4-(trifluoro-methoxy)phenyl]-3-ethylpiperazine-1-carboxamide To a solution of Intermediate 53 (0.3 g, 1.057 mmol) in ethanol (10 mL) maintained at 0° C. was added DIPEA (0.545 mL, 3.17 mmol). The mixture was stirred for 5 minutes, followed by the addition of Intermediate 49 (0.42 g, 1.26 mmol). The reaction mixture was heated at 80° C. for 2 h, then evaporated in vacuo. The residue was dissolved in EtOAc (50 mL). The organic layer was washed with water (20 mL) and separated, then dried over anhydrous sodium sulfate and concentrated in vacuo. The resulting crude material was purified by preparative HPLC to afford the title compound (70 mg, 13%). δ$_H$ (DMSO-d$_6$, 400 MHz) 8.41 (s, 1H), 7.97 (s, 1H), 7.62-7.54 (m, 2H), 7.40-7.32 (m, 1H), 6.86 (s, 2H), 5.60-5.40 (m, 2H), 4.11 (t, J 12.2 Hz, 2H), 3.41-3.11 (m, 3H), 1.84-1.70 (m, 2H), 0.84 (t, J 7.1 Hz, 3H). LCMS (ES+) [M+H]$^+$ 519.0, RT 2.66 minutes (method 4).

Example 24

(3S)-4-(2-Amino-8-chloropyrazolo[1,5-a][1,3,5]triazin-4-yl)-3-ethyl-N-[2-methyl-4-(trifluoromethoxy)phenyl]piperazine-1-carboxamide To a solution of Intermediate 53 (0.6 g, 2.11 mmol) in ethanol (10 mL) maintained at 0° C. was added DIPEA (1.09 mL, 6.34 mmol). The mixture was stirred for 5 minutes, followed by the addition of Intermediate 41 (0.789 g, 2.53 mmol). The reaction mixture was heated at 80° C. for 2 h, then evaporated in vacuo. The residue was dissolved in EtOAc (50 mL), washed with water (30 mL) and separated, then dried over anhydrous sodium sulfate and concentrated in vacuo. The crude residue was purified by preparative HPLC to afford the title compound (220 mg, 21%). δ$_H$ (DMSO-d$_6$, 400 MHz) 8.20 (s, 1H), 7.97 (s, 1H), 7.28 (d, J 8.7 Hz, 1H), 7.21 (s, 1H), 7.18-7.10 (m, 1H), 6.85 (s, 2H), 5.43-5.20 (m, 2H), 4.12 (t, J 12.2 Hz, 2H), 3.40-3.07 (m, 3H), 2.20 (s, 3H), 1.85-1.66 (m, 2H), 0.86 (t, J 7.4 Hz, 3H). LCMS (ES+) [M+H]$^+$ 499.2, RT 3.01 minutes (method 4).

Example 25

(3S)-4-(2-Amino-8-methylpyrazolo[1,5-a][1,3,5]triazin-4-yl)-N-(2,6-dimethoxypyridin-3-yl)-3-ethylpiperazine-1-carboxamide To a stirred solution of Intermediate 57 (0.6 g, 2.29 mmol) in acetonitrile (15 mL) was added DIPEA (1.38 mL, 8.04 mmol). The mixture was stirred for 20 minutes, then Intermediate 45 (0.63 g, 2.29 mmol) was added. The resulting mixture was stirred at r.t. for 16 h, then diluted with EtOAc (50 mL). The organic layer was washed with water (25 mL) and separated, then dried over anhydrous sodium sulfate and concentrated in vacuo. The crude residue was purified by preparative HPLC to afford the title compound (220 mg, 21%). δ$_H$ (DMSO-d$_6$, 400 MHz) 7.81 (s, 1H), 7.70 (s, 1H), 7.60 (d, J 8.3 Hz, 1H), 6.46 (s, 2H), 6.34 (dd, J 8.2, 1.8 Hz, 1H), 5.53-5.20 (m, 1H), 4.14-4.04 (m, 2H), 3.84 (s, 3H), 3.86 (s, 3H), 3.24-3.14 (m, 3H), 3.10-2.99 (m, 1H), 1.98 (s, 3H), 1.81-1.63 (m, J 7.1 Hz, 2H), 0.83 (t, J 7.5 Hz, 3H). LCMS (ES+) [M+H]$^+$ 442.0, RT 1.96 minutes (method 4).

Example 26

(3S)-4-(2-Amino-8-methylpyrazolo[1,5-a][1,3,5]triazin-4-yl)-3-ethyl-N-(4-methoxy-3-methylphenyl)piperazine-1-carboxamide To a solution of Intermediate 57 (0.8 g, 1.7 mmol) in acetonitrile (10 mL) was added DIPEA (1 mL). The mixture was stirred for 20 minutes, then Intermediate 48 (0.5 g, 1.9 mmol) was added. The reaction mixture was stirred at r.t. for 3 h, then diluted with EtOAc (80 mL). The organic layer was washed with water (30 mL) and separated, then dried over anhydrous sodium sulfate and concentrated in vacuo. The crude residue was purified by preparative HPLC to afford the title compound (100 mg, 13%). δ$_H$ (DMSO-d$_6$, 400 MHz) 8.32 (s, 1H), 7.70 (s, 1H), 7.21 (d, J 7.1 Hz, 2H), 6.85-6.78 (m, 1H), 6.46 (s, 2H), 4.17-4.04 (m, 2H), 3.74 (s, 3H), 3.17 (d, J 5.2 Hz, 4H), 3.04 (m, 1H), 2.11 (s, 3H), 1.99 (s, 3H), 1.80-1.61 (m, 2H), 0.82 (t, J 7.4 Hz, 3H). LCMS (ES+) [M+H]$^+$ 425.0, RT 2.07 minutes (method 4).

Example 27

(3S)-4-(2-Amino-8-methylpyrazolo[1,5-a][1,3,5]triazin-4-yl)-N-[2-chloro-4-(trifluoro-methoxy)phenyl]-3-ethylpiperazine-1-carboxamide To a solution of Intermediate 57 (0.75 g, 1.6 mmol) in acetonitrile (10 mL) was added DIPEA (1 mL). The mixture was stirred for 20 minutes, then Intermediate 49 (0.602 g, 1.8 mmol) was added. The reaction mixture was stirred at r.t. for 3 h, then diluted with EtOAc (50 mL). The organic layer was washed with water (30 mL) and separated, then dried over anhydrous sodium sulfate and concentrated in vacuo. The crude residue was purified by preparative HPLC to afford the title compound (115 mg, 14%). δ$_H$ (DMSO-d$_6$, 400 MHz) 8.40 (s, 1H), 7.70 (s, 1H), 7.62-7.54 (m, 2H), 7.39-7.30 (m, 1H), 6.44 (s, 2H), 5.57-5.40 (m, 2H), 4.12 (t, J 13.4 Hz, 2H), 3.41-3.33 (m, 1H), 3.32-3.22 (m, 1H), 3.13 (td, J 12.7, 3.4 Hz, 1H), 1.99 (s, 3H), 1.83-1.65 (m, J 6.9 Hz, 2H), 0.84 (t, J 7.4 Hz, 3H). LCMS (ES+) [M+H]$^+$ 499.0, RT 2.76 minutes (method 4).

Example 28

(3S)-4-(2-Amino-8-methylpyrazolo[1,5-a][1,3,5]triazin-4-yl)-3-ethyl-N-[2-methyl-4-(trifluoromethoxy)phenyl]piperazine-1-carboxamide To a solution of Intermediate 57 (0.85 g, 1.8 mmol) in acetonitrile (10 mL) was added DIPEA (1.1 mL, 6.5 mmol). The mixture was stirred for 20 minutes, then Intermediate 41 (0.64 g, 2 mmol) was added. The reaction mixture was stirred at r.t. for 3 h, then diluted with EtOAc (50 mL). The organic layer was washed with water (30 mL) and separated, then dried over anhydrous sodium sulfate and concentrated in vacuo. The crude residue was purified by preparative HPLC to afford the title compound (170 mg, 19%). δ$_H$ (CD$_3$OD, 400 MHz) 7.65 (s, 1H), 7.24 (d, J 8.6 Hz, 1H), 7.15 (d, J 2.9 Hz, 1H), 7.12-7.04 (m, 1H), 5.68-5.48 (m, 2H), 4.21-4.10 (m, 2H), 3.49 (d, J 14.0 Hz, 1H), 3.38 (dd, J 13.7, 3.8 Hz, 1H), 3.31-3.19 (m, 1H), 2.27 (s, 3H), 2.07 (s, 3H), 1.92 (m, 1H), 1.80 (m, 1H), 0.95 (t, J 7.5 Hz, 3H). LCMS (ES+) [M+H]+ 479.0, RT 2.38 minutes (method 4).

Example 29

(3S)-4-(2-Amino-8-methylpyrazolo[1,5-a][1,3,5]triazin-4-yl)-3-ethyl-N-(4-methoxy-2-methylphenyl)piperazine-1-carboxamide To a solution of Intermediate 57 (1 g, 2.2 mmol) in acetonitrile (15 mL) was added DIPEA (1.3 mL, 7.7 mmol). The mixture was stirred for 30 minutes, then Intermediate 38 (0.624 g, 2.4 mmol) was added. The reaction mixture was stirred at r.t. for 3 h, then diluted with EtOAc (50 mL). The organic layer was washed with water (30 mL) and separated, then dried over anhydrous sodium sulfate and concentrated in vacuo. The crude residue was purified by preparative HPLC to afford the title compound (180 mg, 19%). $\delta_H$ (DMSO-$d_6$, 400 MHz) 7.99 (s, 1H), 7.70 (s, 1H), 7.02 (d, J 8.6 Hz, 1H), 6.78 (d, J 2.9 Hz, 1H), 6.70 (dd, J 8.6, 3.0 Hz, 1H), 6.46 (s, 2H), 5.60-5.20 (m, 2H), 4.12 (t, J 13.8 Hz, 2H), 3.72 (s, 3H), 3.20 (dd, J 13.6, 3.7 Hz, 2H), 3.04 (m, 1H), 2.14 (s, 3H), 1.99 (s, 3H), 1.82-1.65 (m, J 7.1 Hz, 2H), 0.84 (t, J 7.4 Hz, 3H). LCMS (ES+) [M+H]+ 425.0, RT 1.98 minutes (method 4).

Example 30

(3S)-4-(2-Amino-8-methylpyrazolo[1,5-a][1,3,5]triazin-4-yl)-N-(2,6-dimethoxypyridin-3-yl)-3-methylpiperazine-1-carboxamide To Intermediate 37 (102.6 mg, 0.32 mmol) were added Intermediate 45 (113.5 mg, 0.41 mmol) and acetonitrile (5 mL) prior to the addition of DIPEA (0.23 mL, 1.3 mmol). The reaction mixture was stirred at r.t. for approximately 42 h, then partitioned between water (30 mL) and DCM (30 mL). The organic layer was separated and washed with water (30 mL). The organic layer was separated, dried with anhydrous sodium sulfate and filtered under reduced pressure. The solvent was removed in vacuo. The resulting purple oil was purified by preparative HPLC to afford the title compound (24.2 mg, 16.3%) as a pale pink solid. $\delta_H$ (DMSO-$d_6$, 500 MHz) 7.80 (s, 1H), 7.70 (s, 1H), 7.62 (d, J 8.2 Hz, 1H), 6.47 (s, 2H), 6.34 (d, J 8.2 Hz, 1H), 4.08 (d, J 11.3 Hz, 1H), 3.94 (d, J 12.7 Hz, 1H), 3.88 (s, 3H), 3.84 (s, 3H), 3.50-3.39 (m, 4H), 3.16-3.03 (m, 1H), 1.99 (s, 3H), 1.28 (d, J 6.7 Hz, 3H). LCMS (ES+) [M+H]+ 428.3, RT 1.91 minutes (method 1).

Example 31

(3S)-4-(2-Amino-8-methylpyrazolo[1,5-a][1,3,5]triazin-4-yl)-N-(4-methoxy-3-methyl-phenyl)-3-methylpiperazine-1-carboxamide To Intermediate 37 (142.3 mg, 0.44 mmol) were added Intermediate 48 (154.3 mg, 0.60 mmol), acetonitrile (7.5 mL) and DIPEA (0.31 mL, 1.8 mmol). The dark purple mixture was stirred for 18 h at r.t., then filtered under reduced pressure and washed with acetonitrile. The dark brown acetonitrile layer was concentrated in vacuo and purified by basic preparative HPLC to afford the title compound (20.3 mg, 11.1%) as a white solid. $\delta_H$ (DMSO-$d_6$, 500 MHz) 8.31 (s, 1H), 7.70 (s, 1H), 7.25-7.18 (m, 2H), 6.82 (d, J 8.4 Hz, 1H), 6.47 (s, 2H), 5.56 (br s, 1H), 5.10 (br s, 1H), 4.11 (d, J 12.9 Hz, 1H), 3.97 (d, J 13.2 Hz, 1H), 3.74 (s, 3H), 3.50-3.40 (m, 1H), 3.27 (dd, J 13.5, 3.8 Hz, 1H), 3.08 (td, J 12.6, 3.4 Hz, 1H), 2.12 (s, 3H), 1.99 (s, 3H), 1.27 (d, J 6.7 Hz, 3H). LCMS (ES+) [M+H]+ 411.3, RT 1.98 minutes (method 1).

Example 32

(3S)-4-(2-Amino-8-methylpyrazolo[1,5-a][1,3,5]triazin-4-yl)-N-[2-chloro-4-(trifluoro-methoxy)phenyl]-3-methylpiperazine-1-carboxamide To a suspension of Intermediate 37 (40 mg, 0.125 mmol) in acetonitrile (1 mL) at r.t. were introduced DIPEA (48 mg, 0.375 mmol) and a solution of Intermediate 49 (41 mg) in acetonitrile (1 mL). After 3 days at r.t., the reaction mixture was warmed to 60° C. for 24 h, then concentrated in vacuo. The residue was re-dissolved in EtOAc (20 mL). After washing with saturated aqueous sodium bicarbonate solution (2×5 mL), the organic phase was dried with anhydrous sodium sulfate, then filtered. The filtrate was concentrated in vacuo. The residue was purified by reverse-phase preparative liquid chromatography (acetonitrile/water/ammonia) to afford the title compound (14.2 mg, 23%) as a colourless oil. $\delta_H$ (CD$_3$OD, 500 MHz) 7.65 (s, 1H), 7.62 (d, J 8.9 Hz, 1H), 7.42 (d, J 2.2 Hz, 1H), 7.25 (dd, J 8.9, 1.8 Hz, 1H), 5.67 (s, 1H), 5.29 (s, 1H), 4.16 (d, J 13.4 Hz, 1H), 3.99 (dt, J 13.6, 2.3 Hz, 1H), 3.62 (td, J 14.2, 13.1, 3.5 Hz, 1H), 3.49 (dd, J 13.7, 3.9 Hz, 1H), 3.35 (dd, J 12.6, 3.5 Hz, 1H), 2.07 (s, 3H), 1.41 (d, J 6.7 Hz, 3H). LCMS (ES+) 485/487 [M+H]+, RT 2.61 minutes (method 1).

Example 33

(3S)-4-(2-Aminopyrazolo[1,5-a][1,3,5]triazin-4-yl)-N-(2,6-dimethoxypyridin-3-yl)-3-ethylpiperazine-1-carboxamide Prepared using Intermediate 60 (200 mg, 0.81 mmol) and Intermediate 45 (222 mg, 0.81 mmol), by applying the procedure described for Example 18, to afford the title compound (203 mg, 59%) as a slightly pink powder. $\delta_H$ (DMSO-$d_6$, 400 MHz) 7.83 (d, J 2.1 Hz, 1H), 7.81 (s, 1H), 7.62 (d, J 8.2 Hz, 1H), 6.49 (s, 2H), 6.34 (d, J 8.2 Hz, 1H), 5.76 (d, J 2.1 Hz, 1H), 5.53 (br s, 1H), 5.05 (br s, 1H), 4.07-4.13 (m, 2H), 3.88 (s, 3H), 3.85 (s, 3H), 3.28-3.39 (m, 1H), 3.22 (dd, J 13.7, 3.6 Hz, 1H), 3.04-3.11 (m, 1H), 1.66-1.83 (m, 2H), 0.86 (t, J 7.5 Hz, 3H). LCMS (ES+) [M+H]+ 428, RT 1.81 minutes (method 4).

Example 34

(3S)-4-(2-Aminopyrazolo[1,5-a][1,3,5]triazin-4-yl)-3-ethyl-N-(4-methoxy-3-methyl-phenyl)piperazine-1-carboxamide Prepared using Intermediate 60 (200 mg, 0.81 mmol) and Intermediate 48 (208 mg, 0.81 mmol), by applying the procedure described for Example 18, to afford the title compound (189 mg, 57%) as a white powder. $\delta_H$ (DMSO-$d_6$, 400 MHz) 8.32 (s, 1H), 7.83 (d, J 2.1 Hz, 1H), 7.20-7.24 (m, 1H), 7.21 (s, 1H), 6.81-6.84 (m, 1H), 6.49 (s, 2H), 5.76 (d, J 2.1 Hz, 1H), 5.54 (br s, 1H), 5.07 (br s, 1H), 4.11-4.15 (m, 2H), 3.74 (s, 3H), 3.31-3.39 (m, 1H), 3.20 (dd, J 13.7, 3.7 Hz, 1H), 3.03-3.10 (m, 1H), 2.12 (s, 3H), 1.63-1.81 (m, 2H), 0.84 (t, J 7.3 Hz, 3H). LCMS (ES+) [M+H]+ 411, RT 1.87 minutes (method 4).

Example 35

(3S)-4-(2-Aminopyrazolo[1,5-a][1,3,5]triazin-4-yl)-3-ethyl-N-[2-methyl-4-(trifluoro-methoxy)phenyl]piperazine-1-carboxamide Prepared using Intermediate 60 (200 mg, 0.81 mmol) and Intermediate 41 (252 mg, 0.81 mmol), by applying the procedure described for Example 18, to afford the title compound (216 mg, 57%) as a white powder. $\delta_H$ (DMSO-$d_6$, 400 MHz) 8.21 (s, 1H), 7.84 (d, J 2.1 Hz, 1H), 7.29 (m, 1H), 7.21-7.22 (m, 1H), 7.13-7.16 (m, 1H), 6.49 (s, 2H), 5.77 (d, J 2.1 Hz, 1H), 5.53 (br s, 1H), 5.06 (br s, 1H), 4.09-4.17 (m, 2H), 3.31-3.42 (m, 1H), 3.26 (dd, J 13.8, 3.8 Hz, 1H), 3.09-3.18 (m, 1H), 2.22 (s, 3H), 1.67-1.85 (m, 2H), 0.87 (m, 3H). LCMS (ES+) [M+H]$^+$ 465, RT 2.24 minutes (method 4).

Example 36

(3S)-4-(2-Aminopyrazolo[1,5-a][1,3,5]triazin-4-yl)-3-ethyl-N-(4-methoxy-2-methyl-phenyl)piperazine-1-carboxamide Prepared using Intermediate 60 (200 mg, 0.81 mmol) and Intermediate 38 (208 mg, 0.81 mmol), by applying the procedure described for Example 18, to afford the title compound (110 mg, 33%) as a white powder. $\delta_H$ (DMSO-$d_6$, 400 MHz) 7.99 (s, 1H), 7.82 (d, J 2.1 Hz, 1H), 7.02 (d, J 8.6 Hz, 1H), 6.78 (d, J 2.8 Hz, 1H), 6.70 (dd, J 8.6, 2.9 Hz, 1H), 6.48 (s, 2H), 5.75 (d, J 2.1 Hz, 1H), 5.53 (br s, 1H), 5.08 (br s, 1H), 4.08-4.16 (m, 2H), 3.72 (s, 3H), 3.33 (br s, 1H), 3.21 (dd, J 13.7, 3.7 Hz, 1H), 3.02-3.10 (m, 1H), 2.14 (s, 3H), 1.69-1.82 (m, 2H), 0.86 (t, J 7.4 Hz, 3H). LCMS (ES+) [M+H]$^+$ 411, RT 1.72 minutes (method 4).

Example 37

(3S)-4-(2-Aminopyrazolo[1,5-a][1,3,5]triazin-4-yl)-3-ethyl-N-[5-methoxy-6-(trifluoro-methyl)pyridin-2-yl]piperazine-1-carboxamide Prepared using Intermediate 60 (184 mg, 0.58 mmol) and Intermediate 46 (180 mg, 0.58 mmol), by applying the procedure described for Example 18, to afford the title compound (60 mg, 22%) as a white powder. $\delta_H$ (DMSO-$d_6$, 400 MHz) 9.33 (s, 1H), 7.97 (m, 1H), 7.83 (d, J 2.1 Hz, 1H), 7.80 (m, 1H), 6.49 (s, 2H), 5.76 (d, J 2.1 Hz, 1H), 5.56 (br s, 1H), 5.10 (br s, 1H), 4.16-4.23 (m, 2H), 3.89 (s, 3H), 3.31-3.44 (m, 1H), 3.20 (dd, J 13.7, 3.6 Hz, 1H), 3.05-3.15 (m, 1H), 1.60-1.83 (m, 2H), 0.82 (t, J 7.3 Hz, 3H). LCMS (ES+) [M+H]$^+$ 464, RT 2.09 minutes (method 4).

Example 38

(3S)-4-(2-Aminopyrazolo[1,5-a][1,3,5]triazin-4-yl)-N-[6-(azetidin-1-yl)-2-methylpyridin-3-yl]-3-ethyl-piperazine-1-carboxamide Prepared using Intermediate 60 (230 mg, 0.72 mmol) and Intermediate 47 (204 mg, 0.72 mmol), by applying the procedure described for Example 18, except that the product was purified by silica gel chromatography (gradient of 0-10% MeOH in EtOAc), to afford the title compound (255 mg, 81%) as a white solid. $\delta_H$ (DMSO-$d_6$, 400 MHz) 7.98 (s, 1H), 7.82 (d, J 2.1 Hz, 1H), 7.21 (d, J 8.5 Hz, 1H), 6.48 (s, 2H), 6.16 (d, J 8.5 Hz, 1H), 5.75 (d, J 2.1 Hz, 1H), 5.53 (br s, 1H), 5.05 (br s, 1H), 4.07-4.15 (m, 2H), 3.88 (t, J 7.3 Hz, 4H), 3.28-3.37 (m, 1H), 3.21 (dd, J 13.6, 3.6 Hz, 1H), 3.02-3.10 (m, 1H), 2.24-2.32 (m, 2H), 2.19 (s, 3H), 1.67-1.81 (m, 2H), 0.86 (t, J 7.3 Hz, 3H). LCMS (ES+) [M+H]$^+$ 437, RT 1.42 minutes (method 4).

Example 39

(3S)-4-(2-Amino-8-methylpyrazolo[1,5-a][1,3,5]triazin-4-yl)-N-[5-methoxy-6-(trifluoro-methyl)pyridin-2-yl]-3-methylpiperazine-1-carboxamide Prepared using Intermediate 37 (184 mg, 0.58 mmol) and Intermediate 46 (180 mg, 0.58 mmol), by applying the procedure described for Example 18, to afford the title compound (200 mg, 74%) as a white solid. $\delta_H$ (DMSO-$d_6$, 400 MHz) 9.31 (s, 1H), 7.98 (m, 1H), 7.80 (d, J 9.3 Hz, 1H), 7.70 (s, 1H), 6.47 (s, 2H), 5.57 (br s, 1H), 5.08 (br s, 1H), 4.15-4.19 (m, 1H), 4.03-4.07 (m, 1H), 3.89 (s, 3H), 3.42-3.50 (m, 1H), 3.26 (dd, J 13.9, 4.0 Hz, 1H), 3.07-3.16 (m, 1H), 1.98 (s, 3H), 1.26 (d, J 6.7 Hz, 3H). LCMS (ES-) [M-H]$^-$ 464, RT 1.98 minutes (method 4).

Example 40

(3S)-4-(2-Amino-8-methylpyrazolo[1,5-a][1,3,5]triazin-4-yl)-N-[6-(azetidin-1-yl)-2-methylpyridin-3-yl]-3-methylpiperazine-1-carboxamide Prepared using Intermediate 37 (277 mg, 0.86 mmol) and Intermediate 47 (246 mg, 0.86 mmol), by applying the procedure described for Example 38, to afford the title compound (274 mg, 73%) as a white solid. $\delta_H$ (DMSO-$d_6$, 400 MHz) 7.97 (s, 1H), 7.70 (s, 1H), 7.22 (d, J 8.5 Hz, 1H), 6.46 (s, 2H), 6.15 (d, J 8.5 Hz, 1H), 5.56 (br s, 1H), 5.07 (br s, 1H), 4.07-4.13 (m, 1H), 3.92-3.98 (m, 1H), 3.85-3.91 (m, 4H), 3.36-3.47 (m, 1H), 3.24-3.33 (m, 1H), 3.02-3.13 (m, 1H), 2.23-2.33 (m, 2H), 2.19 (s, 3H), 1.98 (s, 3H), 1.28 (d, J 6.7 Hz, 3H). LCMS (ES-) [M-H]$^-$ 435, RT 1.53 minutes (method 4).

Example 41

(3S)-4-(2-Amino-8-methylpyrazolo[1,5-a][1,3,5]triazin-4-yl)-3-ethyl-N-[5-methoxy-6-(trifluoromethyl)pyridin-2-yl]piperazine-1-carboxamide Intermediate 57 (570 mg, 1.7 mmol) and Intermediate 46 (533 mg, 1.7 mmol) were stirred in acetonitrile (30 mL) with DIPEA (0.89 mL, 5.1 mmol) at r.t. for 24 h. The reaction mixture was concentrated in vacuo, and the residue was purified by column chromatography (Isolera, 100 g Si column, eluting with a gradient of 100% EtOAc to 20% MeOH in EtOAc), to furnish the title compound (400 mg, 48.9%) as a white solid. $\delta_H$ (DMSO-$d_6$, 400 MHz) 9.32 (s, 1H), 7.97 (d, J 9.1 Hz, 1H), 7.79 (d, J 9.3 Hz, 1H), 7.70 (s, 1H), 6.45 (s, 2H), 5.41-5.71 (m, 1H), 4.80-5.15 (m, 1H), 4.16-4.20 (m, 2H), 3.89 (s, 3H), 3.31-3.39 (m, 1H), 3.05-3.25 (m, 2H), 1.99 (s, 3H), 1.55-1.79 (m, 2H), 0.75-0.81 (m, 3H). LCMS (ES+) [M+H]$^+$ 480, RT 2.23 minutes (method 4).

Example 42

(3S)-4-(2-Amino-8-methylpyrazolo[1,5-a][1,3,5]triazin-4-yl)-N-[6-(azetidin-1-yl)-2-methylpyridin-3-yl]-3-ethylpiperazine-1-carboxamide Intermediate 57 (236 mg, 0.7 mmol) and Intermediate 47 (200 mg, 0.7 mmol) were stirred in acetonitrile (30 mL) with DIPEA (0.89 mL, 5.1 mmol) at r.t. for 24 h. The reaction mixture was concentrated in vacuo and the residue was phase-separated between DCM and water. The DCM layer was concentrated in vacuo, and the residue was purified by column chromatography (Isolera, 25 g Si column, eluting with a gradient of 100% EtOAc to 25% MeOH in EtOAc), to furnish the title compound (176 mg, 55.3%) as a white solid. $\delta_H$ (DMSO-$d_6$, 400 MHz) 7.97 (s, 1H), 7.70 (s, 1H), 7.25 (d, J 8.5 Hz, 1H), 6.45 (s, 2H), 6.16 (d, J 8.5 Hz, 1H), 5.40-5.65 (m, 1H), 4.91-5.15 (m, 1H), 4.05-4.19 (m, 2H), 3.88 (t, J 7.3 Hz, 4H), 3.25-3.35 (m, 1H), 3.18-3.25 (m, 1H), 3.02-3.11 (m, 1H), 2.25-2.31 (m, 2H), 2.19 (m, 3H), 1.99 (m, 3H), 1.65-1.81 (m, 2H), 0.81-0.89 (m, 3H). LCMS (ES+) [M+H]⁺ 451, RT 1.56 minutes (method 4).

The invention claimed is:

1. A compound of formula (I), or a pharmaceutically acceptable salt or solvate thereof:

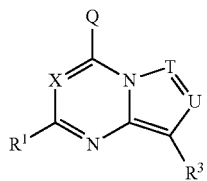

(I)

wherein
X represents N;
T and U independently represent N or C—$R^2$;
Q represents a group of formula (Qa), (Qb), (Qc), (Qd) or (Qe):

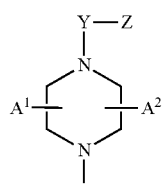

(Qa)

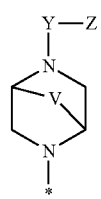

(Qb)

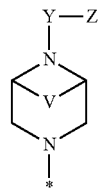

(Qc)

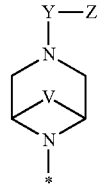

(Qd)

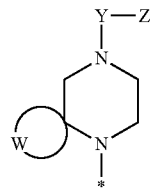

(Qe)

in which the asterisk (*) represents the point of attachment to the remainder of the molecule;
V represents —$CH_2$—, —$C(CH_3)_2$—, —$CH_2CH_2$— or —$CH_2CH_2CH_2$—;
W represents the residue of a $C_{3-7}$ cycloalkyl group;
Y represents —C(O)—, —C(O)N($R^4$)—, or —C(O)C(O)—;
Z represents aryl or heteroaryl, either of which groups may be optionally substituted by one or more substituents;
$A^1$ represents hydrogen, cyano or trifluoromethyl; or $A^1$ represents $C_{1-6}$ alkyl, optionally substituted by one or more substituents independently selected from fluoro, —$OR^a$, trifluoromethoxy, —$NR^bR^c$, —$CO_2R^d$ and —$CONR^bR^c$; or $A^1$ represents $C_{3-7}$ cycloalkyl;
$A^2$ represents hydrogen or $C_{1-6}$ alkyl;
$R^1$ represents —$NR^bR^c$;
$R^2$ represents hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one or more substituents;
$R^3$ represents hydrogen, halogen or $C_{1-6}$ alkyl;
$R^4$ represents hydrogen; or $R^4$ represents $C_{1-6}$ alkyl, optionally substituted by one or more substituents independently selected from —$OR^a$ and —$NR^bR^c$;
$R^a$ represents hydrogen; or $R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents;
$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or
$R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;
$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

2. The compound as claimed in claim 1 wherein T represents N and U represents C—$R^2$.

3. The compound as claimed in claim 1 wherein Q represents a group of formula (Qa-1), (Qa-2) or (Qa-3):

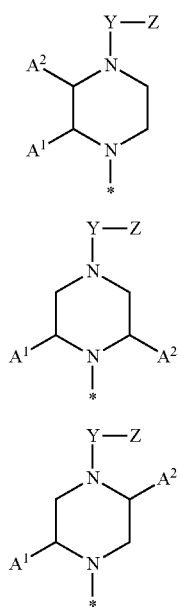

(Qa-1)

(Qa-2)

(Qa-3)

in which the asterisk (*) represents the point of attachment to the remainder of the molecule.

4. The compound as claimed in claim 1 represented by formula (IIA), or a pharmaceutically acceptable salt or solvate thereof:

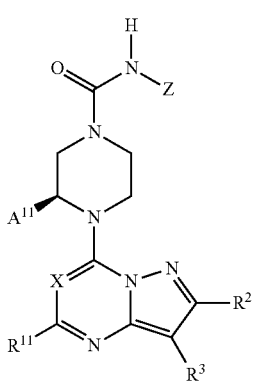

(IIA)

wherein $A^{11}$ represents hydrogen, cyano, $C_{1-6}$ alkyl, —$CH_2OR^a$, —$CH_2CH_2OR^a$, —$CH_2CO_2R^d$, —$CH_2CONR^bR^c$ or $C_{3-7}$ cycloalkyl; and $R^{11}$ represents amino.

5. The compound as claimed in claim 1 represented by formula (IIB), or a pharmaceutically acceptable salt or solvate thereof:

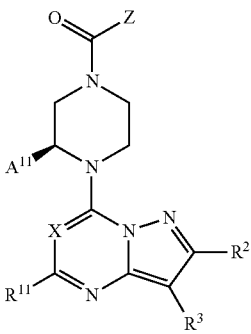

(IIB)

wherein $A^{11}$ represents hydrogen, cyano, $C_{1-6}$ alkyl, —$CH_2OR^a$, —$CH_2CH_2OR^a$, —$CH_2CO_2R^d$, —$CH_2CONR^b$Ie or $C_{3-7}$ cycloalkyl; and $R^{11}$ represents amino.

6. The compound as claimed in claim 4 wherein $A^{11}$ represents methyl or ethyl.

7. The compound as claimed in claim 1 wherein Z represents aryl or heteroaryl, either of which groups is optionally substituted by one, two or three substituents independently selected from halogen, $C_{1-6}$ alkyl, trifluoromethyl, $(C_{3-7})$heterocycloalkyl, dihalo$(C_{3-7})$heterocycloalkyl, $C_{1-6}$ alkoxy, difluoromethoxy and trifluoromethoxy.

8. The compound as claimed in claim 7 wherein Z represents (methoxy)(methyl)-phenyl, (difluoromethoxy)(methyl)phenyl, (chloro)(trifluoromethoxy)phenyl, (methyl)-(trifluoromethoxy)phenyl, (azetidinyl)(methyl)pyridinyl, (difluoroazetidinyl)(methyl)-pyridinyl, (methoxy)(methyl)pyridinyl, (methoxy)(trifluoromethyl)pyridinyl, dimethoxy-pyridinyl or (ethoxy)(methyl)pyridinyl.

9. The compound as claimed in claim 1 wherein $R^2$ represents hydrogen or methyl.

10. The compound as claimed in claim 1 wherein $R^3$ represents hydrogen, chloro or methyl.

11. The compound of formula (I) as defined in claim 1 that is
- (3S)-4-(2-Aminopyrazolo[1,5-a][1,3,5]triazin-4-yl)-N-(4-methoxy-2-methylphenyl)-3-methylpiperazine-1-carboxamide;
- (3S)-4-(2-Aminopyrazolo[1,5-a][1,3,5]triazin-4-yl)-3-methyl-N-[2-methyl-4-(trifluoro-methoxy)phenyl]piperazine-1-carboxamide;
- (3S)-4-(2-Aminopyrazolo[1,5-a][1,3,5]triazin-4-yl)-N-(6-ethoxy-2-methylpyridin-3-yl)-3-methylpiperazine-1-carboxamide;
- (3S)-4-(2-Amino-8-methylpyrazolo[1,5-a][1,3,5]triazin-4-yl)-N-[6-(3,3-difluoroazetidin-1-yl)-2-methylpyridin-3-yl]-3-methylpiperazine-1-carboxamide;
- (3S)-4-(2-Amino-8-methylpyrazolo[1,5-a][1,3,5]triazin-4-yl)-N-(4-methoxy-2-methyl-phenyl)-3-methylpiperazine-1-carboxamide;
- (3S)-4-(2-Amino-8-methylpyrazolo[1,5-a][1,3,5]triazin-4-yl)-3-methyl-N-[2-methyl-4-(trifluoromethoxy)phenyl]piperazine-1-carboxamide;
- (3S)-4-(2-Amino-8-methylpyrazolo[1,5-a][1,3,5]triazin-4-yl)-N-(6-ethoxy-2-methyl-pyridin-3-yl)-3-methylpiperazine-1-carboxamide formate;
- (3S)-4-(2-Amino-7-methylpyrazolo[1,5-a][1,3,5]triazin-4-yl)-N-(4-methoxy-2-methyl-phenyl)-3-methylpiperazine-1-carboxamide;

(3S)-4-[2-Amino-7-(4-fluorophenyl)pyrazolo[1,5-a][1,3,5]triazin-4-yl]-N-(4-methoxy-2-methylphenyl)-3-methylpiperazine-1-carboxamide;

(3S)-4-[2-Amino-7-(4-fluorophenyl)pyrazolo[1,5-a][1,3,5]triazin-4-yl]-N-[6-(3,3-difluoroazetidin-1-yl)-2-methylpyridin-3-yl]-3-methylpiperazine-1-carboxamide;

(3S)-4-(2-Amino-8-chloropyrazolo[1,5-a][1,3,5]triazin-4-yl)-N-(4-methoxy-2-methyl-phenyl)-3-methylpiperazine-1-carboxamide;

(3S)-4-(2-Amino-8-chloropyrazolo[1,5-a][1,3,5]triazin-4-yl)-3-methyl-N-[2-methyl-4-(trifluoromethoxy)phenyl]piperazine-1-carboxamide;

(3S)-4-(2-Amino-8-chloropyrazolo[1,5-a][1,3,5]triazin-4-yl)-N-(6-ethoxy-2-methyl-pyridin-3-yl)-3-methyl-piperazine-1-carboxamide;

(3S)-4-(2-Amino-8-chloropyrazolo[1,5-a][1,3,5]triazin-4-yl)-N-(2,6-dimethoxypyridin-3-yl)-3-ethylpiperazine-1-carboxamide;

(3S)-4-(2-Amino-8-chloropyrazolo[1,5-a][1,3,5]triazin-4-yl)-3-ethyl-N-(4-methoxy-3-methylphenyl)piperazine-1-carboxamide;

(3S)-4-(2-Amino-8-chloropyrazolo[1,5-a][1,3,5]triazin-4-yl)-N-[2-chloro-4-(trifluoro-methoxy)phenyl]-3-ethylpiperazine-1-carboxamide;

(3S)-4-(2-Amino-8-chloropyrazolo[1,5-a][1,3,5]triazin-4-yl)-3-ethyl-N-[2-methyl-4-(trifluoromethoxy)phenyl]piperazine-1-carboxamide;

(3S)-4-(2-Amino-8-methylpyrazolo[1,5-a][1,3,5]triazin-4-yl)-N-(2,6-dimethoxypyridin-3-yl)-3-ethylpiperazine-1-carboxamide;

(3S)-4-(2-Amino-8-methylpyrazolo[1,5-a][1,3,5]triazin-4-yl)-3-ethyl-N-(4-methoxy-3-methylphenyl)piperazine-1-carboxamide;

(3S)-4-(2-Amino-8-methylpyrazolo[1,5-a][1,3,5]triazin-4-yl)-N-[2-chloro-4-(trifluoro-methoxy)phenyl]-3-ethylpiperazine-1-carboxamide;

(3S)-4-(2-Amino-8-methylpyrazolo[1,5-a][1,3,5]triazin-4-yl)-3-ethyl-N-[2-methyl-4-(trifluoromethoxy)phenyl]piperazine-1-carboxamide;

(3S)-4-(2-Amino-8-methylpyrazolo[1,5-a][1,3,5]triazin-4-yl)-3-ethyl-N-(4-methoxy-2-methylphenyl)piperazine-1-carboxamide;

(3S)-4-(2-Amino-8-methylpyrazolo[1,5-a][1,3,5]triazin-4-yl)-N-(2,6-dimethoxypyridin-3-yl)-3-methylpiperazine-1-carboxamide;

(3S)-4-(2-Amino-8-methylpyrazolo[1,5-a][1,3,5]triazin-4-yl)-N-(4-methoxy-3-methyl-phenyl)-3-methylpiperazine-1-carboxamide;

(3S)-4-(2-Amino-8-methylpyrazolo[1,5-a][1,3,5]triazin-4-yl)-N-[2-chloro-4-(trifluoro-methoxy)phenyl]-3-methylpiperazine-1-carboxamide;

(3S)-4-(2-Aminopyrazolo[1,5-a][1,3,5]triazin-4-yl)-N-(2,6-dimethoxypyridin-3-yl)-3-ethylpiperazine-1-carboxamide;

(3S)-4-(2-Aminopyrazolo[1,5-a][1,3,5]triazin-4-yl)-3-ethyl-N-(4-methoxy-3-methyl-phenyl)piperazine-1-carboxamide;

(3S)-4-(2-Aminopyrazolo[1,5-a][1,3,5]triazin-4-yl)-3-ethyl-N-[2-methyl-4-(trifluoro-methoxy)phenyl]piperazine-1-carboxamide;

(3S)-4-(2-Aminopyrazolo[1,5-a][1,3,5]triazin-4-yl)-3-ethyl-N-(4-methoxy-2-methyl-phenyl)piperazine-1-carboxamide;

(3S)-4-(2-Aminopyrazolo[1,5-a][1,3,5]triazin-4-yl)-3-ethyl-N-[5-methoxy-6-(trifluoro-methyl)pyridin-2-yl]piperazine-1-carboxamide;

(3S)-4-(2-Aminopyrazolo[1,5-a][1,3,5]triazin-4-yl)-N-[6-(azetidin-1-yl)-2-methylpyridin-3-yl]-3-ethylpiperazine-1-carboxamide;

(3S)-4-(2-Amino-8-methylpyrazolo[1,5-a][1,3,5]triazin-4-yl)-N-[5-methoxy-6-(trifluoro-methyl)pyridin-2-yl]-3-methylpiperazine-1-carboxamide;

(3S)-4-(2-Amino-8-methylpyrazolo[1,5-a][1,3,5]triazin-4-yl)-N-[6-(azetidin-1-yl)-2-methylpyridin-3-yl]-3-methylpiperazine-1-carboxamide;

(3S)-4-(2-Amino-8-methylpyrazolo[1,5-a][1,3,5]triazin-4-yl)-3-ethyl-N-[5-methoxy-6-(trifluoromethyl)pyridin-2-yl]piperazine-1-carboxamide; or (3S)-4-(2-Amino-8-methylpyrazolo[1,5-a][1,3,5]triazin-4-yl)-N-[6-(azetidin-1-yl)-2-methylpyridin-3-yl]-3-ethylpiperazine-1-carboxamide.

12. A pharmaceutical composition comprising a compound of formula (I) as defined in claim 1, or a pharmaceutically acceptable salt or solvate thereof, in association with a pharmaceutically acceptable carrier.

13. A method for the treatment of malaria, or the management of organ or cell transplant rejection, which method comprises administering to a patient in need of such treatment an effective amount of a compound of formula (I) as defined in claim 1, or a pharmaceutically acceptable salt or solvate thereof.

* * * * *